United States Patent [19]
Macor et al.

[11] Patent Number: 6,087,368
[45] Date of Patent: Jul. 11, 2000

[54] QUINAZOLINONE INHIBITORS OF CGMP PHOSPHODIESTERASE

[75] Inventors: John E. Macor, Flemington, N.J.; David P. Rotella, Newtown, Pa.; Harold N. Weller, III, Pennington; David W. Cushman, Lawrenceville, both of N.J.; Joseph P. Yevich, Southington, Conn.

[73] Assignee: Bristol-Myers Squibb Company, Princeton, N.J.

[21] Appl. No.: 09/322,678

[22] Filed: May 28, 1999

Related U.S. Application Data

[60] Provisional application No. 60/088,538, Jun. 8, 1998.

[51] Int. Cl.$^7$ ........................ A61K 31/505; C07D 487/04
[52] U.S. Cl. .......................... 514/267; 544/118; 544/123; 544/251
[58] Field of Search .................................... 544/251, 118, 544/123; 514/267

[56] References Cited

U.S. PATENT DOCUMENTS

| | | | |
|---|---|---|---|
| 4,352,931 | 10/1982 | Cuny et al. | 544/251 |
| 5,116,843 | 5/1992 | Mertens et al. | 514/253 |
| 5,250,534 | 10/1993 | Bell et al. | 544/262 |
| 5,272,147 | 12/1993 | Bell et al. | 544/262 |
| 5,346,901 | 9/1994 | Bell et al. | 544/262 |
| 5,426,107 | 6/1995 | Bell et al. | 544/262 |
| 5,482,941 | 1/1996 | Terrett | 544/284 |

FOREIGN PATENT DOCUMENTS

98/08848  3/1998  WIPO .

OTHER PUBLICATIONS

Hudlicky, Milos., Reductions in Organic Chemistry, 41–73, 1984.

Drugs of the Future 1997, 22(2): 138–143.

*Primary Examiner*—Mukund J. Shah
*Assistant Examiner*—V Balasubramanian
*Attorney, Agent, or Firm*—Stephen B. Davis; Suzanne Babajko

[57] ABSTRACT

Novel quinazolinone compounds, methods of using such compounds in the treatment of cGMP-associated conditions such as erectile dysfunction, and pharmaceutical compositions containing such compounds.

17 Claims, No Drawings

QUINAZOLINONE INHIBITORS OF CGMP PHOSPHODIESTERASE

This application claims priority from provisional U.S. Application Ser. No. 60/088,538, filed Jun. 8, 1998, incorporated herein by reference in its entirety.

FIELD OF THE INVENTION

The present invention relates to quinazolinone compounds, to methods of using such compounds in the treatment of cGMP-associated conditions such as erectile dysfunction, and to pharmaceutical compositions containing such compounds.

BACKGROUND OF THE INVENTION

Erectile dysfunction is the inability to obtain and maintain a penile erection sufficient for sexual intercourse or other sexual expression. A number of factors can place an individual at risk for this disorder, for example, trauma, pelvic surgery, hypercholesterolemia, ischemic heart disease, peripheral vascular disease, chronic renal failure, diabetes, or the use of medicaments such as antihypertensive medication or digoxin, or illicit drugs, cigarettes or alcohol. Methods for the treatment of erectile dysfunction include the use of vacuum devices and penile implants, as well as the administration of medicaments such as yohimbine, papaverine and apomorphine. Improved methods for the treatment of this disorder are sought, however, as the aforementioned methods do not provide sufficient efficacy, and/or are accompanied by drawbacks or side effects such as erosion, pain, priapism or gastrointestinal discomfort.

As penile erection is dependent upon the presence of adequate levels of cyclic guanosine 3',5'-monophosphate (cGMP), especially in corpora cavernosa tissue, administration of an inhibitor of a cGMP phosphodiesterase (cGMP PDE) (and particularly, a selective inhibitor of cGMP PDE Type V (cGMP PDE V, also referred to as cGMP PDE 5)) provides a means for achieving and maintaining an erection, and therefore for treating erectile dysfunction. See Trigo-Rocha et al., "Nitric Oxide and cGMP: mediators of pelvic nerve-stimulated erection in dogs," *Am. J. Physiol.*, Vol. 264 (Febuary 1993); Bowman et al., "Cyclic GMP mediates neurogenic relaxation in the bovine retractor penis muscle," *Br. J. Pharmac.*, 81, 665–674 (1984); and Rajfer et al., "Nitric Oxide as a Mediator of Relaxation of the Corpus Cavernosum in Response to Nonadrenergic, Noncholinergic Neurotransmission," *New England J. Med.*, 326, 2, 90–94 (January 1992). Sildenafil, for example, has been described as a phosphodiesterase Type V inhibitor useful for the treatment of erectile dysfunction. See *Drugs of the Future*, 22, 138–143 (1997).

The present invention provides novel compounds which are potent and selective inhibitors of cGMP PDE V which may be employed in the treatment of erectile dysfunction. In view of their activity, the present compounds can also be employed in the treatment of other disorders responding to the inhibition of cGMP PDE such as various cardiovascular disorders.

SUMMARY OF THE INVENTION

The present invention provides quinazolinone compounds of the following formula I and salts thereof, for use as inhibitors of cGMP PDE, especially Type V:

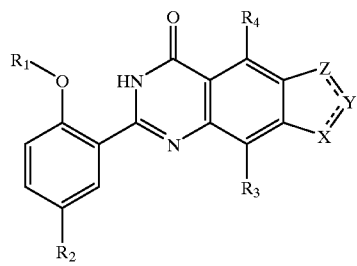

where, throughout this specification unless otherwise indicated:

X, Y and Z are defined such that
when X is —N($R_9$)— and Y is —CH=, Z is —N=;
when X is —N($R_9$)— and Y is —N=, Z is —N= or —C($R_9$)=;
when Z is —N($R_9$)— and Y is —CH=, X is —N=;
when Z is —N($R_9$)— and Y is —N=, X is —N= or —C($R_9$)=;

the dotted lines denote optional double bonds;

$R_1$ is alkyl, alkenyl, alkynyl, cycloalkyl, cycloalkenyl, aryl, alkoxyalkyl, or haloalkyl;

$R_2$ is hydrogen, halo, cyano, nitro, —(CH$_2$)$_n$—N$_3$, —(CH$_2$)$_n$—SO$_2$NR$_5$R$_6$, —(CH$_2$)$_n$—CO$_2$R$_7$, —(CH$_2$)$_n$—(C=O)NR$_5$R$_6$, —(CH$_2$)$_n$—NR$_5$R$_6$, —(CH$_2$)$_n$—NH(C=O)R$_8$, or —(CH$_2$)$_n$—NHSO$_2$R$_8$;

$R_3$ and $R_4$ are each independently hydrogen, alkyl, alkenyl, alkynyl, cycloalkyl, cycloalkylalkyl, cycloalkenyl, cycloalkenylalkyl, halo, aryl, arylalkyl, heterocyclo (such as heteroaryl), heterocycloalkyl, —OR$_{12}$ or —NHR$_{12}$;

$R_5$, $R_6$, $R_7$ and $R_8$ are each independently hydrogen, heterocyclo or alkyl, wherein said alkyl is optionally substituted with —CO$_2$R$_{10}$, hydroxy, amino, mono- or dialkylamino or heterocyclo; or $R_5$ and $R_6$ may, together with the nitrogen to which they are bonded, form a five to seven membered heterocyclic ring optionally substituted by one or two of the following groups: alkyl, aryl, arylalkyl, heterocyclo, cycloalkyl, hydroxyalkyl, —(CH$_2$)$_n$—CO$_2$R$_{10}$, —N(R$_{10}$)R$_{11}$, —(CH$_2$)$_n$—(CO)NR$_{13}$R$_{14}$, —COR$_{10}$ or —(CH$_2$)$_n$—OR$_{11}$;

each $R_9$ is independently hydrogen, alkyl, alkenyl, alkynyl, cycloalkyl, cycloalkylalkyl, cycloalkenyl, cycloalkenylalkyl, heterocyclo (such as heteroaryl), heterocycloalkyl, aryl or arylalkyl;

$R_{10}$, $R_{11}$ and $R_{12}$ are each independently hydrogen, alkyl, alkenyl, alkynyl, cycloalkyl, cycloalkylalkyl, cycloalkenyl, cycloalkenylalkyl, halo, aryl or arylalkyl;

$R_{13}$ and $R_{14}$ are each independently hydrogen, hydroxy, alkyl, alkoxy (such as methoxy), alkoxyalkyl, hydroxyalkyl, alkylaminoalkyl, dialkylaminoalkyl, arylalkyl, heterocycloalkyl (such as heteroarylalkyl), or heterocyclo, or $R_{13}$ and $R_{14}$ may, together with the nitrogen to which they are bonded, form a five to seven membered heterocyclic ring (preferably containing 1 or 2 heteroatoms); and n is 0, 1, 2, 3 or 4;

wherein cycloalkyl or cycloalkenyl alone or as part of another group may optionally be substituted by one or more (such as one to three) halo atoms, and wherein aryl alone or as part of another group may optionally be substituted by one or more (such as one to three) halo, cyano, nitro, alkyl or alkoxy groups.

PREFERRED COMPOUNDS

A preferred subgenus of the compounds of the present invention includes compounds of the formula I or salts thereof wherein:

X is —N($R_9$)— or —N═;

Z is —N═ when X is —N($R_9$)—, or is —N($R_9$)— when X is —N═;

Y is —CH═ or —N═;

$R_1$ is $C_1$ to $C_6$ alkyl, $C_2$ to $C_6$ alkenyl, $C_2$ to $C_6$ alkynyl, —($CH_2$)$_k$O($CH_2$)$_m$$CH_3$, or $C_1$ to $C_6$ perfluoroalkyl;

$R_2$ is hydrogen, fluoro, chloro, bromo, iodo, cyano, nitro, —($CH_2$)$_n$—$N_3$, —($CH_2$)$_n$—$SO_2NR_5R_6$, —($CH_2$)$_n$—$CO_2R_7$, —($CH_2$)$_n$—(C═O)$NR_5R_6$, —($CH_2$)$_n$—$NR_5R_6$, —($CH_2$)$_n$—NH(C═O)$R_8$, or —($CH_2$)$_n$—$NHSO_2R_8$;

$R_3$ and $R_4$ are each independently hydrogen, $C_1$ to $C_6$ alkyl, $C_2$ to $C_6$ alkenyl, $C_2$ to $C_6$ alkynyl, —$CH_2$-(optionally substituted phenyl), —$CH_2CH_2$—(optionally substituted phenyl), —$OR_{12}$ or —$NHR_{12}$;

k is 2 or 3;

m is 0, 1 or 2;

n is 0, 1, 2, 3 or 4;

$R_5$ and $R_6$ are each independently hydrogen, heterocyclo or alkyl (such as $C_1$ to $C_5$ alkyl), wherein said alkyl is optionally substituted with —$CO_2R_{10}$, hydroxy, dialkylamino or heterocyclo (such as pyridyl, imidazolyl, morpholinyl, or oxadiazolyl), or $R_5$ and $R_6$, together with the nitrogen to which they are bonded, form a five to seven membered heterocyclic ring (such as a five to seven membered heterocyclic ring containing as heteroatoms the nitrogen to which $R_5$ and $R_6$ are bonded and, optionally, an additional nitrogen atom), optionally substituted by one or two of the following groups: alkyl (such as $C_1$ to $C_4$ alkyl), (optionally substituted phenyl)-alkyl, hydroxyalkyl, —$CO_2R_{10}$, —N($R_{10}$)$R_{11}$, —(CO)$NR_{13}R_{14}$, —$COR_{10}$ or —$OR_{11}$;

$R_7$ and $R_8$ are each independently hydrogen or $C_1$ to $C_5$ alkyl, wherein said alkyl may optionally be substituted with —$CO_2R_{10}$, hydroxy, pyridyl, imidazolyl, morpholinyl or oxadiazolyl;

$R_9$ is hydrogen, $C_1$ to $C_8$ alkyl, $C_2$ to $C_6$ alkenyl, $C_2$ to $C_6$ alkynyl, —$CH_2$—(optionally substituted phenyl), or —$CH_2CH_2$—(optionally substituted phenyl); and $R_{10}$, $R_{11}$ and $R_{12}$ are each independently hydrogen or $C_1$ to $C_6$ alkyl.

Compounds of the formula I and salts thereof wherein one or more, and especially all, of Z, X, $R_1$, $R_2$, $R_3$, $R_4$, $R_5$, $R_6$ and $R_9$ are selected from the following definitions, are more preferred compounds of the present invention:

Z is —N($R_9$)—;

X is —N═;

$R_1$ is $C_2$ to $C_4$ alkyl;

$R_2$ is hydrogen, halo, cyano, nitro, —($CH_2$)$_n$—$N_3$, —($CH_2$)$_n$—$SO_2NR_5R_6$, —($CH_2$)$_n$—$CO_2R_7$, —($CH_2$)$_n$—(C═O)$NR_5R_6$, —($CH_2$)$_n$—$NR_5R_6$, —($CH_2$)$_n$—NH(C═O)$R_8$, or —($CH_2$)$_n$—$NHSO_2R_8$ (such as —$SO_2NR_5R_6$, —(C═O)$NR_5R_6$, —NH(C═O)$R_8$, or —$NHSO_2R_8$);

$R_3$ and $R_4$ are each independently hydrogen, $C_1$ to $C_3$ alkyl, —$OR_{12}$ or —$NHR_{12}$;

$R_5$ and $R_6$ are each independently hydrogen, heterocyclo or alkyl (such as $C_1$ to $C_5$ alkyl), wherein said alkyl is optionally substituted with —$CO_2R_{10}$, hydroxy, dialkylamino or heterocyclo (such as pyridyl, imidazolyl, morpholinyl or oxadiazolyl), or $R_5$ and $R_6$, together with the nitrogen to which they are bonded, form a five to seven membered heterocyclic ring (such as a five to seven membered heterocyclic ring containing as heteroatoms the nitrogen to which $R_5$ and $R_6$ are bonded and, optionally, an additional nitrogen atom), optionally substituted by one or two of the following groups: alkyl (such as $C_1$ to $C_4$ alkyl), (optionally substituted phenyl)-alkyl, hydroxyalkyl, —$CO_2R_{10}$, —N($R_{10}$)$R_{11}$, —(CO)$NR_{13}R_{14}$, —$COR_{10}$ or —$OR_{11}$; and $R_9$ is hydrogen, $C_1$ to $C_8$ alkyl, —$CH_2$-(optionally substituted phenyl), or —$CH_2CH_2$-(optionally substituted phenyl).

Most preferred are compounds of the formula I and salts thereof wherein one or more, and especially all, of $R_1$, $R_2$, $R_3$, $R_4$, $R_5$, $R_6$ and $R_9$ are selected from the following definitions:

$R_1$ is $C_2$ to $C_4$ alkyl;

$R_2$ is as defined above, especially —$SO_2NR_5R_6$ or —(C═O)$NR_5R_6$;

$R_3$ and $R_4$ are each independently hydrogen or —$NHR_{12}$;

$R_5$ and $R_6$ are as defined above, and especially, together form a five or six membered heterocyclic ring containing as heteroatoms the nitrogen to which $R_5$ and $R_6$ are bonded and, optionally, an additional nitrogen atom, which ring may optionally be substituted by a $C_1$ to $C_4$ alkyl group or a group —N($R_{10}$)$R_{11}$; or when $R_2$ is —(C═O)$NR_5R_6$, $R_5$ and $R_6$ are hydrogen and $R_9$ is hydrogen, —$CH_2$-(optionally substituted phenyl), or —$CH_2CH_2$-(optionally substituted phenyl).

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

The term "alkoxy" refers to an alkyl group bonded through an oxygen (—O—). The terms "haloalkyl" and "hydroxyalkyl" refer to alkyl groups substituted by one or more halo or hydroxy groups, respectively.

The term "alkenyl" refers to straight or branched chain hydrocarbon groups of 2 to 10, preferably 2 to 4, carbon atoms having at least one double bond.

The term "alkynyl" refers to straight or branched chain hydrocarbon groups of 2 to 10, preferably 2 to 4, carbon atoms having at least one triple bond.

The terms "ar" or "aryl" refer to phenyl, naphthyl and biphenyl. Phenyl is a preferred aryl group. "Optionally substituted phenyl" refers to phenyl optionally substituted by one to three substituents selected from halo, cyano, nitro, alkyl, amino, mono- or dialkylamino or alkoxy groups.

The terms "cycloalkyl" and "cycloalkenyl" refer to cyclic hydrocarbon groups of 3 to 8 carbon atoms which are, respectively, fully saturated and partially unsaturated.

The terms "halogen" and "halo" refer to fluorine, chlorine, bromine and iodine.

The terms "heterocycle", "heterocyclic" or "heterocyclo" refer to optionally substituted, fully saturated or unsaturated, including aromatic ("heteroaryl") or nonaromatic cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. Exemplary optional substituents may be selected from one or more hydrogen, halo, cyano, nitro, alkoxycarbonyl, alkyl or alkoxy groups.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl and the like.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains a both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as, but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as, but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

Compounds of the formula I, and salts thereof, may exist in their tautomeric form (for example, as an amide or imino ether). All such tautomeric forms are contemplated herein as part of the present invention.

All stereoisomers of the present compounds, such as those which may exist due to asymmetric carbons on the $R_{11}$ to $R_{11}$ substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

METHODS OF PREPARATION

The compounds of the present invention may be prepared by methods such as those illustrated in the following Schemes I to VII. Solvents, temperatures, pressures, and other reaction conditions may readily be selected by one of ordinary skill in the art. Starting materials are commercially available or readily prepared by one of ordinary skill in the art.

Combinatorial techniques may be employed in the preparation of compounds, for example, where the intermediates possess a sulfonyl halide or active ester group.

SCHEME I

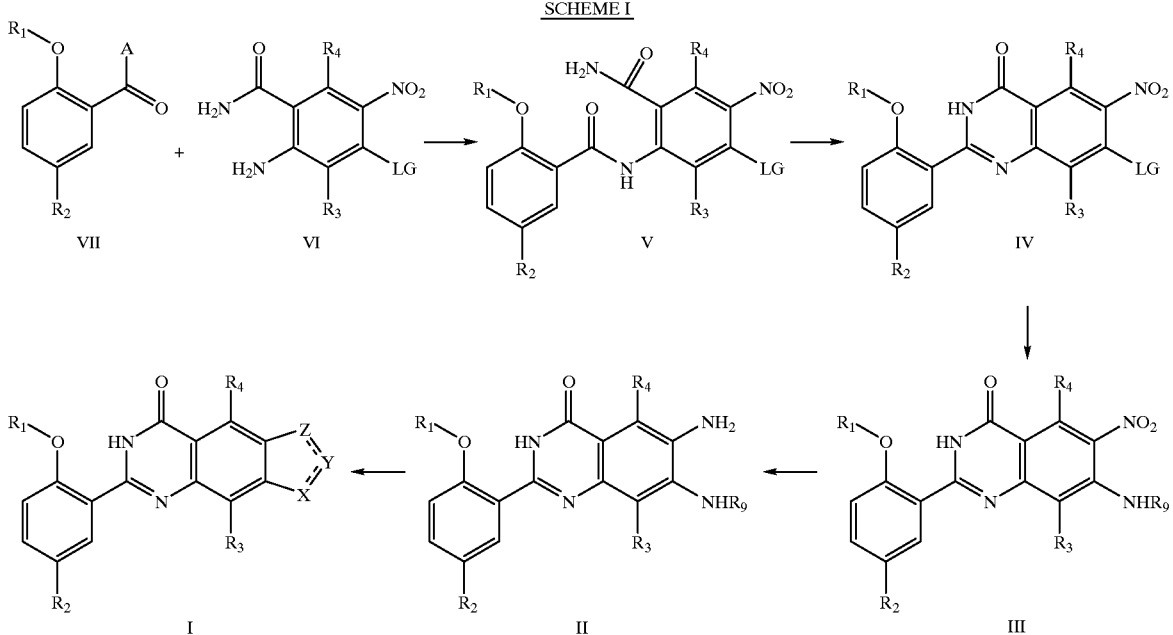

Compounds of formula I where Y is —CH═ can be prepared via the cyclization of a compound of formula II with a formic acid source in an inert solvent as appropriate, typically under elevated temperatures. Formic acid is an exemplary formic acid source and can also be used as the reaction solvent. Alternatively, compounds of formula I can be prepared from compounds of formula III using a formic acid source in the presence of a reducing catalyst such as palladium on carbon at elevated temperatures. Formic acid is an exemplary formic acid source and palladium on charcoal is an exemplary reducing catalyst.

Compounds of formula I where Y is —N═ can be prepared by treating a compound of formula II with a diazotizing reagent in an acidic aqueous medium. Sodium nitrite is an exemplary diazotizing reagent and dilute (1N) HCl is an exemplary reaction solvent.

Compounds of formula II can be prepared via the reduction of a compound of formula III in an inert solvent. This reduction may, for example, be mediated via a platinum or palladium-catalyzed hydrogenation using platinum or palladium on carbon, hydrogen and an inert solvent such as ethanol or methanol or, alternatively, by use of stannous(II) chloride in an inert solvent such as ethyl acetate.

Compounds of formula III can be prepared via the reaction of an amine of the formula $R_9NH_2$ with a compound of formula IV (wherein LG is chloride or fluoride), in an inert solvent such as ethanol, typically under elevated pressure and temperature.

Compounds of formula IV can be prepared via the condensation of a compound of formula V under basic conditions, typically using elevated temperature in an inert solvent. Sodium hydroxide with hydrogen peroxide or potassium tert-butoxide are exemplary bases, and ethanol or tert-butanol are exemplary solvents.

Compounds of formula V can be prepared via the condensation of a compound of formula VI with a compound of formula VII wherein A is the active component of an active ester, typically chloride, using pyridine as solvent.

Compounds of formula VI and VII are either commercially available or available via methods known to one skilled in the art.

Certain compounds of formula I may also be prepared as depicted in Scheme II.

SCHEME II

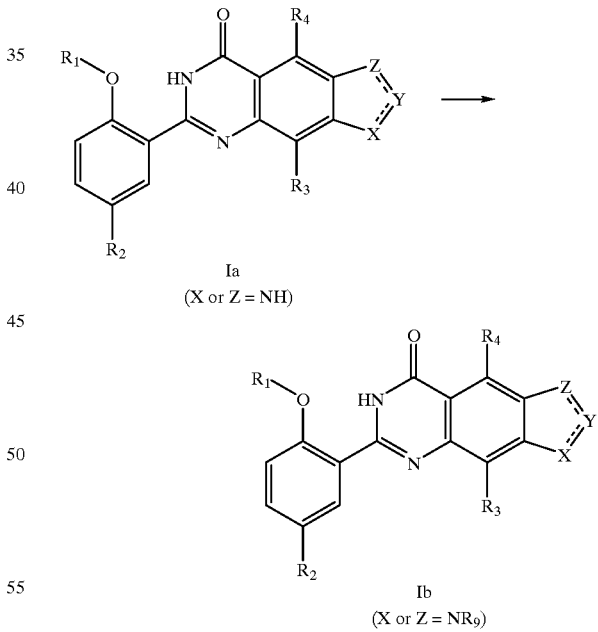

Ia
(X or Z = NH)

Ib
(X or Z = $NR_9$)

Compounds of formula Ib wherein X or Z is —$NR_9$— can be prepared by the alkylation of compounds of formula Ia wherein X or Z is —NH— using a base and an appropriate alkylating agent in an inert solvent. Exemplary bases include sodium carbonate, potassium carbonate or cesium carbonate. N,N-dimethylformamide is an exemplary solvent.

Compounds of formula Ia may be prepared as described in Scheme I.

Certain compounds of formula I may also be prepared as depicted in Scheme III.

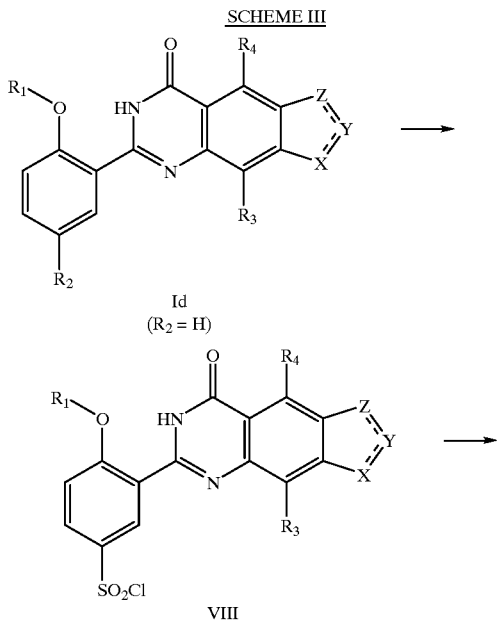

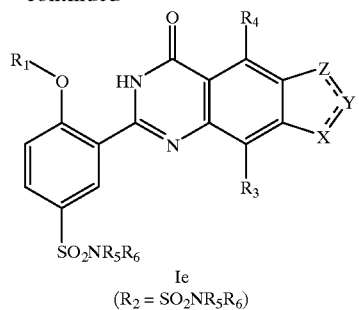

Compounds of formula Ie wherein $R_2$ is $-SO_2NR_5R_6$ can be prepared by the reaction of compounds of formula VIII with amines of the formula $HNR_5R_6$ in an inert solvent and an added base. Exemplary solvents for this reaction include methylene chloride, isopropanol or ethanol. Exemplary added bases include triethylamine and diisopropylethylamine. Alternatively, amines of formula $HNR_5R_6$ can be used in excess.

Compounds of formula VIII can be prepared from the reaction of compounds of formula Id wherein $R_2$ is hydrogen with chlorosulfonic acid in an inert solvent. Alternatively, chlorosulfonic acid can serve as solvent.

Compounds of formula Id may be prepared as described in Schemes I, II, V and VI. Amines of the formula $HNR_5R_6$ are either commercially available or available via methods known to one of ordinary skill in the art.

Certain compounds of formula I may also be prepared as depicted in Scheme IV.

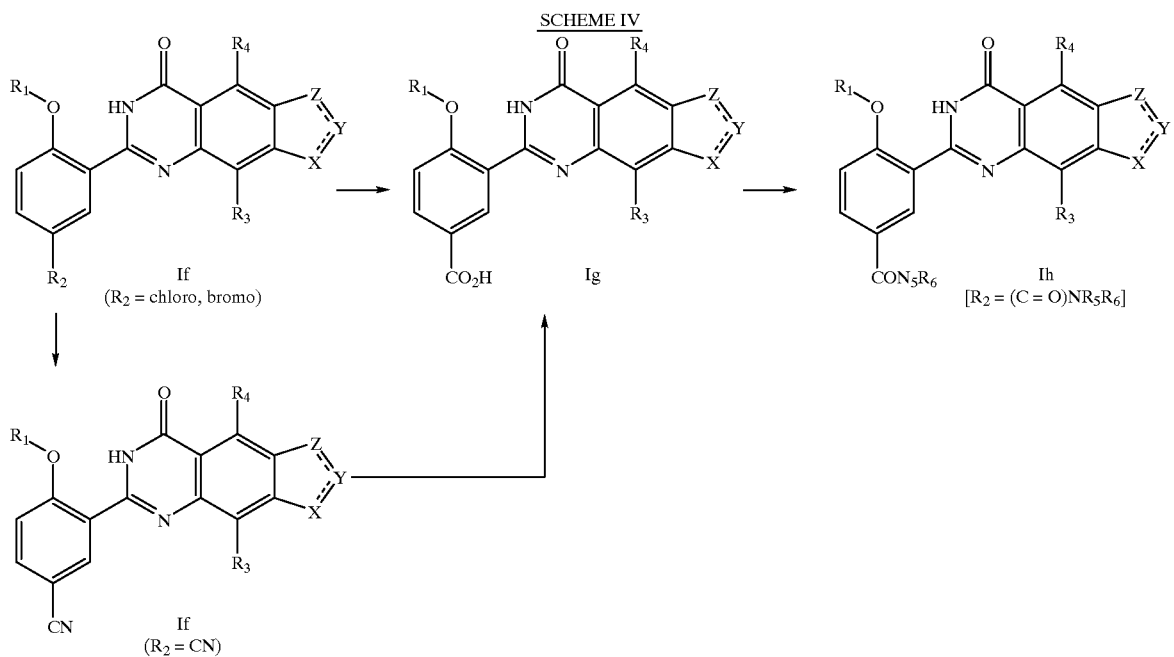

Compounds of formula Ih wherein $R_2$ is —$CONR_5R_6$ can be prepared by the reaction of compounds of formula Ig in the presence of acid activating agents (to form active esters) with amines of the formula $HNR_5R_6$ in an inert solvent. Exemplary active esters include acid chlorides, as well as intermediates derived from activating reagents such as carbodiimides in the presence of 2-hydroxybenzotriazole and added amine bases such as 4-dimethylaminopyridine or triethylamine. Exemplary inert solvents include methylene chloride or tetrahydrofuran. Amines of the formula $HNR_5R_6$ are either commercially available or available via methods known to one of ordinary skill in the art.

Compounds of formula Ig can be prepared by reaction of compounds of formula If wherein $R_2$ is chloro or bromo using a metallating agent and a carbon dioxide source in an inert solvent at low temperature. Exemplary metallating agents include alkyl lithiums such as n-butyl lithium. Carbon dioxide gas is an exemplary carbon dioxide source. Tetrahydrofuran is an exemplary inert solvent. Low temperatures (e.g., −78° C.) are preferred. Compounds of formula Ig can also be prepared from compounds of formula If ($R_2$=CN) by hydrolysis using alkali metal hydroxides in aqueous alcoholic solvents. Exemplary alkali metal hydroxides include sodium and potassium hydroxide and exemplary alcoholic solvents include methanol and ethanol.

Compounds of formula If ($R_2$=chloro, bromo) may be prepared as described in Schemes I, II, V and VI. Compounds of formula If ($R_2$=CN) can be prepared from compounds of formula If ($R_2$=bromo), and also from the corresponding compounds of the formula I where $R_2$=iodo (which also may be prepared as described above), by aromatic substitution using a cyanide source in an inert solvent at elevated temperature with or without a catalyst. Exemplary cyanide sources include copper(I) or zinc cyanide. Exemplary inert solvents include N-methyl pyrrolidinone and DMF. Exemplary catalysts include palladium(tetrakis)triphenylphosphine.

Certain compounds of formula I may also be prepared as depicted in Scheme V.

SCHEME V

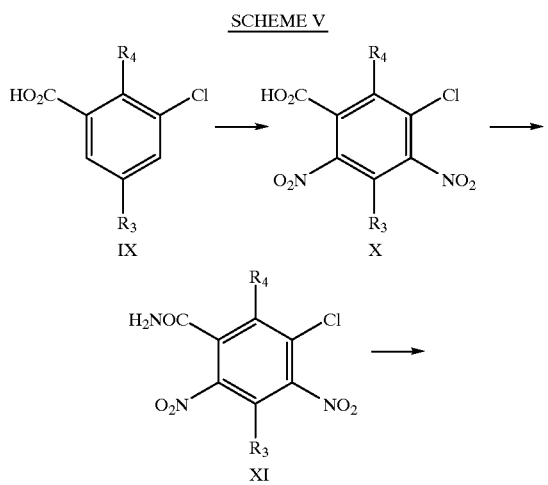

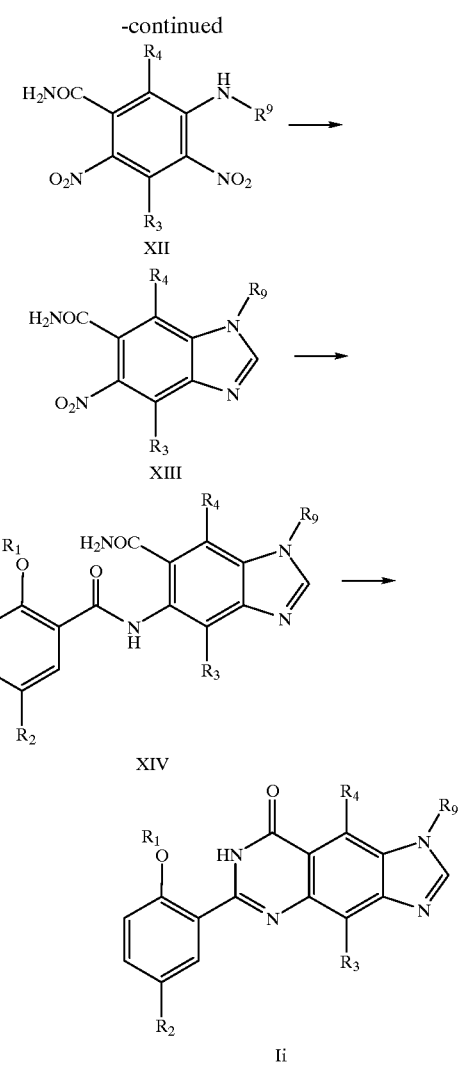

Compounds of formula Ii can be prepared as shown in Scheme V. Cyclization of compounds of formula XIV in the presence of a suitable base in an inert solvent at elevated temperature leads to compounds of formula Ii. Exemplary bases for this cyclization include potassium-t-butoxide or sodium hydroxide in the presence of hydrogen peroxide. Exemplary inert solvents include methyl and ethyl alcohol and t-butanol.

Compounds of formula XIV can be prepared by acylation of compounds of formula XIII using active carboxylic esters of formula VII (Scheme I). Exemplary active esters include acid chlorides, as well as intermediates derived from activating reagents such as carbodiimides in the presence of 2-hydroxybenzotriazole and added amine bases such as 4-dimethylaminopyridine or triethylamine.

Compounds of formula XIII can be prepared from compounds of formula XII without isolation of intermediates. For example, compounds of formula XII can be reduced by treatment with a hydrogen source and a catalyst in an inert solvent, followed immediately without further purification by reaction with a suitable formic acid source in an inert solvent. Exemplary hydrogen sources include hydrogen gas in presence of platinum or palladium catalysts. Exemplary solvents for this transformation include methyl and ethyl alcohol. Formic acid sources include formic acid, which can also be used as solvent. This step is followed by treatment of the intermediate with dilute aqueous acid in an inert solvent at room temperature. Hydrochloric acid (5 to 10% v/v) is an exemplary acid. Methanol and ethanol are exemplary inert solvents.

Compounds of formula XII can be prepared from compounds of formula XI by reaction of amines of the formula $R_9NH_2$ and compounds of formula XI in an inert solvent in the presence of a tertiary amine base at elevated temperature. Exemplary tertiary amine bases include triethylamine and diisopropylethylamine. Exemplary inert solvents include tetrahydrofuran and methylene chloride. Amines of the formula $R_9NH_2$ are obtained commercially or by methods known to those skilled in the art.

Compounds of formula XI can be obtained from compounds of formula X using carboxyl activating agents such as thionyl chloride or oxalyl chloride in an inert solvent, followed by treatment of the intermediate active ester with ammonium hydroxide in an inert solvent. Tetrahydrofuran, acetone and methylene chloride are exemplary inert solvents for this sequence.

Compounds of formula X can be obtained by nitration of compounds of formula IX—the latter which may be obtained from commercial sources—using, for example, potassium nitrate in sulfuric acid at temperatures between 120° C. and 145° C. or a mixture of fuming nitric acid in concentrated sulfuric acid at about the same temperatures.

Certain compounds of formula Ij where Z is —N($R_9$)—, Y is —N═, and X is —C($R_9$)═, or where Z is —C($R_9$)═, Y is —N═, and X is —N($R_9$)—, can be prepared as shown in Scheme VI. Compounds of formula Ij can be prepared from compounds of formula XVII by cyclization using the methods described in Scheme I or Scheme V.

Compounds of formula XVII can be prepared from compounds of formula XVI by methods analogous to those described in Scheme V for conversion of compounds of formula X to compounds of formula XI.

Compounds of formula XVI can be prepared from compounds of formula XV and compounds of formula VII using methods analogous to those described in Scheme I and Scheme V.

Compounds of formula XV can be prepared according to methods known in the literature (Cuny et al., *Chem. Ber.* 1981, 114, 1624–1635; Cuny et al., *Tet. Lett.* 1980, 21, 3029–3032; Lichtentaler et al., *Tet. Lett.* 1981, 22, 4397–4400).

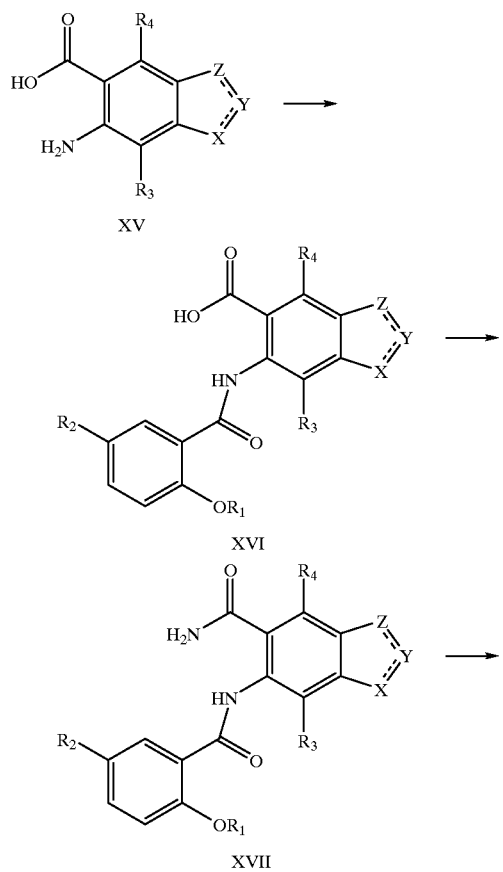

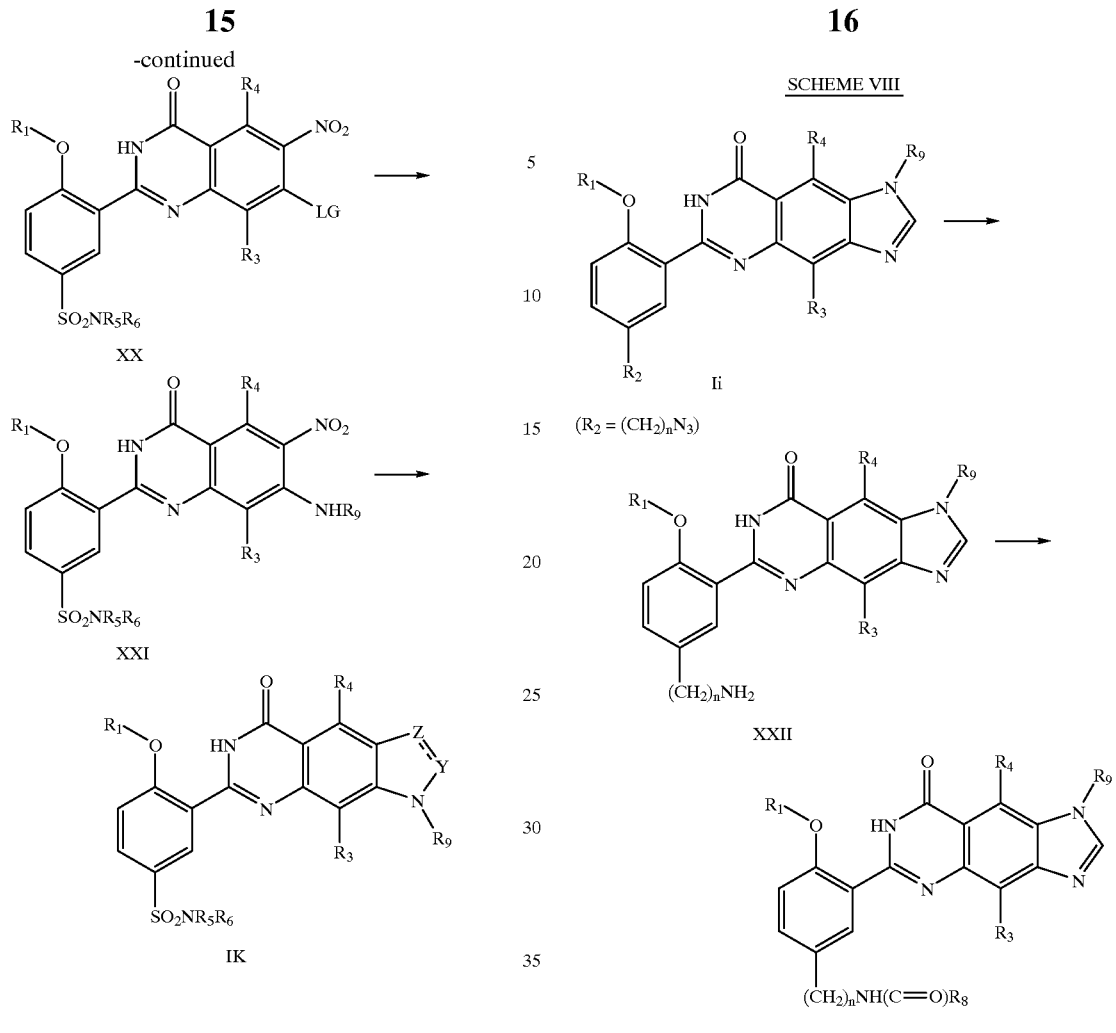

SCHEME VIII

Compounds of formula Ik can be prepared as shown in Scheme VII. Cyclization of compounds of formula XXI in the presence of a formic acid source and a catalyst in an inert solvent at elevated temperature leads to compounds of formula Ik. Exemplary formic acid sources include formic acid, which can also serve as an exemplary solvent. Exemplary catalysts include 10% palladium on carbon.

Compounds of formula XXI can be synthesized from compounds of formula XX using methods similar to those described in Scheme I.

The preparation of compounds of formula XX from compounds of formula XIX can be accomplished using methods described in Scheme III.

The preparation of compounds of formula XIX from compounds of formula XVIII can also be carried out using methods analogous to those described in Scheme III.

Compounds of formula XVIII can be prepared using methods analogous to those described in Scheme I.

Compounds of formula Il can be obtained as described in Scheme VIII. Acylation of compounds of formula XXII can be carried out using carboxylic acids ($R_8CO_2H$) as described in Scheme IV. Compounds of formula XXII can be prepared by reduction of compounds of formula Ii using a hydrogen source and an appropriate catalyst in an inert solvent. Hydrogen gas is an appropriate hydrogen source. Platinum oxide is an appropriate catalyst and ethanol is an appropriate inert solvent. Compounds of formula Ii can be prepared as described in Scheme V.

Utility

The compounds of the present invention inhibit cGMP PDE, and in particular are potent and selective inhibitors of cGMP PDE V. The present compounds are useful in the treatment of cGMP-associated conditions. A "cGMP-associated condition", as used herein, denotes a disorder which can be treated by inhibiting cGMP PDE or elevating the level of cGMP in a subject, wherein treatment comprises prevention, partial alleviation or cure of the disorder. Inhibition of cGMP PDE or elevation of the cGMP level may occur locally, for example, within certain tissues of the subject, or more extensively throughout a subject being treated for such a disorder. Treatment may be facilitated wherein elevation of the cGMP level potentiates additional beneficial therapeutic effects, such as where elevation of the cGMP level potentiates the effects of endothelium-derived relaxing factor.

The compounds of the present invention are useful for the treatment of a variety of cardiovascular diseases including, but not limited to, hypertension, angina (stable, unstable, and variant), (congestive) heart failure, restenosis, atherosclerosis, and dyslipidemia, as well as reduced blood vessel patency, thrombus, both venous and arterial, myocardial infarction, peripheral vascular disease, stroke, bronchitis, chronic asthma, allergic asthma, allergic rhinitis, glaucoma, diseases characterized by disorders of gut motility, and forms of cancer responsive to the inhibition of cGMP PDE. In addition, these compounds are useful in the treatment of sexual dysfunction in both men (erectile dysfunction, for example, due to diabetes mellitus, spinal cord injury, radical prostatectomy, psychogenic etiology, radiotherapy such as for localized prostate cancer, or any other cause) and women by improving blood flow to the genitalia, especially, the corpus cavernosum.

The present invention thus provides methods for the treatment of cGMP-associated conditions, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

The present invention also provides pharmaceutical compositions comprising at least one of the compounds of the formula I capable of treating a cGMP-associated condition in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to cGMP-associated conditions.

The compounds of the present invention may be employed alone or in combination with each other and/or other suitable therapeutic agents useful in the treatment of cGMP-associated conditions such as other cGMP PDE inhibitors, particularly other cGMP PDE V inhibitors, prostanoids, (α-adrenergic agonists, endothelin antagonists, angiotensin II (especially, subtype $AT_1$) antagonists, angiotensin converting enzyme (ACE) inhibitors, rennin inhibitors, serotonin (5-HT$_{2C}$) agonists, and modulators of the large-conductance calcium-activated potassium (BK) channels.

Exemplary such other therapeutic agents include the following: phentolamine, yohimbine, papaverine, apomorphine, sildenafil (see *Drugs of the Future*, 22, 138–143 (1997)), pyrazolopyrimidinones as described in U.S. Pat. Nos. 5,272,147; 5,250,534; 5,426,107; and 5,346,901, quinazolinones as described in U.S. Pat. No. 5,482,941; AT$_1$ antagonists selected from losartan, irbesartan, valsartan and candesartan; ET$_A$ antagonists selected from bosentan, ABT-627, and those described in U.S. Pat. No. 5,612,359 and U.S. patent application Ser. No. 60/035,832, filed Jan. 30, 1997; PDE V inhibitors selected from imidazoquinazolines (see WO 98/08848), carbazoles (see WO 97/03675, WO 97/03985 and WO 95/19978), imidazopurinones (see WO 97/19947), benzimidazoles (see WO 97/24334), pyrazoloquinolines (see U.S. Pat. No. 5,488,055), anthranilic acid derivatives (see WO 95/18097), fused heterocycles (see WO 98/07430) and thienopyrimidines (see DE 19632423); 5-HT$_{2C}$ agonists selected from indoles (see *J. Med. Chem.*, 40, 2762–2769 (1997), EP 655440 and EP 657426); and modulators of the large-conductance calcium-activated potassium (BK) channels as described in U.S. Pat. Nos. 5,565,483, 5,602,169, 5,869,509 and in WO 98/04135 and WO 98/23273.

The above other therapeutic agents, when employed in combination with the compounds of the present invention, may be used, for example, in those amounts indicated in the Physicians' Desk Reference (PDR) or as otherwise determined by one of ordinary skill in the art.

The following assay can be employed in ascertaining the degree of activity of a compound as a cGMP PDE inhibitor. Compounds described in the following Examples have been tested in this assay, and have shown activity.

PDE Scintillation Proximity Assay Protocol

Sonicated human platelet homogenates are prepared by the method of Seiler, et al. (Seiler, S., Gillespie, E., Arnold, A. J., Brassard, C. L., Meanwell, N. A. and Fleming, J. S., "Imidazoquinoline derivatives: potent inhibitors of platelet cAMP phosphodiesterase which elevate cAMP levels and activate protein kinase in platelets," Thrombosis Research, 62: 31–42 (1991)). PDE V is abundant in human platelets, and accounts for approximately 90% of the cGMP hydrolytic activity in the homogenates. When necessary, PDE V can be resolved from other PDE activities in the homogenates by anion exchange chromatography on a fast protein liquid chromatography system (FPLC) using a Mono-Q anion exchange column (Pharmacia) eluted with a linear gradient of 10 mM–450 mM NaCl.

The phosphodiesterase activity is assayed using a commercially available phosphodiesterase [$^3$H]cGMP scintillation proximity (SPA) assay kit (Amersham). The manufacturer's protocol is followed explicitly except that the reactions are carried out at room temperature and 3 mM nonradioactive cGMP is included in the suspension of SPA beads to prevent the synthesis of any additional radioactive products.

All documents cited in the present specification are incorporated herein by reference in their entirety.

The following Examples illustrate embodiments of the present invention, and are not intended to limit the scope of the claims.

Abbreviations

DMF=dimethylformamide
DMSO=dimethylsulfoxide
Et=ethyl
HPLC=high pressure liquid chromatography
LRMS=low resolution mass spectrometry
Me=methyl
MeOH=methanol
mp=melting point
THF=tetrahydrofuran
tlc=thin layer chromatography
HOBt=2-hydroxybenzotriazole
EDAC=1-(3-dimethylaminopropyl)-3-ethylcarbodiimide
TFA=trifluoroacetate
LCMS=liquid chromatography mass spectrometry
DMAP=4-dimethylaminopyridine Preparation of 6,7-diamino2-(2-alkoxyphenyl)-4 (3H)-quinazolinone starting materials The 6,7-diamino-2-(2-alkoxyphenyl)-4(3H)-quinazolinone starting materials used in the synthesis of the compounds of the formula I of the Examples herein were prepared by the methods of Preparations 1 through 5 described following.

Preparation 1

2-Amino-4-chloro-5-nitrobenzamide

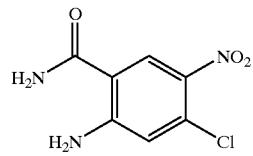

4-Chloroanthranilic acid (10.0 g, 56.5 mmol) was dissolved at room temperature with stirring in 190 mL of distilled water containing 8.98 g (84.7 mmol) Na$_2$CO$_3$. When the 4-chloroanthranilic acid was completely dissolved, a 20% w/v solution of phosgene in toluene (84 mL) was added dropwise via a dropping funnel over 45 minutes. The resulting suspension was stirred at room temperature overnight under nitrogen. The product was collected by filtration and washed well with water. The resulting gray-white solid was dried in a vacuum oven at 60° C. overnight to provide 7-chloro-1,4-dihydro-2H-3,1-benzoxazine-2,4-dione (10.3 g, 52.3 mmol, 93%): $^1$H NMR (DMSO-d$_6$): δ 11.93 (br s, 1H), 7.17 (d, J=1.5 Hz, 1H), 7.28 (dd, J=1.6 and 8.2 Hz, 1H), 7.91 (d, J=8.2 Hz, 1H).

7-Chloro-1,4-dihydro-2H-3,1-benzoxazine-2,4-dione (5.1 g, 25.9 mmol) was added in portions over 40 minutes to a cold (0° C.) solution of concentrated (96–98%) sulfuric acid (15 mL) and concentrated (70%) nitric acid (15 mL). The reaction was stirred at 0° C. for 1 hour, then filtered through a sintered glass funnel. The filtrate was cautiously poured into crushed ice (250 g) to precipitate a yellow-tan solid. This solid was washed well with water and dried overnight in a vacuum oven (60° C.) to furnish 7-chloro-1, 4-dihydro-6-nitro-2H-3,1-benzoxazine-2,4-dione (3.09 g, 12.7 mmol, 49%): $^1$H NMR (DMSO-d$_6$): δ 12.30 (br s, 1H) 7.28 (s, 1H), 8.53 (s, 1H).

7-Chloro-1,4-dihydro-6-nitro-2H-3,1-benzoxazine-2,4-dione (6.5 g, 26.8 mmol) was suspended in glacial acetic acid (70 mL). Ammonium acetate (6.2 g, 80.6 mmol) was added, and the resulting mixture was heated to 100° C. with stirring for 3 hours. After cooling to room temperature, the brown solution was poured into distilled water (200 mL) to precipitate a yellow solid which was collected by filtration and washed well with water and ether. This material was first air dried, then dried overnight under high vacuum to provide 2-amino-4-chloro-5-nitrobenzamide (4.9 g, 23.0 mmol, 86%): $^1$H NMR (DMSO-d6): δ 6.92 (s, 1H), 7.49 (br s, 1H), 7.89 (br s, 2H), 8.22 (br s, 1H), 8.53 (s, 1H).

Preparation 2

General Procedure for Preparation of 2-(2-alkoxybenzoyl)amino-4-chloro-5-nitrobenzamides

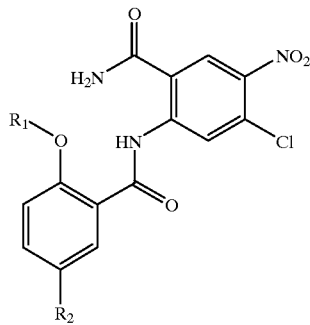

The following general procedure for the coupling of 2-amino-4-chloro-5-nitrobenzamide with aromatic acid chlorides (or active esters) was employed for the preparation of 2-(2-alkoxybenzoyl)amino-4-chloro-5-nitrobenzamides:

2-Amino-4-chloro-5-nitrobenzamide was dissolved in pyridine at room temperature (1 molar equivalent). The appropriate o-alkoxy benzoyl chloride (1.4 molar equivalents) was partially dissolved in a small quantity (<10 mL) of DMF and this mixture was added to the pyridine solution. The resulting brown solution was heated to 80° C. for 2.5 hours. The reaction mixture was cooled to room temperature and poured into distilled water to precipitate a brown solid. This suspension was stirred at room temperature overnight. In the morning, the solid was collected by filtration, washed with water, 10% HCl, and then ether. The product was dried in a vacuum oven. Recrystallization, if necessary, afforded the desired 2-(2-alkoxybenzoylamino)-4-chloro-5-nitrobenzamide. Using this method, the following compounds were prepared:

A. 4-Chloro-2-(2-ethoxybenzoyl)amino-5-nitrobenzamide

Yield: 43% (recrystallized, isopropanol); mp 224–226° C.; NMR (DMSO-d$_6$): δ 12.4 (br s, 1H); 9.04 (s, 1H), 8.54 (br s, 2H), 8.04 (s, 1H), 7.88 (d, J=6.2 Hz, 1H), 7.58 (apparent t, J=6.5 Hz 1H), 7.23 (d, J=6.2 Hz, 1H), 7.10 (apparent t, J=6.2 Hz, 1H).

B. 4-Chloro-2-(2-propoxybenzoyl)amino-5-nitrobenzamide

Yield: 93%; mp 177–178° C.; NMR (DMSO-d$_6$): δ 9.04 (s, 1H), 8.55 (s, 2H), 8.05 (s, 1H), 7.88 (d, J=6.5 Hz, 1H), 7.59 (apparent t, J=6.2 Hz, 1H), 7.23 (d, J32 6.5 Hz, 1H), 7.10 (apparent t, J=6.2 Hz, 1H), 4.19 (t, J=7.2 Hz, 2H), 1.84 (m, 2H), 0.92 (t, J=7.4 Hz, 3H).

C. 4-Chloro-2-(2-Butoxybenzoyl)amino-5-nitrobenzamide

Yield: 61%; mp 219–221° C. NMR (DMSO-d$_6$): δ 9.04 (s, 1H), 8.56 (s, 2H), 8.05 (s, 1H), 7.86 (dd, J=1.8 and 7 Hz, 1H), 7.58 (m, 1H), 7.24 (d, J=8.4 Hz, 1H), 7.10 (m, 1H), 4.23 (t, J=6.7 Hz, 2H), 1.80 (m, 2H), 1.38 (m, 2H); 0.88 (t, J=7.2 Hz, 3H).

PREPARATION 3

General Procedure for Synthesis of 7-chloro-6-nitro-2-(2-alkoxyphenyl)-4(3H)-guinazolinones

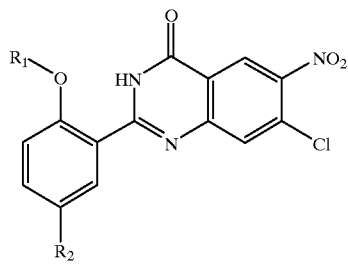

An appropriate 2-(2-alkoxybenzoyl)amino-4-chloro-5-nitrobenzamide was suspended in absolute ethanol (1–1.2 mmol/6–8 mL ethanol), and water was added (½ volume of ethanol). Sodium hydroxide (1.2 equivalents) was then added, followed by 0.5 equivalents of 30% (w/v) aqueous hydrogen peroxide. The reaction mixture was then heated to reflux and the starting material gradually dissolved. When the starting material was consumed as determined by tlc analysis (generally in less than 2 hours), the reaction was cooled to room temperature and concentrated by rotary evaporation to furnish a yellow-brown solid which was washed with water and dried. If necessary, this residue was triturated with ether to provide pure material. Using this method, the following compounds were prepared:

A. 7-Chloro-6-nitro-2-(2-propoxyphenyl)-4(3H)-quinazolinone

Yield: 89%; mp 178–181° C.; NMR (DMSO-d$_6$): δ 8.80 (s, 1H), 8.59 (apparent d, J=8 Hz, 1H), 7.91 (s, 1H), 7.57 (apparent t, J=8 Hz, 1H), 7.19 (apparent t, J=7.4 Hz, 1H), 7.09 (d, J=8 Hz, 1H), 4.24 (t, J=6.5 Hz, 2H), 2.04 (m, 2H), 1.18 (t, J=7.4 Hz, 3H).

B. 2-(2-Butoxyphenyl)-7-chloro-6-nitro-4(3H)-quinazolinone

Yield: 73% (triturated with ether); mp 176–178° C.; LRMS [MH+] 374.

Further substituted 7-chloro-6-nitro-2-(2-alkoxyphenyl)-4(3H)-quinazolinones were prepared as follows.

(i) Preparation of (5-bromo-2-propoxyphenyl)-7-chloro-6-nitro-2-4(3H)-quinazolinone

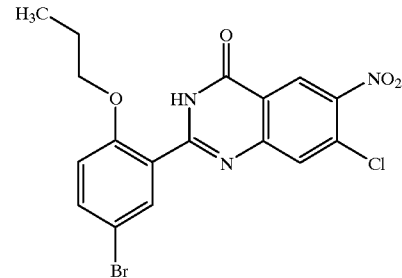

A solution of N-bromosuccinimide (3.56 g, 20 mmol, recrystallized from water prior to use) in DMF (40 mL) was added dropwise to a suspension of 7-chloro-6-nitro-2-(2-propoxyphenyl)-4(3H)-quinazolinone (3.96 g, 10 mmol) in DMF (100 mL) over fifteen minutes. The resulting reaction mixture was heated at 55° C. overnight. The solution was cooled to room temperature and poured into distilled water (500 mL). The precipitated solid was collected by filtration, washed with water and dried first by water aspirator, then under high vacuum to furnish the title compound (4.40 g, 10 mmol): mp 180–184° C.; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 4.77 minutes.

(ii) General procedure for the synthesis of 7-chloro-6-nitro-2-(2-propoxyphenyl)-4(3H)-quinazolinone sulfonamides

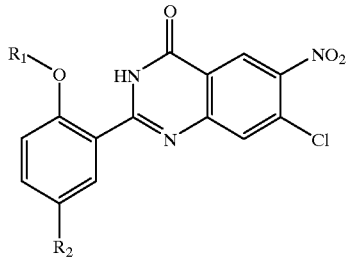

Chlorosulfonic acid (10 mL) was cooled to 0° C. in ice under nitrogen. 7-Chloro-6-nitro-2-(2-propoxyphenyl)-4 (3H)-quinazolinone (2 to 4 mmol) was added portionwise over 20–30 minutes. The reaction was stirred at 0° C. for six hours then, very cautiously, poured slowly into crushed ice. The resulting yellow precipitate was collected by filtration, washed thoroughly with water and sucked dry with a water aspirator. This material was used without further purification for sulfonamide formation.

The resulting sulfonyl chloride was partially dissolved in methylene chloride or isopropanol and 1.5 equivalents of triethylamine were added. This was followed by 1.2 equivalents of the appropriate amine. The reaction mixture was stirred at room temperature for 2–4 hours. If the reaction was carried out in methylene chloride, the reaction was diluted with additional methylene chloride then washed twice with water, dried over magnesium sulfate and concentrated to furnish the product as a yellow solid. If the reaction was carried out in isopropanol, the mixture was concentrated to dryness by rotary evaporation, then partitioned between ethyl acetate and water. The organic layer was washed twice more with water, then brine. After drying with magnesium sulfate, the solution was concentrated to afford a yellow solid which in some cases required purification by flash chromatography over silica gel to afford the appropriate 7-chloro-6-nitro-2-(2-propoxyphenyl)-4(3H)-quinazolinone sulfonamide. Using the above described procedure, the following compounds were prepared:

A. 1-[[3-(7-Chloro-3,4-dihydro-6-nitro-4-oxo-2-quinazolinyl)-4-propoxyphenyl]sulfonyl]-4-methylpiperazine Yield: 72%; mp 225–228° C.; LRMS [MH+] 522; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.46 minutes.

B. 1-[[3-(7-Chloro-3,4-dihydro-6-nitro-4-oxo-2-quinazolinyl)-4-propoxyphenyl]sulfonyl]-4-piperidinecarboxylic acid ethyl ester Yield: 71%; mp 203–204° C.; LRMS [MH+] 579; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 4.41 minutes.

C. 1-[[3-(7-Chloro-3,4-dihydro-6-nitro-4-oxo-2-quinazolinyl)-4-propoxyphenyl]sulfonyl]-3-piperidinecarboxylic acid ethyl ester Yield: 53%; mp 196–197° C.; LRMS [MH+] 579; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 4.35 minutes.

D. 3-(7-Chloro-3,4-dihydro-6-nitro-4-oxo-2-quinazolinyl)-N-(2-1H-imidazol-4-ylethyl)-4-propoxybenzenesulfonamide Yield: 39%; mp 140–144° C.; LRMS [MH+] 533; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.40 minutes.

E. 3-(7-Chloro-3,4-dihydro-6-nitro-4-oxo-2-quinazolinyl)-N-(1H-indazol-5-yl)-4-propoxybenzenesulfonamide Yield: 40%; mp 261–263° C.; LRMS [MH+] 553; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.94 minutes.

F. 1-[[3-(7-Chloro-3,4-dihydro-6-nitro-4-oxo-2-quinazolinyl)-4-propoxyphenyl]sulfonyl]-4-(phenylmethyl)piperazine Yield: 75%; mp 198–200° C.; LRMS [MH+] 596; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.77 minutes.

G. 3-(7-Chloro-3,4-dihydro-6-nitro-4-oxo-2-quinazolinyl)-4-propoxy-N-(4-pyridinylmethyl)benzenesulfonamide Yield: 45%, 194–197° C.; LRMS [MH+] 596; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.61 minutes.

H. 3-(7-Chloro-3,4-dihydro-6-nitro-4-oxo-2-quinazolinyl)-N-[2-(dimethylamino)ethyl]-4-propoxybenzenesulfonamide Yield: 64%, 202–204° C.; LRMS [MH+] 510; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.55 minutes.

I. 1-[[3-(7-Chloro-3,4-dihydro-6-nitro-4-oxo-2-quinazolinyl)-4-propoxyphenyl]sulfonyl]-4-ethylpiperazine Yield: 30%; mp 239–241° C.; LRMS [MH+] 536; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.52 minutes.

J. 4-Acetyl-1-[[3-(7-Chloro-3,4-dihydro-6-nitro-4-oxo-2-quinazolinyl)-4-propoxyphenyl]sulfonyl]-piperazine Yield: 59%; mp 215–217° C.; LRMS [MH+] 550; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.68 minutes.

K. 1-[[3-(7-Chloro-3,4-dihydro-6-nitro-4-oxo-2-quinazolinyl)-4-butoxyphenyl]sulfonyl]-4-methylpiperazine Prepared using the above method for preparing 1-[[3-(7-chloro-3,4-dihydro-6-nitro-4-oxo-2-quinazolinyl)-4-propoxyphenyl]sulfonyl]-4-methylpiperazine, starting with 2-(2-butoxyphenyl)-7-chloro-6-nitro-4(3H)-quinazoline.

Yield: 68%; LRMS [MH+] 536.2; HPLC (YMC S5 ODS 4.6×50 mm column, 4 minute gradient-0% B to 100% B, 4 mL/min flow, solvent A: 10% MeOH-90% H$_2$O-0.2%

H₃PO₄, solvent B: 90% MeOH-10% H₂O-0.2% H₃PO₄) retention time 3.71 minutes.

L. 1-[[3-(7-Chloro-3,4-dihydro-6-nitro-4-oxo-2-quinazolinyl)-4-propoxyphenyl]sulfonyl]-1-piperazine acetic acid ethyl ester Yield: 50%; mp 176–179° C.; LRMS [MH+] 594; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 3.81 minutes.

M. 1-[[3-(7-Chloro-3,4-dihydro-6-nitro-4-oxo-2-quinazolinyl)-4-propoxyphenyl]sulfonyl]-1-ethyl-2-piperazine carboxylic acid ethyl ester Yield: 45%; mp 195–197° C.; LRMS [MH+] 608; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 3.87 minutes.

PREPARATION 4

Procedures for the Synthesis of 7-amino-2-(2-alkoxyphenyl)-6-nitro-4(3H)-quinazolinones (i) The following describes a general method used for the preparation of 7-amino-2-(2-alkoxyphenyl)-6-nitro-4(3H)-quinazolinones directly from 4-chloro-2-(2-alkoxybenzoyl)amino-5-nitrobenzamides (see Preparation 2).

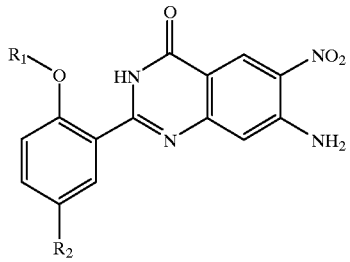

The appropriate 4-chloro-2-(2-alkoxybenzoyl)amino-5-nitrobenzamide was suspended in equal volumes of absolute ethanol and 28% aqueous ammonium hydroxide in a pressure bottle with a stirring bar. After the bottled was tightly sealed, the contents were heated at 140° C. overnight. The reaction mixture was cooled to room temperature, and the resulting suspension was diluted with water. The resulting mixture was filtered to afford a bright yellow solid. This solid was washed with water, then ethanol, and then ether to provide the appropriate 7-amino-2-(2-alkoxyphenyl)-6-nitro-4(3H)-quinazolinone. Using the above described procedure, the following compounds were prepared:

A. 7-Amino-6-nitro-2-(2-ethoxyphenyl)-4(3H)-quinazolinone

Yield: 92%, LRMS [MH+] 327; NMR (270 MHz, DMSO d₆): δ 11.77 (s, 1H), 8.74 (s, 1H), 7.70–7.77, (m, 3H), 7.50 (apparent t, J=7 Hz, 1H), 7.02–7.18 (m, 3H), 4.15 (q, J=7.9 and 13.5 Hz, 2H), 1.34 (t, J=7.9 Hz, 3H).

B. 7-Amino-6-nitro-2-(2-propoxyphenyl)-4(3H)-quinazolinone

Yield: 93%; NMR (400 MHz, DMSO d₆): δ 8.74 (s, 1H), 7.61–7.75 (m, 3H), 7.52 (t, J=7.7 Hz, 1H), 7.18 (d, J=8.4 Hz, 1H), 7.06–7.10 (m, 3H), 4.05 (t, J=6.2 Hz, 2H); 1.71–1.76 (m, 2H), 0.96 (t, J=7.3 Hz, 3H); HPLC (YMC S5 ODS 4.6×50 mm column, 8 minute gradient-0% B to 100% B, 2.5 mL/min flow, solvent A: 10% MeOH-90% H₂O-0.2% H₃PO₄, solvent B: 90% MeOH-10% H₂O-0.2% H₃PO₄) retention time 7.01 minutes.

(ii) The following describes a general method for the preparation of 7-amino-2-(2-alkoxyphenyl)-6-nitro-4(3H)-quinazolinones from 7-chloro-6-nitro-2-(2-alkoxyphenyl)-4(3H)-quinazolinones (see Preparation 3).

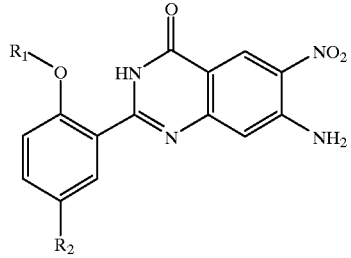

The appropriate 7-chloro-6-nitro-2-(2-alkoxyphenyl)-4(3H)-quinazolinone was suspended in a 2M solution of ammonia in ethanol with a stirring bar in a pressure tube. The tube was sealed and placed in an oil bath heated to 140° C. overnight. The reaction was cooled to room temperature and the precipitated product was collected by filtration, washed with ethanol and ether, and then dried under high vacuum. Using the above described procedure the following 7-amino-6-nitro-2-(2-alkoxyphenyl)-4(3H)-quinazolinones were prepared:

A. 1-[[3-(7-Amino-3,4-dihydro-6-nitro-4-oxo-2-quinazolinyl)-4-propoxyphenyl]sulfonyl]-4-methylpiperazine Yield: 72%; mp 270–271° C.; LRMS [MH+] 503; HPLC (YMC S5 ODS 4.6×50 mm column, 8 minute gradient-0% B to 100% B, 2.5 mL/min flow, solvent A: 10% MeOH-90% H₂O-0.2% H₃PO₄, solvent B: 90% MeOH-10% H₂O-0.2% H₃PO₄) retention time 5.40 minutes.

B. 1-[[3-(7-Amino-3,4-dihydro-6-nitro-4-oxo-2-quinazolinyl)-4-propoxyphenyl]sulfonyl]-4-piperidinecarboxylic acid ethyl ester Yield: 58%; mp 247–249° C.; LRMS [MH+] 560.

C. 1-[[3-(7-Amino-3,4-dihydro-6-nitro-4-oxo-2-quinazolinyl)-4-propoxyphenyl]sulfonyl]-3-piperidinecarboxylic acid ethyl ester Yield: 52%; mp 219–220° C.; LRMS [MH+] 560.

D. 3-(7-Amino-3,4-dihydro-6-nitro-4-oxo-2-quinazolinyl)-N-(2-1H-imidazol-4-ylethyl)-4-propoxybenzenesulfonamide Yield: 46%; mp 169–172° C.; LRMS [MH+] 514; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 2.91 minutes.

E. 3-(7-Amino-3,4-dihydro-6-nitro-4-oxo-2-quinazolinyl)-N-(1H-indazol-5-yl)-4-propoxybenzenesulfonamide Yield: 32%; mp 261–263° C.; LRMS [MH+] 536; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 3.42 minutes.

F. 1-[[3-(7-Amino-3,4-dihydro-6-nitro-4-oxo-2-quinazolinyl)-4-propoxyphenyl]sulfonyl]-4-(phenylmethyl)piperazine Yield: 31%, mp 198–200° C.; LRMS [MH+] 579; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 3.77 minutes.

G. 3-(7-Amino-3,4-dihydro-6-nitro-4-oxo-2-quinazolinyl)-4-propoxy-N-(4-pyridinylmethyl)benzenesulfonamide Yield: 48%, mp 157–160° C., LRMS [MH+] 482; HPLC (YMC S5 ODS 4.6×50 mm column, 4 minute gradient-0% B to 100% B, 4 mL/min flow, solvent A: 10% MeOH-90% $H_2O$-0.2% $H_3PO4$, solvent B: 90% MeOH-10% $H_2O$-0.2% $H_3PO_4$) retention time 2.05 minutes.

H. 3-(7-Amino-3,4-dihydro-6-nitro-4-oxo-2-quinazolinyl)-N-[2-(dimethylamino)ethyl]-4-propoxybenzenesulfonamide Yield: 56%, 202–204° C.; LRMS [MH+] 491; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.89 minutes.

I. 7-Amino-6-nitro-2-(5-bromo-2-propoxyphenyl)-4(3H)-quinazolinone

Yield: 79%; mp 262–263° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 4.05 minutes.

J. 1-[[3-(7-Amino-3,4-dihydro-6-nitro-4-oxo-2-quinazolinyl)-4-butoxyphenyl]sulfonyl]-4-methylpiperazine Yield: 60%, mp 265–267° C., LRMS [MH+] 517

K. 1-[[3-(7-Amino-3,4-dihydro-6-nitro-4-oxo-2-quinazolinyl)-4-propoxyphenyl]sulfonyl]-4-ethylpiperazine Yield: 78%, mp 248–250° C.; LRMS [MH+] 517; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.07 minutes.

L. 4-Acetyl-1-[[3-(7-amino-3,4-dihydro-6-nitro-4-oxo-2-quinazolinyl)-4-propoxyphenyl]sulfonyl]-piperazine Yield: 52%; mp 249–251° C.; LRMS [MH+] 531; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.46 minutes.

M. 1-[[3-(7-Amino-3,4-dihydro-6-nitro-4-oxo-2-quinazolinyl)-4-propoxyphenyl]sulfonyl]-1-piperazine acetic acid ethyl ester Yield: 56%; mp 271–273° C.; LRMS [MH+] 575; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.20 minutes.

N. 1-[[3-(7-Amino-3,4-dihydro-6-nitro-4-oxo-2-quinazolinyl)-4-propoxyphenyl]sulfonyl]-1-ethyl-2-piperazine carboxylic acid ethyl ester Yield: 38%; mp 213–215° C.; LRMS [MH+] 589; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.29 minutes.

PREPARATION 5

The following describe methods for the preparation of 6,7-diamino-2-(2-alkoxyphenyl)-4(3H)-quinazolinones.

(i) 2-(5-Bromo-2-propoxyphenyl)-6,7-diamino-4(3H)-quinazolinone

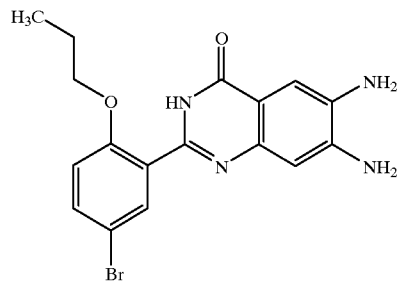

7-Amino-2-(5-bromo-2-propoxyphenyl)-6-nitro-4(3H)-quinazolinone (0.500 g, 1.19 mmol) was dissolved in a mixture of absolute ethanol (20 mL) and ethyl acetate (30 mL). Tin(II) chloride (1.36 g, 7.14 mmol) was then added. The resulting reaction mixture was heated to 70° C. overnight. After cooling to room temperature, the mixture was poured into 300 mL saturated sodium bicarbonate. The solid that precipitated was collected by filtration, washed with water and dried. The resulting solid was triturated with methylene chloride and undissolved solids were removed by filtration. The solution was concentrated to provide the title compound as a tan solid (0.410 g, 1.05 mmol, 88%): mp dec>170° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.04 minutes.

(ii) 1-[[3-(6,7-Diamino-3,4-dihydro-4-oxo-2-quinazolinyl)-4-propoxyphenyl]sulfonyl]-4-(phenylmethyl)piperazine

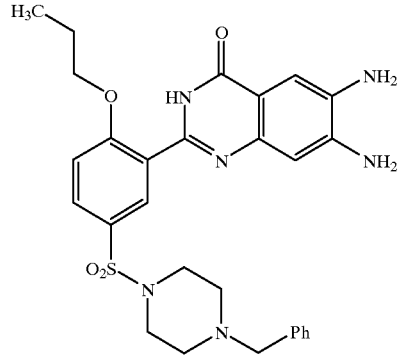

A mixture of 1-[[3-(7-amino-3,4-dihydro-6-nitro-4-oxo-2-quinazolinyl)-4-propoxyphenyl]sulfonyl]-4-phenylmethylpiperazine (0.12 g, 0.21 mmol) and platinum (II) oxide (0.05 g) in methanol (40 mL) was shaken under a hydrogen atmosphere (30 psi) overnight. The resulting mixture was filtered to afford the title compound as a yellow solid (0.075 g, 0.14 mmol, Yield: 67%); mp 158–163° C.; LRMS [MH+] 549; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.37 minutes.

(iii) General procedures for reduction of 7-amino-2-(2-alkoxyphenyl)-6-nitro-4(3H)-quinazolinones to 6,7-diamino-2-(2-alkoxyphenyl)-4(3H)-quinazolinones

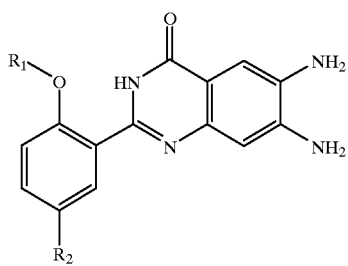

Method 1: When $R_2$ contains no basic nitrogen.

The appropriate 7-amino-6-nitro-2-(2-alkoxyphenyl)-4(3H)-quinazolinone was added to a suspension of 10% palladium on charcoal (30% by weight) in absolute ethanol in a Parr bottle. The mixture was hydrogenated on a Parr shaker at room temperature under 40 psi $H_2$ overnight. The suspension was filtered through Celite and the cake washed well with ethanol. The filtrate was evaporated to provide the appropriate 6,7-diamino-2-(2-alkoxyphenyl)-4(3H)-quinazolinone.

Method 2: When $R_2$ contains a basic nitrogen.

The appropriate 7-amino-6-nitro-2-(2-alkoxyphenyl)-4(3H)-quinazolinone was partially dissolved in 5–10% aqueous HCl and added to a suspension of 10% palladium on charcoal in absolute ethanol (50% by weight) in a Parr bottle. The mixture was hydrogenated on a Parr shaker at room temperature under 40 psi $H_2$ overnight. The suspension was filtered through Celite and the cake washed well with ethanol. The filtrate was evaporated to provide the appropriate 6,7-diamino-2-(2-alkoxyphenyl)-4(3H)-quinazolinone as the hydrochloride salt. Using the above described procedures, the following compounds were prepared:

A. 6,7-Diamino-2-(2-ethoxyphenyl)-4(3H)-quinazolinone

Method 1 was used. Yield: 81%; LRMS [MH+] 296; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.13 minutes.

B. 6,7-Diamino-2-(2-propoxyphenyl)-4(3H)-quinazolinone

Method 1 was used. Yield: 82%, mp 195–197° C., HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.38 minutes.

C. 1-[[3-(6,7-Diamino-3,4-dihydro-4-oxo-2-quinazolinyl)-4-propoxyphenyl]sulfonyl]-4-methylpiperazine Method 2 was used to afford the hydrochloride salt of the title compound. Yield: 50%; LRMS [MH+] 473; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 3.65 minutes.

D. 1-[[3-(6,7-Diamino-3,4-dihydro-4-oxo-2-quinazolinyl)-4-butoxyphenyl]sulfonyl]-4-methylpiperazine Method 2 was used to afford the hydrochloride salt of the title compound. Yield: 78%; mp dec>270° C.; LRMS [MH+] 487; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.53 minutes.

E. 1-[[3-(6,7-Diamino-3,4-dihydro-4-oxo-2-quinazolinyl)-4-propoxyphenyl]sulfonyl]-4-piperidinecarboxylic acid ethyl ester Method 1 was used. Yield: 67%; mp 197–199° C.; LRMS [MH+] 530; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.06 minutes.

F. 1-[[3-(6,7-Diamino-3,4-dihydro-4-oxo-2-quinazolinyl)-4-propoxyphenyl]sulfonyl]-3-piperidinecarboxylic acid ethyl ester Method 1 was used. Yield: 52%; mp 219–220° C.; LRMS [MH+] 530.

G. 3-(6,7-Diamino-3,4-dihydro-4-oxo-2-quinazolinyl)-N-(2-1H-imidazol-4-ylethyl)-4-propoxybenzenesulfonamide Method 2 was used to afford the hydrochloride salt of the title compound. Yield: 46%; mp 169–172° C.; LRMS [MH+] 514; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 1.97 minutes.

H. 3-(6,7-Diamino-3,4-dihydro-4-oxo-2-quinazolinyl)-N-(1H-indazol-5-yl)-4-propoxybenzenesulfonamide Method 1 was used. Yield: 32%; mp 261–263° C.; LRMS [MH+] 536; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.42 minutes.

I. 3-(6,7-Diamino-3,4-dihydro-4-oxo-2-quinazolinyl)-N-(4-pyridylmethyl)-4-propoxybenzenesulfonamide Method 1 was used. Yield: 61%, mp 157–160° C., HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.05 minutes.

J. 3-(6,7-Diamino-3,4-dihydro-4-oxo-2-quinazolinyl)-N-(2-dimethylaminoethyl)-4-propoxybenzenesulfonamide Method 1 was used. Yield: 56%; mp 202–204° C.; LRMS [MH+] 491; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.89 minutes.

K. 1-[[3-(6,7-Diamino-3,4-dihydro-4-oxo-2-quinazolinyl)-4-propoxyphenyl]sulfonyl]-4-ethylpiperazine Method 1 was used. Yield 70%; mp 183–186° C.; LRMS [MH+] 487; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.15 minutes.

L. 4-Acetyl-1-[[(6,7-Diamino-3,4-dihydro-4-oxo-2-quinazolinyl)-4-propoxyphenyl]sulfonyl]-piperazine Method 1 was used. Yield 49%; mp 177–180° C.; LRMS [MH+] 501; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.49 minutes.

Preparation of 5-Amino-1-[(phenylmethyl)amino]-1H-benzimidazole-6-arboxamides

The 5-amino-1-[(phenylmethyl)amino]-1H-benzimidazole-6-carboxamides used in the synthesis of the compounds of formula I of the Examples herein were prepared by the methods of Preparations 6 to 9 described following.

PREPARATION 6

2,4-Dinitro-5-chlorobenzoic Acid

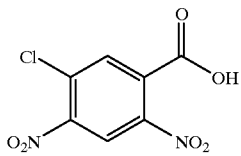

3-Chlorobenzoic acid (12.5 g, 80 mmol) was dissolved in 145 mL of concentrated sulfuric acid with stirring, while warming to 40° C. Potassium nitrate (8.0 g, 78 mmol) was added in divided portions over 30 minutes. The reaction mixture was then warmed to 100° C. and an additional 14 g of potassium nitrate was added over 20 minutes. The reaction mixture was warmed to 145° C. and held at this temperature for 15 minutes. The reaction was cooled to room temperature and poured into 1 kg of ice to precipitate a faintly yellow solid. This material was collected by filtration and washed with water. The resulting solid was then suspended in 500 mL distilled water and stirred at room temperature for 45 minutes. The undissolved solid was collected by filtration and dried under high vacuum to obtain 8.9 g (36%) yield of product as a faintly yellow solid. NMR (400 MHz; acetone-$d_6$): δ 8.76, s 1H, 8.26, s 1H; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.32 minutes.

PREPARATION 7

2,4-Dinitro-5-chlorobenzamide

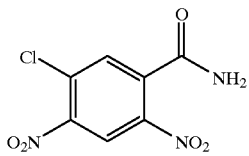

2,4-Dinitro-5-chlorobenzoic acid (7.00 g, 28.4 mmol) was suspended in 40 mL thionyl chloride containing 3 drops of DMF. The suspension was warmed to reflux for four hours. After cooling to room temperature, solvent was removed by rotary evaporation leaving a golden yellow liquid. This was diluted with 30 mL acetone and added dropwise over 20 minutes to a 0° C. solution of 20 mL concentrated ammonium hydroxide. The reaction was stirred at 0° C. for 30 minutes, then poured into 250 g of ice. The yellow orange precipitate was collected by filtration and washed well with water. The solid was dried first by water aspirator then under high vacuum to furnish 5.9 g (24 mmol, 84% yield) of product. NMR (400 MHz; acetone-$d_6$): δ 8.75, s 1H, 8.25, s 1H; mp 201–203° C.

PREPARATION 8

5-Benzylamino-2,4-dinitrobenzamides

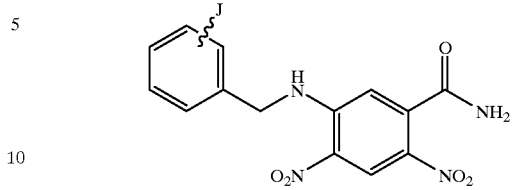

The following describes a general method for the synthesis of 5-benzylamino-2,4-dinitrobenzamides (J=H, F, Cl, CN, methoxy for 8A to 8L below):

2,4-Dinitro-5-chlorobenzamide (0.50 g–3.5 g) was suspended in 15–70 mL THF and 1.2 equivalents of triethylamine was added, followed by 1.2 equivalents of the appropriate benzylamine. The reaction was heated to reflux until tlc indicated starting material had been consumed. The cooled reaction mixture was filtered and the filtrate was concentrated in vacuo leaving a solid which was triturated with ether. This solid was collected by filtration, washed with ether and dried affording the product.

A. 5-(Phenylmethyl)amino-2,4-dinitrobenzamide

84% yield, mp 143–146° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.00 minutes.

B. 5-[[(4-Fluorophenyl)methyl]amino]-2,4-dinitrobenzamide

81% yield; mp 178–180° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.98 minutes.

C. 5-[[(3-Fluorophenyl)methyl]amino]-2,4-dinitrobenzamide

90% yield; mp 175–177° C.; LRMS [MH+] 335; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.92 minutes.

D. 5-[[(3-Methoxyphenyl)methyl]amino]-2,4-dinitrobenzamide

68% yield; mp 222–224° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.97 minutes.

E. 5-[[(2-Methoxyphenyl)methyl]amino]-2,4-dinitrobenzamide

86% yield; mp 198–202° C.; HPLC (YMC S5 ODS 4.6×50 mm column, 4 minute gradient-0% B to 100% B, 4 mL/min flow, solvent A: 10% MeOH- 90% $H_2O$-0.2% $H_3PO_4$, solvent B: 90% MeOH-10% $H_2O$-0.2% $H_3PO_4$) retention time 3.12 minutes.

F. 5-[[(3-Chlorophenyl)methyl]amino]-2,4-dinitrobenzamide

81% yield; mp 178–180° C.; LRMS [MH+] 349; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.22 minutes.

G. 5-[[(2-Chlorophenyl)methyl]amino]-2,4-dinitrobenzamide

69% yield; mp 158–161° C.; LRMS [MH+] 349 HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 3.26 minutes.

H. 5-[[(3-Chloro-4-methoxyphenyl)methyl]amino]-2,4-dinitrobenzamide

100% yield; mp 180–182° C.; HPLC (YMC S5 ODS 4.6×50 mm column, 4 minute gradient 0% B to 100% B, 4 ml/min flow, solvent A: 10% MeOH-90% H₂O-0.2% H₃PO₄, solvent B 90% MeOH-10% H₂O-0.2% H₃PO₄) retention time 3.16 minutes.

I. 5-[[(3-Cyanophenyl)methyl]amino]-2,4-dinitrobenzamide

95% yield; mp 228–230° C.; HPLC (YMC S5 ODS 4.6×50 mm column, 4 minute gradient 0% B to 100% B, 4 m/min flow, solvent A: 10% MeOH-90% H₂O-0.2% H₃PO₄, solvent B 90% MeOH-10% H₂O-0.2% H₃PO₄) retention time 2.55 minutes.

J. 5-[[(4-Cyanophenyl)methyl]amino]-2,4-dinitrobenzamide

74% yield; mp 201–203° C.; HPLC (YMC S5 ODS 4.6×50 mm column, 4 minute gradient 0% B to 100% B, 4 ml/min flow, solvent A: 10% MeOH-90% H₂O-0.2% H₃PO₄, solvent B 90% MeOH-10% H₂O-0.2% H₃PO₄) retention time 2.57 minutes.

K. 5-[[(4-Chlorophenyl)methyl]amino]-2,4-dinitrobenzamide

100% yield; mp 207–210° C.; HPLC (YMC S5 ODS 4.6×50 mm column, 4 minute gradient 0% B to 100% B, 4 ml/min flow, solvent A: 10% MeOH-90% H₂O-0.2% H₃PO₄, solvent B 90% MeOH-10% H₂O-0.2% H₃PO₄) retention time 3.36 minutes.

L. 5-[[(4-Methoxyphenyl)methyl]amino]-2,4-dinitrobenzamide

100% yield; mp 201–203° C.; HPLC (YMC S5 ODS 4.6×50 mm column, 4 minute gradient 0% B to 100% B, 4 ml/min flow, solvent A: 10% MeOH-90% H₂O-0.2% H₃PO₄, solvent B 90% MeOH-10% H₂O-0.2% H₃PO4) retention time 3.09 minutes.

PREPARATION 9

5-Amino-1-[(phenylmethyl)amino]-1H-benzimidazole-6-carboxamides

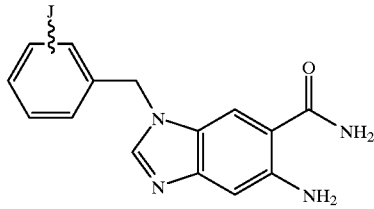

The following describes a general method for the synthesis of 5-amino-[(phenylmethyl)amino]-1H-benzimidazole-6-carboxamides (J=H, F, Cl, CN, methoxy for 9A to 9L below):

The appropriate 5-benzylamino-2,4-dinitrobenzamide from Preparation 8 (0.50 g–3.5 g) was partially dissolved in methanol (20 mL–200 mL) containing 25% by weight platinum oxide. Hydrogen was introduced using a balloon and the flask was evacuated and filled several times before leaving the suspension stirring under an atmosphere of hydrogen at room temperature. The mixture was stirred until HPLC analysis showed consumption of starting material and conversion to the desired diamine product (typically 5 hours). The suspension was filtered through Celite and the filter cake was washed with methanol. The filtrate was concentrated to furnish the crude diamine. This material was then dissolved in concentrated (96%) formic acid and stirred at room temperature overnight. Formic acid was removed at room temperature under vacuum, leaving a brown solid. This material was dissolved in absolute ethanol (10–50 mL) and 10% aqueous HCl (3–10 mL) and stirred at room temperature for three hours. Solvent was removed by rotary evaporation to furnish the product as the hydrochloride salt. This material was sufficiently pure for further transformation. The yield stated is the net for this three step sequence.

A. 5-Amino-[(phenylmethyl)amino]-1H-benzimidazole-6-carboxamide yield: 90%; LRMS [MH+] 267; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 1.52 minutes.

B. 5-Amino-1-[[(4-fluorophenyl)methyl]amino]-1H-benzimidazole-6-carboxamide yield 93%; LRMS [MH+] 286; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 1.53 minutes.

C. 5-Amino-1-[[(3-fluorophenyl)methyl]amino]-1H-benzimidazole-6-carboxamide yield: 100%; LRMS [MH+] 285; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 1.56 minutes.

D. 5-Amino-1-[[(3-methoxyphenyl)methyl]amino]-1H-benzimidazole-6-carboxamide yield: 94%; LRMS [MH+] 297; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 1.70 minutes.

E. 5-Amino-1-[[(2-methoxyphenyl)methyl]amino]-1H-benzimidazole-6-carboxamide yield: 87%; LRMS [MH+] 297; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 1.83 minutes.

F. 5-Amino-1-[[(3-chlorophenyl)methyl]amino]-1H-benzimidazole-6-carboxamide yield: 80%; LRMS [MH+] 301; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 1.87 minutes.

G. 5-Amino-1-[[(2-chlorophenyl)methyl]amino]-1H-benzimidazole-6-carboxamide yield: 100%; LRMS [MH+] 301; HPLC (YMC S5 ODS 4.6×50 mm column, 4 minute gradient-0% B to 100% B, 4 ml/min flow, solvent A: 10% MeOH-90% H₂O-0.2% H₃PO₄, solvent B: 90% MeOH-10% H₂O-0.2% H₃PO₄) retention time 2.00 minutes.

H. 5-Amino-1-[[(3-Chloro-4-methoxyphenyl)methyl]amino]-1H-benzimidazole-6-carboxamide 100% yield; LRMS [M+H] 301; HPLC (YMC S5 ODS 4.6×50 mm column, 4 minute gradient 0% B to 100% B, 4 ml/min flow, solvent A: 10% MeOH-90% H₂O-0.2%

$H_3PO_4$, solvent B 90% MeOH-10% $H_2O$-0.2% $H_3PO_4$) retention time 1.93 minutes.

I. 5-Amino-1-[[(3-Cyanophenyl)methyl]amino]-1H-benzimidazole-6-carboxamide

73% yield; LRMS [M+H] 293; HPLC (YMC S5 ODS 4.6×50 mm column, 4 minute gradient 0% B to 100% B, 4 ml/min flow, solvent A: 10% MeOH-90% $H_2O$-0.2% $H_3PO_4$, solvent B 90% MeOH-10% $H_2O$-0.2% $H_3PO_4$) retention time 1.07 minutes.

J. 5-Amino-1-[[(4-Cyanophenyl)methyl]amino]-1H-benzimidazole-6-carboxamide

77% yield; LRMS [M+H] 293; HPLC (YMC S5 ODS 4.6×50 mm column, 4 minute gradient 0% B to 100% B, 4 ml/min flow, solvent A: 10% MeOH-90% $H_2O$-0.2% $H_3PO_4$, solvent B 90% MeOH-10% $H_2O$-0.2% $H_3PO_4$) retention time 0.78 minutes.

K. 5-Amino-1-[[(4-Chlorophenyl)methyl]amino]-1H-benzimidazole-6-carboxamide

72% yield; LRMS (M+H) 301; HPLC (YMC S5 ODS 4.6×50 mm column, 4 minute gradient 0% B to 100% B, 4 ml/min flow, solvent A: 10% MeOH-90% $H_2O$-0.2% $H_3PO_4$, solvent B 90% MeOH-10% $H_2O$-0.2% $H_3PO_4$) retention time 2.03 minutes.

L. 5-Amino-1-[[(4-methoxyphenyl)methyl]amino]-1H-benzimidazole-6-carboxamide

47% yield; LRMS (M+H) 297; HPLC (YMC S5 ODS 4.6×50 mm column, 4 minute gradient 0% B to 100% B, 4 ml/min flow, solvent A: 10% MeOH-90% $H_2O$-0.2% $H_3PO_4$, solvent B 90% MeOH-10% $H_2O$-0.2% $H_3PO_4$) retention time 1.65 minutes.

Preparation of Carboxylic Acid Starting Materials

The carboxylic acid starting materials used in the synthesis of the compounds of the formula I in the Examples herein were prepared by the methods of Preparations 10 to 12 described following.

PREPARATION 10

Methyl 4-chlorosulfonyl-2-propoxy benzoic Acid

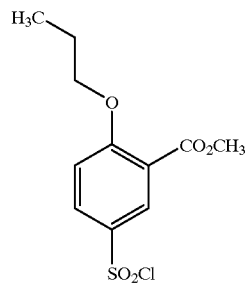

To a solution of methyl salicylate (25 g, 0.16 mol) in 300 mL acetone was added 34 g potassium carbonate (0.25 mol) and 84 g (0.49 mol) 1-iodopropane. The mixture was heated to reflux for 24 hours, then cooled and filtered. The filtrate was concentrated and the residue taken up in 500 mL of ether. The ether solution was washed twice with water and twice with brine, then dried and concentrated to give a faintly yellow oil. This material was a single spot by tlc (1:1 methylene chloride/hexane, $R_f$ 0.4) and was used without further purification.

The crude propoxy ester was added dropwise at 0° C. to a mixture of 35 mL of chlorosulfonic acid and 9.6 mL of thionyl chloride over 30 minutes. The dark red reaction was stirred overnight and was allowed to warm slowly to room temperature. The reaction was cautiously poured over 500 g of ice and stirred to deposit a yellow solid which was recrystallized from cyclohexane to furnish 13 g (0.045 mol, 28% yield) of fine white needles, mp 58–59° C.; $^{13}$C NMR (100 MHz, $CDCl_3$) δ: 164.7, 163.9, 135.6, 132.7, 131.8, 121.5, 113.6, 71.6, 52.9, 22.6, 10.7.

This material was employed for the synthesis of the following sulfonamides using the general procedure outlined in Preparation 11.

PREPARATION 11

The appropriate amine (1.1 equivalents) was dissolved in methylene chloride (5–20 mL) along with 1.3 equivalents of triethylamine and cooled to 0° C. The sulfonyl chloride from Preparation 10 was dissolved in methylene chloride (10–15 mL) and added dropwise over 30 minutes to this solution. The reaction was stirred at 0° C. for 1–1.5 hours, then washed twice with water and twice with brine. The organic solution was dried and concentrated to furnish the following products.

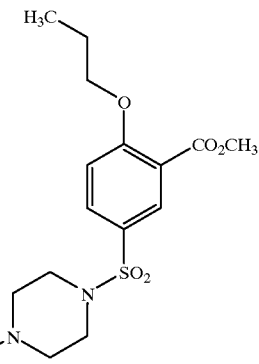

A. 5-[(4-Methyl-4-piperazinyl)sulfonyl]-2-propoxybenzoic acid methyl ester yield: 100%; $^{13}$C NMR (100 MHz, $CDCl_3$) δ: 165.5, 162.2, 133.3, 132.1, 126.7, 121.0, 113.3, 71.2, 54.3, 52.7, 52.6, 46.3, 46.0, 22.7, 10.8; $R_f$ (1:1 acetone/methylene chloride) 0.45.

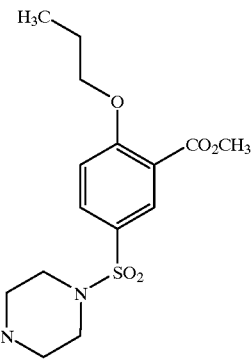

B. 5-[(4-Ethyl-4-piperazinyl)sulfonyl]-2-propoxybenzoic acid methyl ester yield: 99%; LRMS [MH+] 371; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.57 minutes.

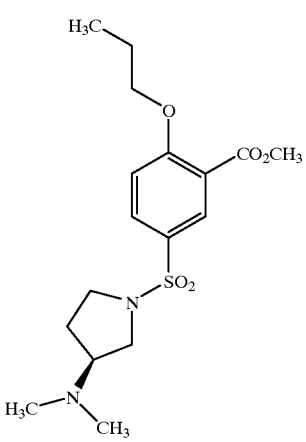

C. (R)-5-[(3-Dimethylamino pyrrolidine)sulfonyl]-2-propoxybenzoic acid methyl ester.

yield: 84%; $^{13}C$ NMR (100 MHz; $CDCl_3$) δ: 165.6, 162.1, 133.1, 131.8, 128.0, 121.0, 113.3, 71.2, 65.3, 52.6, 52.2, 47.3, 44.4, 31.9, 30.3, 23.0, 22.7, 14.5, 10.8.

PREPARATION 12

The following procedure was used for the synthesis of carboxylic acids used in the preparation of compounds of formula I of the present invention:

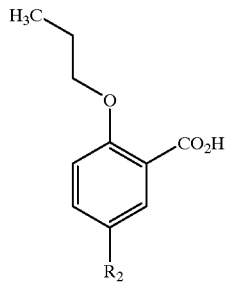

The appropriate methyl ester (from Preparations 10, 11A, 11B and 11C) was dissolved in 40–50 mL THF with 10–15 mL water and one equivalent of LiOH hydrate. The reaction was heated to reflux overnight and solvents were removed by rotary evaporation to furnish a quantitative yield of the lithium salt of the carboxylic acid as a white solid.

A. 5-[(4-Methyl-4-piperazinyl)sulfonyl]-2-propoxybenzoic Acid

HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.14 minutes; $^1H$ NMR (400 Mhz, $D_2O$) δ: 7.62 (1H, dd, J=2.5, 9.1 Hz), 7.57 (1H, d, J=2.5 Hz), 7.09 (1H, d, J=9.1 Hz), 3.97 (2 Hz, t, J=6.5 Hz), 2.89 (4H, br s), 2.38 (4H, br s), 2.06 (3H, s), 1.66 (2H, m), 0.84 (3H, t, J=7.5 Hz).

B. 5-[(4-Ethyl-4-piperazinyl)sulfonyl]-2-propoxybenzoic Acid

HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.13 minutes; LRMS [MH+] 363.

C. 2-Propoxybenzoic Acid $^1H$ NMR (400 MHz, $CDCl_3$) δ:8.19 (1H, dd, J=1.8, 8.0 Hz), 7.55 (1H, apparent t, J=8.0 Hz), 7.13 (1H, t, J=7.5 Hz), 7.05 (1H, d, J=7.5 Hz), 4.23 (2H, t, J=6.6 Hz), 1.96 (2H, m), 1.11 (3H, t, J=7.4 Hz).

D. (R)5-[(3-Dimethylamino pyrrolidine)sulfonyl]-2-propoxybenzoic Acid.

HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.14 minutes; LRMS [MH+] 357.

PREPARATION 13

5-Bromo-2-propoxybenzoic Acid

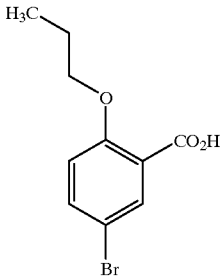

5-Bromo-2-hydroxy-benzoic acid (26.6 gm) was dissolved in 160 mL DMF containing 125 gm 1-iodopropane and 50.8 gm $K_2CO_3$. The reaction mixture was heated to 50° C. overnight. Ether (250 mL) was added to the cooled reaction mixture and the suspended solids were removed by filtration. The solution was washed with water (2×50 mL). The aqueous extract was extracted with 4×50 mL ether. The combined ether extracts were washed with brine, dried ($MgSO_4$) and concentrated by rotary evaporation to afford 38 gm of a pale yellow liquid. HPLC analysis of this material showed ≧95% of a single component with retention time 4.6 minutes (HPLC conditions: YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$).

This material was treated as described in Preparation 12 to furnish the corresponding carboxylic acid of this Preparation as a light yellow solid. HPLC: (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.72 minutes (≧96% pure).

PREPARATION 14

5-(Azidomethyl)-2-propoxybenzoic Acid

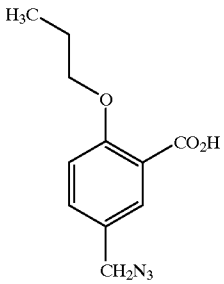

2-Hydroxy-5-formylbenzoic acid (3.00 gm, 18.07 mmol) was dissolved in DMF (30 mL) containing 9.42 gm (55.41 mmol) 1-iodopropane and 6.23 gm (45.18 mmol) potassium carbonate. The reaction mixture was stirred at room temperature for 24 hours then heated to 60° C. for 3.5 hours. Undissolved solids were removed by filtration. The filtrate was diluted with 50 mL water and extracted with 5×25 mL ether. The collected organic layers were washed with 3×30 mL 5% $NaHSO_3$ and brine, then dried and concentrated to provide the crude formyl ester (3.89 gm, 15.56 mmol, 86% yield) which was used without further purification.

This crude product was dissolved in 125 mL absolute ethanol and cooled to 0° C. Sodium borohydride (1 equivalent) was added in one portion. The reaction was stirred at 0° C. for one hour, when the reaction was concentrated under reduced pressure. The liquid residue was partitioned between 10% HCl and 30 mL ether. The aqueous layer was extracted with 4×50 mL more ether and the combined organic extracts were washed twice with brine. The ether layer was dried and concentrated under reduced pressure to provide a faintly yellow oil (2.63 gm, 10.43 mmol, 67% yield) of the desired alcohol which was also used without further purification.

The alcohol obtained above (1.16 gm, 4.60 mmol) was dissolved in 20 mL methylene chloride and cooled to 0° C. in an ice bath. 0.77 mL triethylamine was added, followed by 0.39 mL methanesulfonyl chloride. After 2 hours at 0° C., an additional 0.39 mL of methanesulfonyl chloride and 0.77 mL triethylamine were added and the reaction was warmed to room temperature. After a total of 6.5 hours, the reaction was diluted with 30 mL methylene chloride and washed with 3×20 mL 1M $H_3PO_4$ then twice with brine. The organic layer was dried and concentrated under reduced pressure to afford a yellow liquid which was dissolved in 20 mL DMF. Sodium azide (0.89 gm, 13.80 mmol) was added. The reaction mixture was heated to 70° C. for 1 hour. The reaction was cooled to room temperature, diluted with 50 mL water and extracted with 5×20 mL portions of ether. The collected organic extracts were washed twice with brine, dried and concentrated to furnish a viscous faintly yellow oil (1.13 gm, 4.08 mmol, 88% yield) that was ≧95% pure by $^1H$ NMR. IR (NaCl windows, neat) showed a strong band at 2100 $cm^{-1}$. This material was dissolved in 30 mL THF and 4 mL water containing 0.35 gm (8.33 mmol) $LiOH-H_2O$. The reaction was heated to reflux overnight. The cooled reaction mixture was concentrated under reduced pressure to remove the THF. Water (30 mL) was added and was extracted with 3×30 mL methylene chloride. The aqueous layer was acidified with concentrated HCl to pH 1 (pH paper) and extracted with 5×20 mL ether. The combined ether extracts were washed with brine, dried and concentrated to furnish 0.84 gm of a faintly yellow liquid (3.55 mmol, 91% yield). $^{13}C$ NMR (100 MHz, $CDCl_3$) δ: 165, 157, 134, 133, 129, 117, 113, 71, 53, 22, 10. HPLC: (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.37 minutes; IR (NaCl window, neat) 2100 $cm^{-1}$.

PREPARATION OF COMPOUNDS OF THE FORMULA I OF THE PRESENT INVENTION

EXAMPLES 1 to 15

The compounds of Examples 1 to 15 were prepared by the following general procedure for the cyclization of 6,7-diamino-4(3H)-quinazolinones (see Preparation 5 above) to 1H-imidazo[4,5-g]quinazolin-8(7H)-ones:

The appropriate 6,7-diamino-2-(2-alkoxyphenyl)-4(3H)-quinazolinone was dissolved in concentrated formic acid (0.2 to 0.4 mmol in 5 mL 96% formic acid) and heated to reflux under nitrogen. The reaction was followed by HPLC, and generally conversion to product was complete in two hours or less. The reaction was cooled to room temperature and formic acid was removed in vacuo. Residual water was azeotropically removed with ethanol leaving a light brown to reddish brown solid. If the sulfonamide contained a basic nitrogen, the solid was dissolved in 10% aqueous HCl and washed with three portions of ethyl acetate. The pH of the water layer was adjusted to pH 12 with sodium hydroxide solution and extracted 5 times with ethyl acetate. The collected organic extracts were washed twice with brine, dried and concentrated to afford the appropriate 1H-imidazo[4,5-g]quinazolin-8(7H)-one. If the sulfonamide did not contain a basic nitrogen, the solid obtained after evaporation of the formic acid was dissolved in ethyl acetate and washed twice with water, then brine, dried and concentrated to furnish the appropriate 1H-imidazo[4,5-g]quinazolin-8 (7H)-one. Alternatively, the residual solid was triturated with ether and collected by filtration.

EXAMPLE 1

6-(5-Bromo-2-propoxyphenyl)-1H-imidazo[4,5-g]quinazolin-8(7H)-one

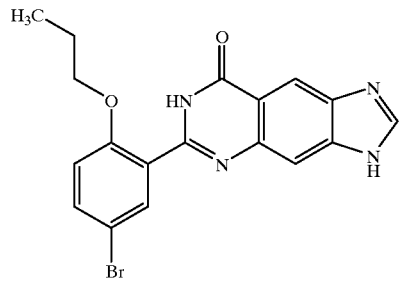

Yield: 96%; mp 154–155° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.37 minutes.

EXAMPLE 2

1-[[3-(7,8-Dihydro-8-oxo-1H-imidazo[4,5-g]quinazolin-6-yl)-4-propoxyphenyl]sulfonyl]-4-methylpiperazine

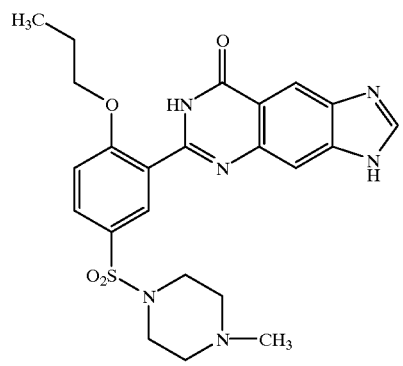

Yield: 66%; mp (free base) 164–167° C.; LRMS [MH+] 483; HPLC (YMC S5 ODS 4.6×50 mm column, 8 minute gradient-0% B to 100% B, 2.5 mL/min flow, solvent A: 10% MeOH-90% H₂O-0.2% H₃PO₄, solvent B: 90% MeOH-10% H₂O-0.2% H₃PO₄) retention time 6.57 minutes.

EXAMPLE 3

1-[[3-(7,8-Dihydro-8-oxo-1H-imidazo[4,5-g]quinazolin-6-yl)-4-propoxyphenyl]sulfonyl]-4-piperidinecarboxylic acid ethyl ester

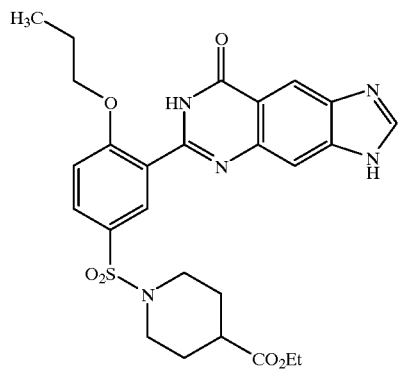

Yield: 64%; mp 145–147° C.; LRMS [MH+] 540; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 3.18 minutes.

EXAMPLE 4

1-[[3-(7,8-Dihydro-8-oxo-1H-imidazo4,5-g]quinazolin-6-yl)-4-propoxyphenyl]sulfonyl]-3-piperidinecarboxylic acid ethyl ester

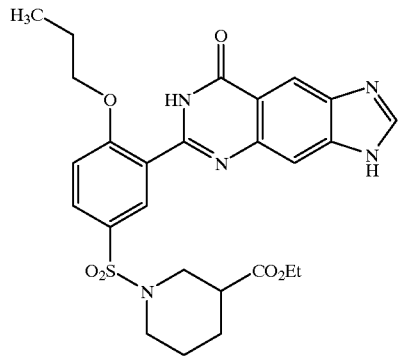

Yield: 92%; mp 154–155° C.; LRMS [MH+] 540; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 3.34 minutes.

EXAMPLE 5

3-(7,8-Dihydro-8-oxo-1H-imidazo[4,5-g]quinazolin-6-yl)-N-(2-1H-imidazol-4-ylethyl)-4-propoxybenzenesulfonamide

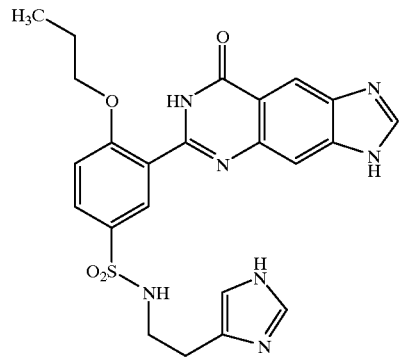

Yield: 25%; mp 285–289° C.; LRMS [MH+] 494; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 2.40 minutes.

EXAMPLE 6

3-(7,8-Dihydro-8-oxo-1H-imidazo[4,5-g]quinazolin-6-yl)-N-(1H-indazol-5-yl)-4-propoxybenzenesulfonamide

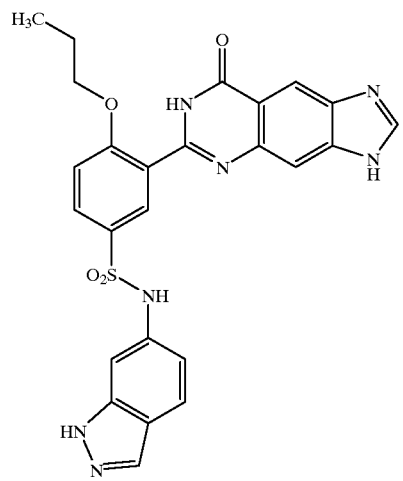

Yield: 32%; mp 261–263° C.; LRMS [MH+] 536; HPLC (YMC S5 ODS 4.6×50 mm column, 4 minute gradient-0% B to 100% B, 4 mL/min flow, solvent A: 10% MeOH-90% H₂O-0.2% H₃PO₄, solvent B: 90% MeOH-10% H₂O-0.2% H₃PO₄) retention time 3.42 minutes.

EXAMPLE 7

4-Benzyl-1-[[3-(7,8-dihydro-8-oxo-1H-imidazo[4,5-g]quinazolin-6-yl)-4-propoxyphenyl]sulfonyl]piperazine

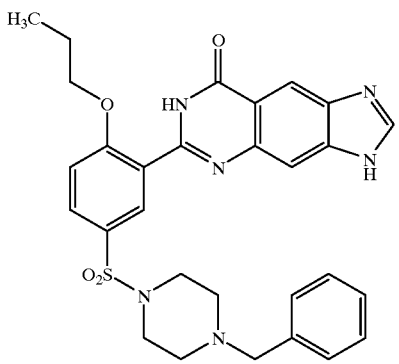

Yield: 38%, mp 191–194° C.; LRMS [MH+] 559; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.44 minutes.

EXAMPLE 8

3-(7,8-Dihydro-8-oxo-1H-imidazo[4,5-g]quinazolin-6-yl)-N-(2-dimethylaminoethyl)-4-propoxybenzenesulfonamide

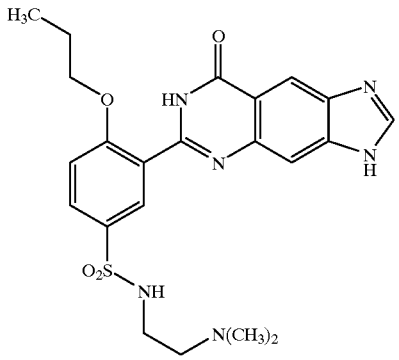

Yield: 40%, mp 212–214° C.; LRMS [MH+] 471; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.11 minutes.

EXAMPLE 9

6-(2-Ethoxyphenyl)-1H-imidazo[4,5-g]quinazolin-8(7H)-one

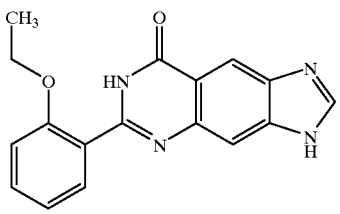

Yield: 92%; LRMS [MH+] 307; mp 194–196° C.; HPLC (YMC S5 ODS 4.6×50 mm column, 4 minute gradient-0% B to 100% B, 4 ml/min flow, solvent A: 10% MeOH-90% $H_2O$-0.2% $H_3PO_4$, solvent B: 90% MeOH-10% $H_2O$-0.2% $H_3PO_4$) retention time 2.55 minutes.

EXAMPLE 10

6-(2-Propoxyphenyl)-1H-imidazo[4,5-g]quinazolin-8(7H)-one

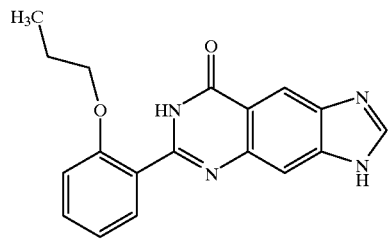

Yield: 93%; LRMS [MH+] 321; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 5.23 minutes.

EXAMPLE 11

1-[[4-Butoxy-3-(7,8-Dihydro-8-oxo-1H-imidazo[4,5-g]quinazolin-6-yl)phenyl]sulfonyl]-4-methylpiperazine

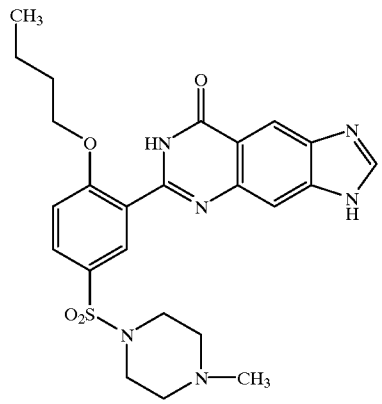

Yield: 83%; mp 124–126° C.; LRMS [MH+] 497; HPLC (YMC S5 ODS 4.6×50 mm column, 4 minute gradient-0%

EXAMPLE 12

3-(7,8-Dihydro-8-oxo-1H-imidazo[4,5-g]quinazolin-6-yl)-N-(4-pyridylmethyl)-4-propoxybenzenesulfonamide

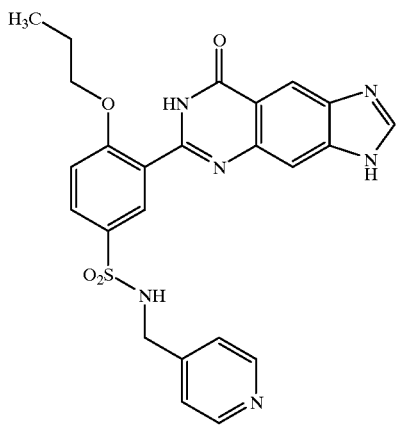

Yield: 72%; mp 189–190° C.; LRMS [MH+] 491; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 2.27 minutes.

EXAMPLE 13

4-Acetyl-1-[[3-(7,8-Dihydro-8-oxo-1H-imidazo[4,5-g]quinazolin-6-yl)-4-propoxyphenyl]sulfonyl]piperazine

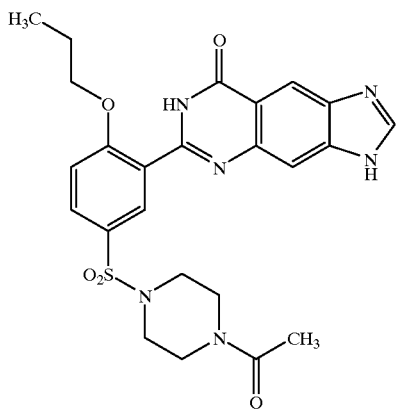

Yield: 49%; mp 230–232° C.; LRMS [MH+] 511; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 2.67 minutes.

EXAMPLE 14

1-[[3-(7,8-Dihydro-8-oxo-1H-imidazo[4,5-g]quinazolin-6-yl)-4-propoxyphenyl]sulfonyl]-4-ethylpiperazine

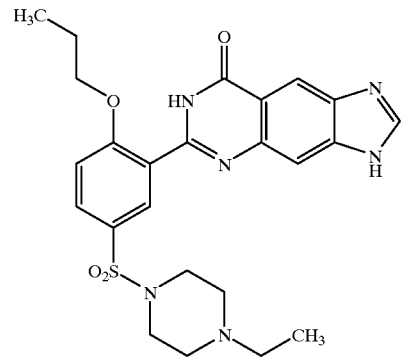

Yield: 82%; mp 194–196° C.; LRMS [MH+] 497; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 2.30 minutes.

EXAMPLE 15

1-[[3-(7,8-Dihydro-8-oxo-1H-imidazo[4,5-g]quinazolin-6-yl)-4-propoxyphenyl]sulfonyl]piperazine

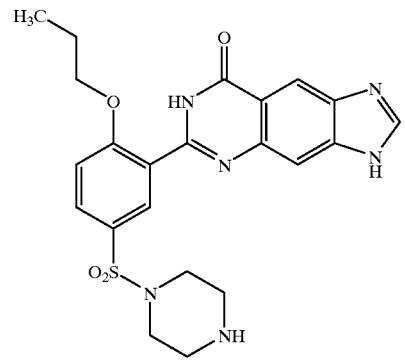

The title compound was prepared using the title compound of Example 13 as follows: 0.045 g (0.09 mmol) of the Example 13 compound was dissolved in 5 mL of 85% hydrazine hydrate and heated to 70° C. overnight. Solvent was removed by rotary evaporation leaving a residue which was purified by preparative HPLC to furnish 0.012 g (0.02 mmol, 23% yield) of the title compound as the trifluoroacetate salt. mp 248–249° C.; LRMS [MH+] 469; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 2.32 minutes.

EXAMPLES 16 to 18

The following general procedure was used for the preparation of the compounds of Examples 16 to 18:

3-(7,8-dihydro-8-oxo-1H-imidazo [4,5g]quinazolin-6-yl)-4-propoxy benzoic acid (0.12 g, 0.33 mmol, Example 53) was suspended in 6 mL of methylene chloride containing 2 drops of DMF. To this, 59 mg (0.46 mmol) oxalyl chloride was added at 0° C. The reaction was allowed to warm to room temperature and after two hours was warmed to reflux for three hours. The solvent was removed by rotary evaporation leaving the crude acid chloride which was used for the synthesis of the following examples. This crude material was suspended in a mixture of THF/methylene chloride (5:1) at room temperature. To this was added a six-fold excess of the appropriate amine at room temperature. This mixture was stirred overnight. Solvents were removed by rotary evaporation. The residue was dissolved in methanol and purified by preparative HPLC to afford the pure amide title compounds of Examples 16 to 18.

EXAMPLE 16

1-[3-(7,8-Dihydro-8-oxo-1H-imidazo[4,5g] quinazolin-6-yl)-4-propoxyl-4-methylpiperazine]-benzamide

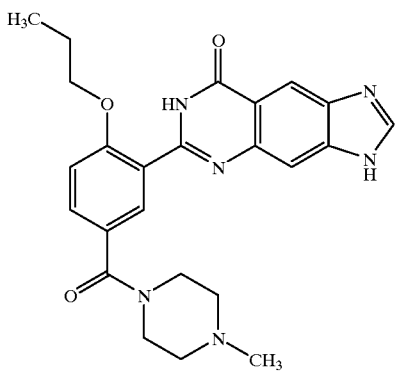

Yield: 5%; mp 178–179° C.; LRMS [MH+] 447; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 1.93 minutes.

EXAMPLE 17

1-[3-(7,8-Dihydro-8-oxo-1H-imidazo[4,5g] quinazolin-6-yl)-4-propoxyl-3-piperidinecarboayic Acid ethyl ester]-benzamide

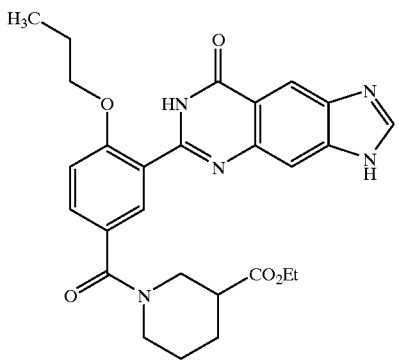

Yield: 15%; mp 120–122° C.; LRMS [MH+] 504 ; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.23 minutes.

EXAMPLE 18

1-[3-(7,8-Dihydro-8-oxo-1H-imidazo[4,5g] quinazolin-6-yl)-4-propoxyl-4-piperidinecarboxylic acid ethyl ester]-benzamide

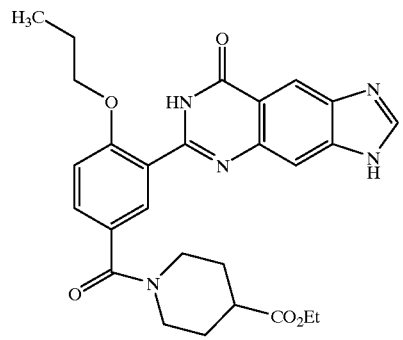

Yield: 10%; mp 132–134° C.; LRMS [MH+] 504; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.23 minutes.

EXAMPLES 19 to 35

The compounds of Examples 19 to 35 were prepared by the following general procedure for the alkylation of 1H-imidazo[4,5-g]quinazolin-8(7H)-ones:

6-(2-Propoxyphenyl)-1H-imidazo[4,5-g]quinazolin-8 (7H)-one (see Example 10) was dissolved in dry DMF at room temperature. Cesium carbonate (1.2–1.4 equivalents) was added, followed by 1.2–1.4 equivalents of the appropriate alkyl halide. For activated substrates (ethyl iodide, propyl iodide, benzyl bromides) the reaction was allowed to proceed at room temperature overnight. For other halides (cyclohexyl methyl iodide and 1-iodo-2-methyl-2-cyclohexyl propyl), it was necessary to warm the reaction to 60–70° C. to complete the reaction. When the reaction was judged complete by tlc or HPLC, the mixture was poured into dilute HCl and extracted 5 times with ethyl acetate. The collected organic extracts were washed with brine twice, dried and concentrated by rotary evaporation to give a mixture of alkylated products which were separated by either flash chromatography or preparative HPLC.

EXAMPLE 19

6-(2-Propoxyphenyl)-3-propyl-1H-imidazo[4,5-g]quinazolin-8(7H)-one

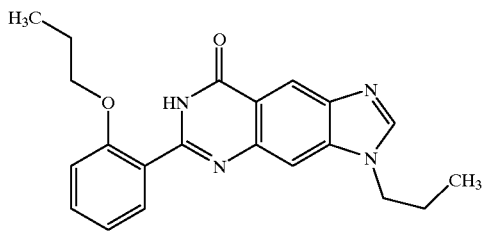

The title compound was purified by flash chromatography eluting with 40% acetone in methylene chloride: 35% yield; mp 165–168° C.; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 6.57 minutes.

EXAMPLE 20

6-(2-Propoxyphenyl)-1-propyl-1H-imidazo [4,5-g]quinazolin-8(7H)-one

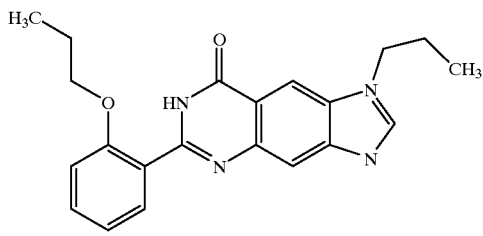

The title compound was purified by flash chromatography eluting with 40% acetone in methylene chloride: 13% yield (6:1 mixture with the title compound of Example 19); mp 158–168° C.; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 6.15 minutes.

EXAMPLE 21

3-Ethyl-6-(2-propoxyphenyl)-1H-imidazo [4,5-g]quinazolin-8(7H)-one

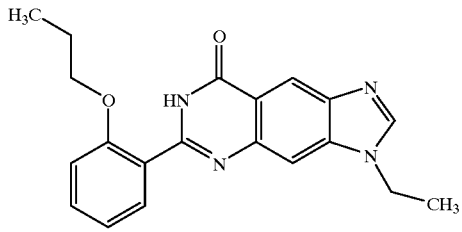

Yield: 20%; mp 147–149° C.; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 5.90 minutes.

EXAMPLE 22

1-Ethyl-6-(2-propoxyphenyl)-1H-imidazo[4,5-g]quinazolin-8(7H)-one

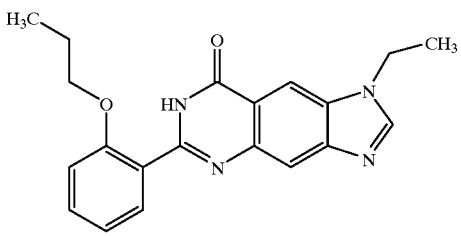

Yield: 15%; mp 212–214° C.; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 5.60 minutes.

EXAMPLE 23

3-Cyclohexylmethyl-6-(2-propoxyphenyl)-1H-imidazo[4,5-g]quinazolin-8(7H)-one

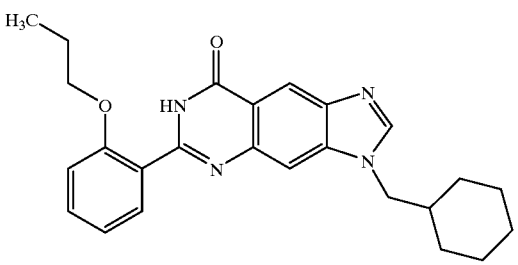

Yield: 14%; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 4.30 minutes.

EXAMPLE 24

1-Cyclohexylmethyl-6-(2-propoxyphenyl)-1H-imidazo[4,5-g]quinazolin-8(7H)-one

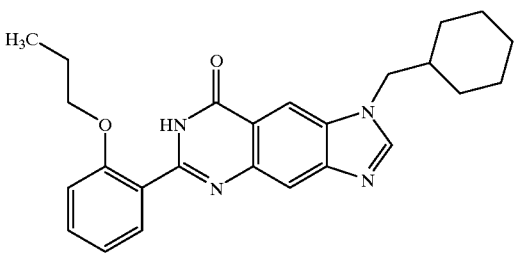

Yield: 15%; mp 223–226° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 4.11 minutes.

EXAMPLE 25

1-(2-Cyclohexylpropyl)-6-(2-propoxyphenyl)-1H-imidazo [4,5-g]quinazolin-8(7H)-one

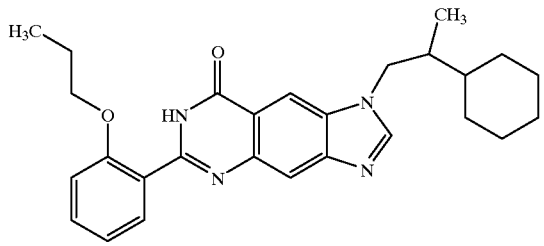

Yield 14%; mp 178–180° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 4.51 minutes.

EXAMPLE 26

1-(Phenylmethyl)-6-(2-propoxyphenyl)-1H-imidazo [4,5-g]quinazolin-8(7H)-one

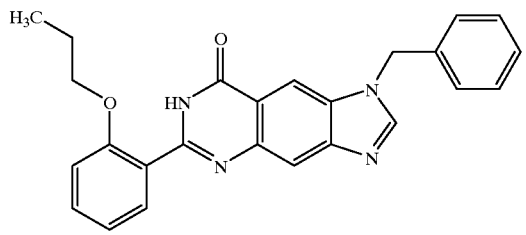

Yield: 25%; mp 218–219° C.; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 7.03 minutes.

EXAMPLE 27

3-(Phenylmethyl)-6-(2-propoxyphenyl)-1H-imidazo [4,5-g]quinazolin-8(7H)-one

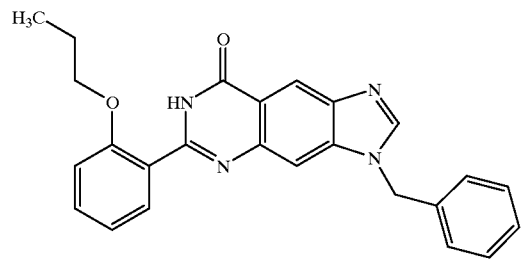

Yield: 20%; mp 170° C. (dec); HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 7.32 minutes.

EXAMPLE 28

1-(4-Chlorophenylmethyl)-6-(2-propoxyphenyl)-1H-imidazo[4,5-g]quinazolin-8(7H)-one

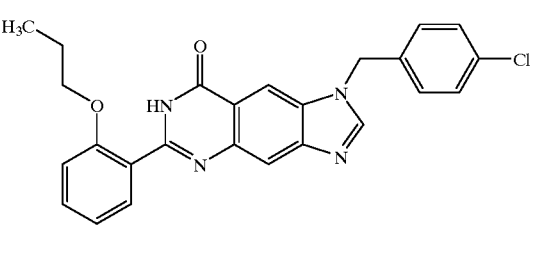

Yield: 18%; mp 136–137° C.; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 7.69 minutes.

EXAMPLE 29

3-(4-Chlorophenylmethyl)-6-(2-propoxyphenyl)-1H-imidazo[4,5-g]guinazolin-8(7H)-one

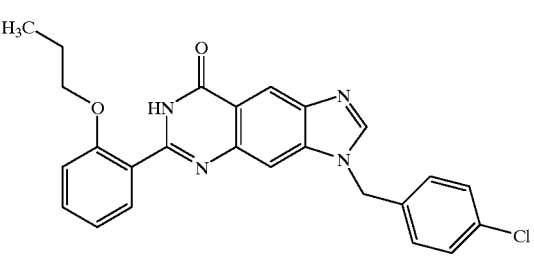

Yield: 21%; mp 190–191° C.; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 7.89 minutes.

EXAMPLE 30

Mixture of 1-(4-Nitrophenylmethyl)-6-(2-propoxyphenyl)-1H-imidazo[4,5-g]quinazolin-8(7H)-one and 3-(4-Nitrophenylmethyl)-6-(2-propoxyphenyl)-1H-imidazo[4,5-g]quinazolin-8(7H)-one

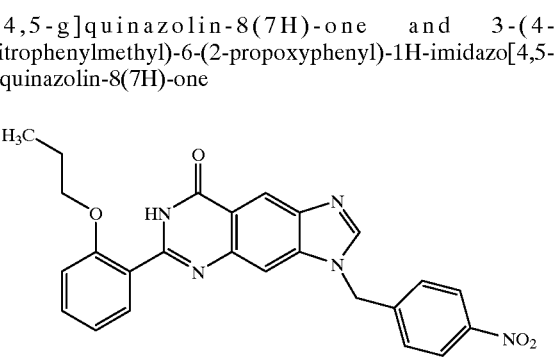

-continued

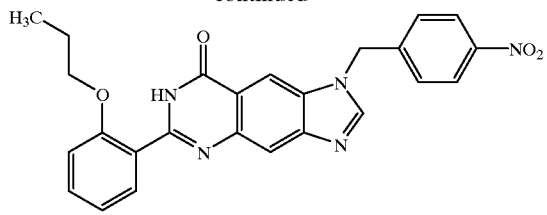

Yield: 51%; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention times 3.81 & 3.87 minutes.

EXAMPLE 31

1-(4-Methoxyphenylmethyl)-6-(2-propoxyphenyl)-1H-imidazo[4,5-g]quinazolin-8(7H)-one

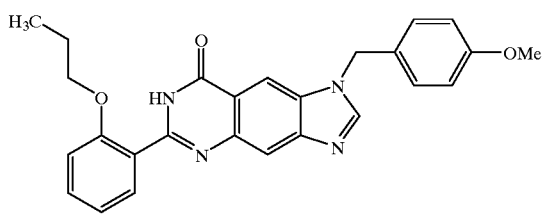

Yield: 16%; mp 203–204° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.71 minutes.

EXAMPLE 32

3-(4-Methoxyphenylmethyl)-6-(2-propoxyphenyl)-1H-imidazo[4,5-g]quinazolin-8(7H)-one

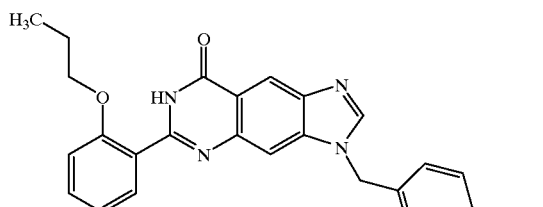

Yield: 15%; mp 130–131° C.; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.85 minutes.

EXAMPLE 33

1-(Phenethyl)-6-(2-propoxyphenyl)-1H-imidazo[4,5-g]quinazolin-8(7H)-one

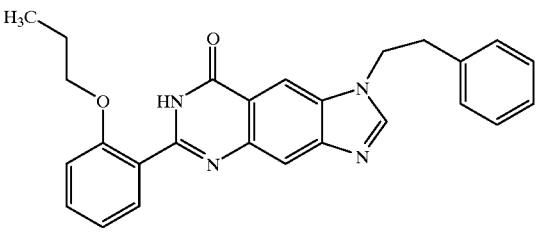

Yield: 10%; mp 184° C. (dec); HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 5.60 minutes.

EXAMPLE 34

3-(Phenethyl)-6-(2-propoxyphenyl)-1H-imidazo[4,5-g]quinazolin-8(7H)-one

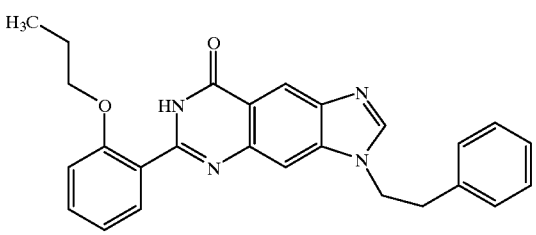

Yield: 21%; oil; HPLC (YMC S5 ODS 4.6×50 mm column, 8 minute gradient-0% B to 100% B, 2.5 mL/min flow, solvent A: 10% MeOH-90% $H_2O$-0.2% $H_3PO_4$, solvent B: 90% MeOH-10% $H_2O$-0.2% $H_3PO_4$) retention time 7.40 minutes; NMR (400 MHz, DMSO $d_6$) δ 11.0 (br s, 1H), 8.76 (s, 1H), 8.54–8.58 (m, 1H), 7.81 (s, 1H), 7.72 (s, 1H), 7.49 (apparent t, 1H, J=1.5 Hz), 7.00–7.29 (m, 5H), 4.49 (t, 2H, J=6.8 Hz), 4.19 (t, 2H, J=6.4 Hz), 3.20 (t, 2H, J=6.5 Hz), 2.03–2.05 (m, 2H), 1.17 (t, 3H, J=7.2 Hz).

EXAMPLE 35

1-(Pyridylmethyl)-6-(2-propoxyphenyl)-1H-imidazo[4,5-g]quinazolin-8(7H)-one and 3-(Pyridylmethyl)-6-(2-propoxyphenyl)-1H-imidazo[4,5-g]quinazolin-8(7H)-one

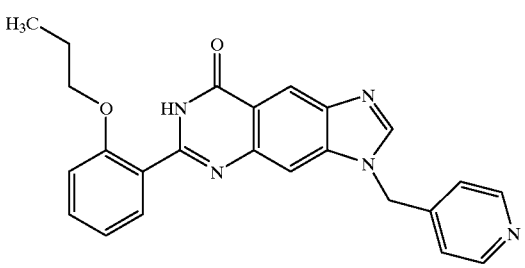

-continued

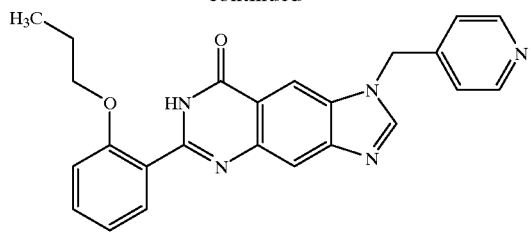

Yield: 35% of a 1:1 mixture; LRMS [MH+] 412; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention times 4.85 and 4.92 minutes.

The compounds of Examples 36 to 39 were prepared as described following.

EXAMPLE 36

1-[[3-(7,8-Dihydro-8-oxo-1H-imidazo [4,5-g] quinazolin-6-yl)-4-propoxyphenyl]sulfonyl]-4-(2-hydroxyethyl)piperazine

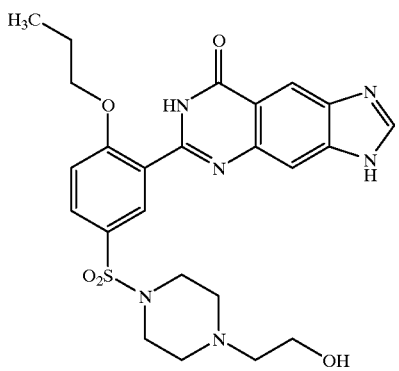

6-(2-Propoxyphenyl)-1H-imidazo[4,5-g]quinazolin-8 (7H)-one (0.134 g, 0.42 mmol) was added to 2 mL of ice cold chlorosulfonic acid in one portion. After 30 minutes at 0° C., the brown solution was warmed to room temperature and stirred for 3.5 hours. The reaction mixture was then cautiously poured into crushed ice. Sufficient 2-hydroxyethyl piperazine was added to this mixture to adjust pH>9. The mixture was then stirred at room temperature for 2 hours. A precipitated solid was collected by filtration and discarded. The pH was then adjusted to pH>11 with potassium carbonate, and the aqueous solution extracted with ethyl acetate (5×). The organic extracts were combined, washed twice with brine, dried, and concentrated to furnish 23 mg of a tan solid. This impure material was triturated with ether to afford the title compound as a tan solid (0.005 g, 2%): mp dec>205° C.; LRMS [MH+] 513; HPLC (YMC S5 ODS 4.6×50 mm column, 8 minute gradient-0% B to 100% B, 2.5 mL/min flow, solvent A: 10% MeOH-90% H$_2$O-0.2% H$_3$PO$_4$, solvent B: 90% MeOH-10% H$_2$O-0.2% H$_3$PO$_4$) retention time 4.07 minutes.

EXAMPLE 37

1-[[3-(7,8-Dihydro-8-oxo-1H-imidazo[4,5-g] quinazolin-6-yl)-4-propoxyphenyl]sulfonyl]-4-piperidinecarboxylic acid

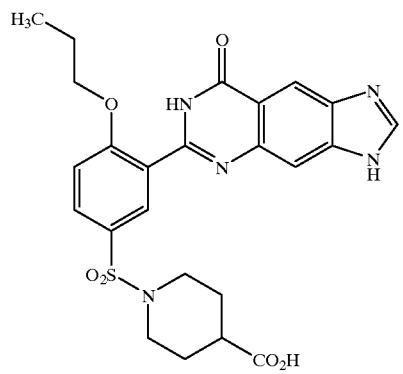

A mixture of 1-[[3-(7,8-dihydro-8-oxo-1H-imidazo[4,5-g]quinazolin-6-yl)-4-propoxyphenyl]sulfonyl]-4-piperidinecarboxylic acid ethyl ester (0.018 g) (see Example 3) and lithium hydroxide (1.5 eq) in aqueous THF (9:1 THF/water) was stirred at room temperature for 5 hours. When the starting material had been consumed as determined by tlc analysis, the reaction mixture was concentrated and the resulting residue dissolved in water. Glacial acetic acid was added to adjust the pH to ~3 by pH paper. The solid that precipitated was collected by filtration, washed with water and ether to afford the title acid as a light brown solid (0.014 g, 82% yield): mp 215–217° C.; LRMS [MH+] 512; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO4) retention time 2.77 minutes.

EXAMPLE 38

1-[[3-(7,8-Dihydro-8-oxo-1H-imidazo[4,5-g] quinazolin-6-yl)-4-propoxyphenyl]sulfonyl]-3-piperidinecarboxylic acid

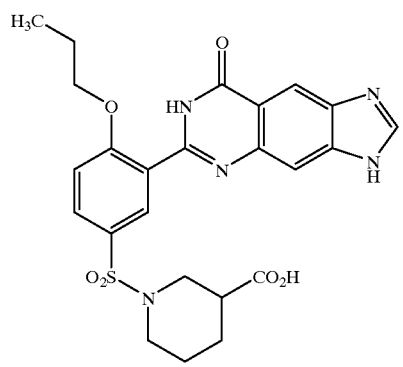

Using the same method as described for Example 37, a 62% yield of a tan solid was obtained. mp 219–222° C., LRMS [MH+] 512, HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 2.94 minutes.

EXAMPLE 39

6-(2-Propoxyphenyl)-1H-1,2,3-triazolo[4,5-g]quinazolin-8(7H)-one

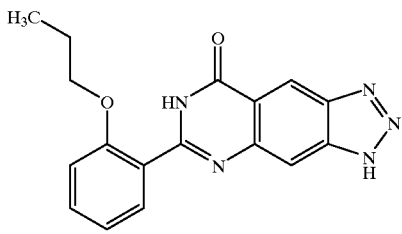

6,7-diamino-2-(2-propoxyphenyl)-4(3H)-quinazolinone (0.15 g, 0.51 mmol) was suspended in 1N HCl (5 mL) and cooled in an ice-methanol bath. A solution of sodium nitrite (0.035 g) in water (1 mL) was added in one portion. The reaction was stirred in an ice bath for 30 minutes, then warmed to room temperature for 90 minutes. The precipitated solid was collected by filtration, washed with water, and dried to afford the title compound as a brown solid (0.42 mmol, 83%): mp dec>260° C.; LRMS [MH+] 308.

EXAMPLES 40 to 48

The compounds of Examples 40 to 48 were prepared as described below:

The appropriate 5-amino-[(phenylmethyl)amino]-1H-benzimidazole-6-carboxamides (Preparation 9A–G) were coupled with the appropriate carboxylic acids (Preparation 12A–B and 12D) by one of the two following methods, and this product was cyclized to afford the title compounds of Examples 40 to 48.

Method 1:

The carboxylic acid (1.3 equivalents relative to the 5-amino-1-[(phenylmethyl)amino]-1H-benzimidazole-6-carboxamide) was dissolved in 10–20 mL methylene chloride and two drops of DMF were added. To this solution was added 1.3–1.5 equivalents of oxalyl chloride over 20–30 minutes. The reaction mixture was stirred at room temperature for two hours, then concentrated by rotary evaporation. The residue was suspended in 10–25 mL of pyridine and 1–3 mL DMF and the 5-amino-1-[(phenylmethyl)amino]-1H-benzimidazole-6-carboxamide was added. The reaction mixture was heated to 75° C. for 1–2 hours then cooled to room temperature and poured into ice. If the product precipitated, it was collected by filtration, washed with water and dried and used without further purification for the succeeding step. If the product did not precipitate, it was extracted from the aqueous mixture using 4×25 mL portions of methylene chloride. The organic layer was washed with brine, dried and concentrated by rotary evaporation.

Method 2:

The carboxylic acid (1.1 to 1.4 equivalents relative to the 5-amino-1-[(phenylmethyl)amino]-1H-benzimidazole-6-carboxamide) was dissolved in 5–10 mL pyridine containing 0.5 to 1 mL DMF. 4-Dimethylamino pyridine (0.1 equivalent), 2-hydroxybenzotriazole (1.2 equivalents) and 1-(3-dimethylaminopropyl)-3-ethylcarbodiimide (1.2 equivalents) were added, followed by the 5-amino-1-[(phenylmethyl)amino]-1H-benzimidazole-6-carboxamide. The reaction was stirred at room temperature for 1–3 hours then diluted with methylene chloride (100–200 mL) and washed with 3×50 mL portions of water and brine. The organic layer was dried and concentrated to afford the amide.

Cyclization

The crude amide product from Method 1 or 2 was suspended in dry t-butanol (5–25 mL) and an excess of potassium t-butoxide in t-butanol (2.2–5 equivalents) was added. The reaction mixture was heated to reflux and followed by HPLC until the starting material had been consumed (1–5 hours). The reaction was cooled to room temperature and poured into ice to precipitate the product, which was collected by filtration and washed with water. In some cases, purification was accomplished using flash chromatography over silica gel eluting with acetone/methanol (5 to 10:1) to furnish the pure product.

EXAMPLE 40

1-[[3-[7,8-Dihydro-8-oxo-1-(phenylmethyl)-1H-imidazo[4,5-g]quinazolin-6-yl]-4-propoxyphenyl]sulfonyl]-4-methylpiperazine

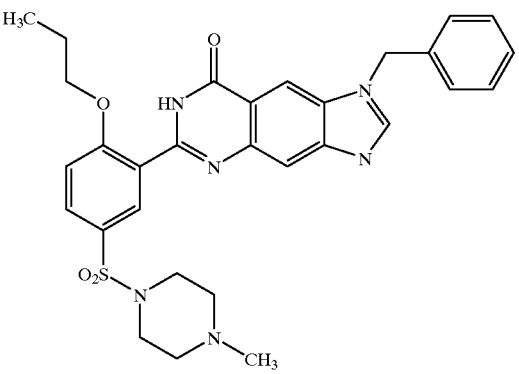

(Method 1) yield: 39%; LRMS [MH+] 573; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.09 minutes.

EXAMPLE 41

1-[[3-[1-[(4-Fluorophenyl)methyl-7,8-dihydro-8-oxo-1H-imidazo[4,5-g]quinazolin-6-yl]-4-propoxyphenyl]sulfonyl]-4-methylpiperazine

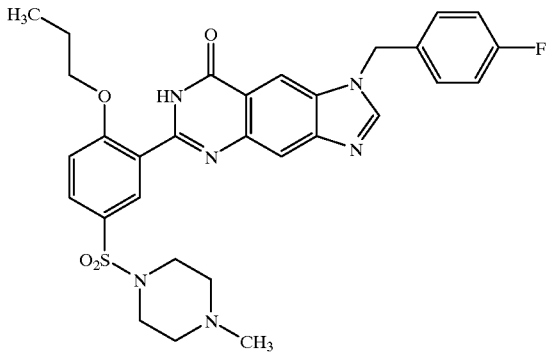

(Method 2) yield 80%; mp 227–228° C.; LRMS [MH+] 591; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.16 minutes.

EXAMPLE 42

1-[[3-[1-[(4-fluorophenyl)methyl]-7,8-dihydro-8-oxo-1H-imidazo[4,5-g]quinazolin-6-yl]-4-propoxyphenyl]sulfonyl]-4-ethylpiperazine

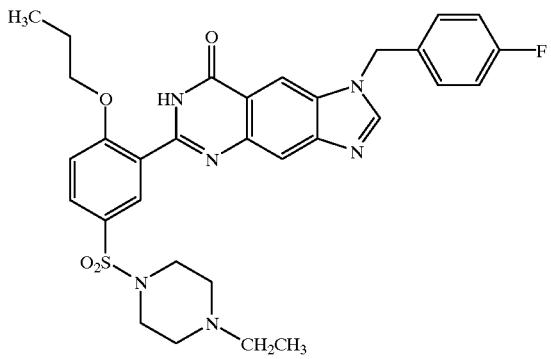

(Method 2) yield 52%; mp 155–158° C.; LRMS [MH+] 605; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.14 minutes.

EXAMPLE 43

1-[[3-[1-[(3-fluorophenyl)methyl]-7,8-dihydro-8-oxo-1H-imidazo[4,5-g]quinazolin-6-yl]-4-propoxyphenyl]sulfonyl]-4-ethylpiperazine

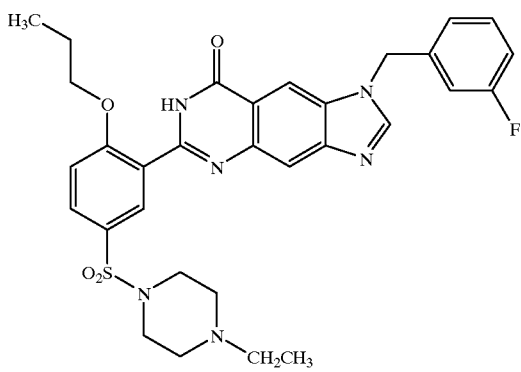

(Method 2) yield: 93%; LRMS [MH+] 605; mp 115–117° C.; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.18 minutes.

EXAMPLE 44

1-[[3-[7,8-Dihydro-1-[(3-methoxyphenyl)methyl]-8-oxo-1H-imidazo[4,5-g]quinazolin-6-yl]-4-propoxyphenyl]sulfonyl]-4-ethylpiperazine

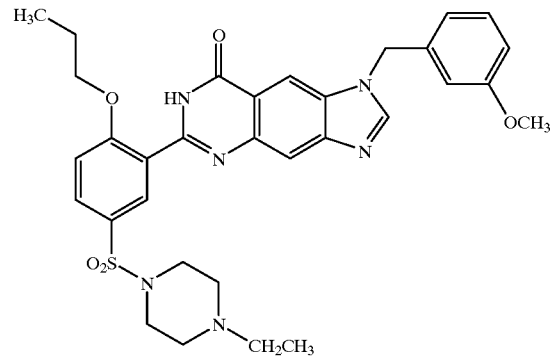

(Method 1) yield: 55%; mp 117–118° C.; LRMS [MH+] 617; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.13 minutes.

EXAMPLE 45

1-[[3-[7,8-Dihydro-1-[(2-methoxyphenyl)methyl]-8-oxo-1H-imidazo[4,5-g]quinazolin-6-yl]-4-propoxyphenyl]sulfonyl]-4-ethylpiperazine

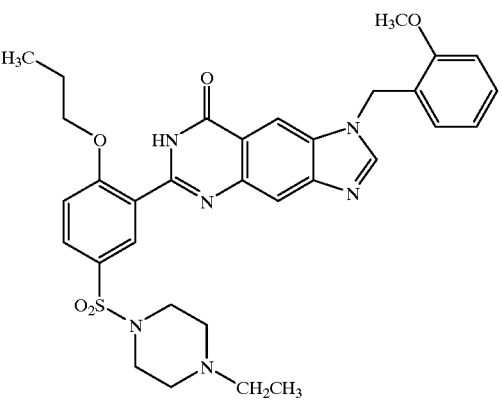

(Method 1) yield: 30%; mp 180–182° C.; LRMS [MH+] 617; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.15 minutes.

EXAMPLE 46

1-[[3-[1-[(3-Chlorophenyl)methyl]-7,8-dihydro-8-oxo-1H-imidazo[4,5-g]quinazolin-6-yl]-4-propoxyphenyl]sulfonyl]-4-methylpiperazine

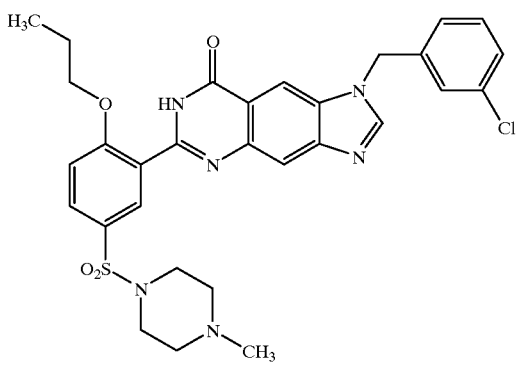

(Method 1) yield: 50%; mp 198–200° C.; LRMS [MH+] 607; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.31 minutes.

EXAMPLE 47

1-[[3-[1-[(2-Chlorophenyl)methyl]-7,8-dihydro-8-oxo-1H-imidazo[4,5-g]quinazolin-6-yl]-4-propoxyphenyl]sulfonyl]-4-ethylpiperazine

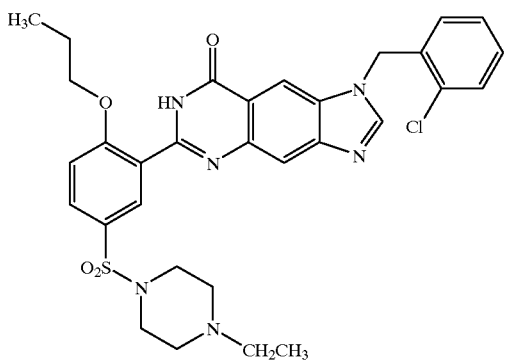

(Method 1) yield: 49%; mp 225–226° C.; LRMS [MH+] 622; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.36 minutes.

EXAMPLE 48

(R)-1-[[3-[1-[(4-Fluorophenyl)methyl]-7,8-dihydro-8-oxo-1H-imidazo[4,5-g]quinazolin-6-yl]-4-propoxyphenyl]sulfonyl]-3-(dimethylamino)pyrrolidine

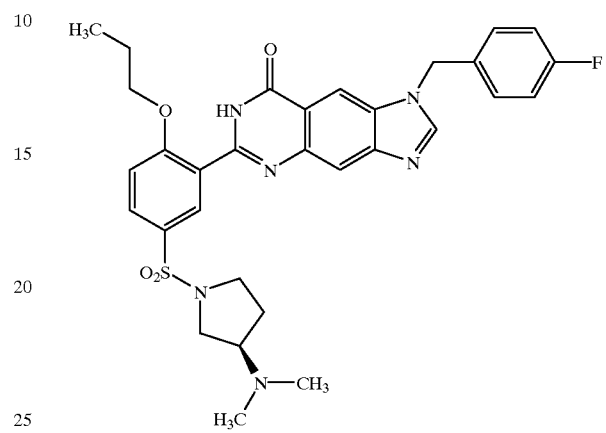

(Method 2) yield 69%; mp 223–225° C.; LRMS [MH+] 605; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.14 minutes.

EXAMPLES 49 to 52

The compounds of Examples 49 to 52 were prepared using the following general method:

The title compound of Example 26 was dissolved in methylene chloride (20 mL), followed by 1 equivalent of thionyl chloride. To this was added a 2.0M solution of chlorosulfonic acid in methylene chloride (10 equivalents) dropwise over 20 to 30 minutes. The reaction was stirred at room temperature for 6 hours then poured cautiously onto crushed ice. The solid that was formed was collected by filtration and washed with water and dried under high vacuum to afford the intermediate sulfonic acid which was used without further purification for the next step.

The sulfonic acid was partially dissolved in a mixture of thionyl chloride (3–10 mL) and N-methyl pyrrolidinone (1–3 mL) at room temperature. The reaction mixture was stirred at room temperature for 4 hours, then poured onto ice to deposit a yellow solid which was collected by filtration and dried affording a crude sulfonyl chloride which was contacted, without further purification, with the appropriate amine to prepare the title compounds of Examples 49 to 52.

EXAMPLE 49

1-[[3-[7,8-Dihydro-8-oxo-1-(phenylmethyl)-1H-imidazo [4,5- g]quinazolin-6-yl]-4-propoxyphenyl] sulfonyl]-4-ethylpiperazine

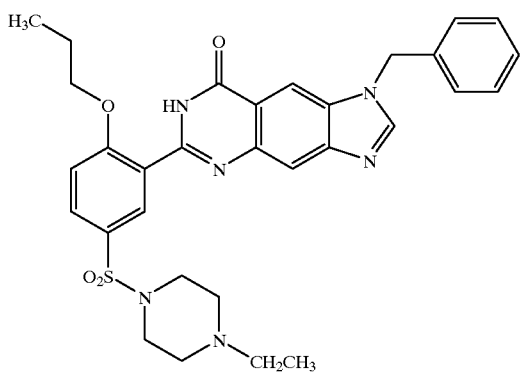

Yield: 24%; mp 135–137° C.; LRMS [MH+] 587; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.10 minutes.

EXAMPLE 50

1-[[3-[7,8-Dihydro-8-oxo-1-(phenylmethyl)-1H-imidazo[4,5-g]quinazolin-6-yl]-4-propoxyphenyl] sulfonyl]-4-propylpiperazine

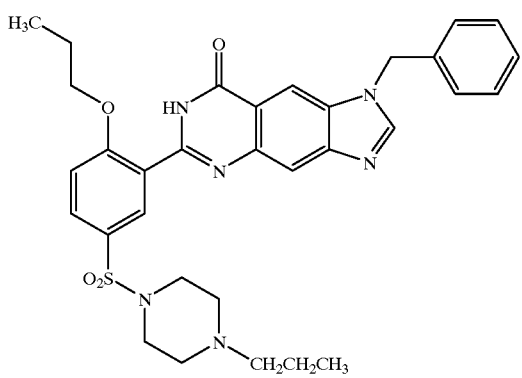

Yield: 16%; mp 194–195° C.; LRMS [MH+] 601; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.12 minutes.

EXAMPLE 51

(R)-1-[[3-[7,8-Dihydro-8-oxo-1-(phenylmethyl)-1H-imidazo[4,5-g]quinazolin-6-yl]-4-propoxyphenyl] sulfonyl]-3-(dimethylamino)pyrrolidine

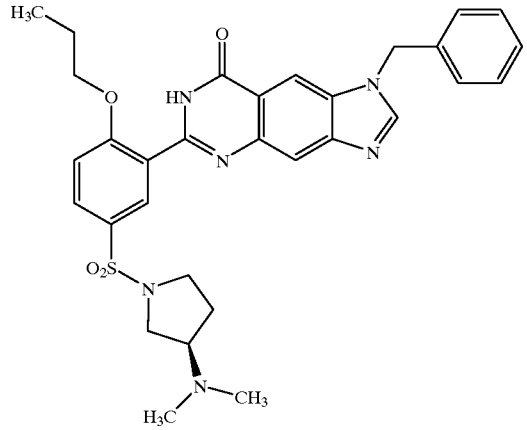

Yield: 30%; mp >300° C. (HCl salt); LRMS [MH+] 587; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.07 minutes.

EXAMPLE 52

(S)-1-[[3-[7,8-Dihydro-8-oxo-1-(phenylmethyl)-1H-imidazo[4,5-g]quinazolin-6-yl]-4-propoxyphenyl] sulfonyl]-3-(dimethylamino)pyrrolidine

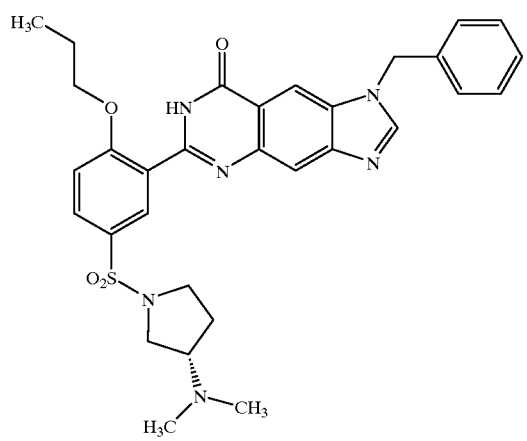

Yield: 30%; mp 190° C. (decomp., HCl salt); LRMS [MH+] 587; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.08 minutes.

EXAMPLE 53

3-(7,8-Dihydro-8-oxo-1H-imidazo[4,5g]quinazolin-6-yl)-4-propoxy benzoic acid

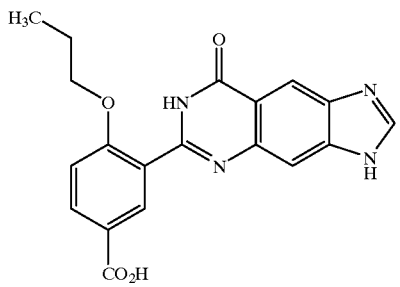

Sodium hydride (0.22 g, 5.5 mmol) was suspended in dry THF and cooled to 0° C. in an ice bath. A solution of 6-(5-bromo-2-propoxyphenyl)-1H-imidazo[4,5-g]quinazolin-8(7H)-one (1.00 g, 2.5 mmol, Example 1) in 100 ml dry THF was added dropwise and stirring was continued for one hour at 0° C. after addition was complete. The reaction mixture was cooled to −78° C. and 12 mL of a 2M solution of n-butyl lithium in hexane (24 mmol) was added dropwise over 45 minutes. Stirring was continued for 45 minutes at −78° C., before carbon dioxide (from dry ice) was bubbled through the reaction solution for 40 minutes. The reaction was allowed to warm to 0° C. and water was added cautiously to quench the reaction. THF was removed by rotary evaporation and the residue was diluted with water. The aqueous mixture was extracted with 4×25 mL of methylene chloride. The aqueous layer was concentrated and the residue filtered through HP-20 ion exchange resin. The resin was washed with water and the product was eluted with methanol. Fractions containing the product were concentrated to afford 0.53 g (58%, 1.45 mmol) of product as a tan solid, mp 195–196° C.; LRMS [MH+] 365; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.73 minutes.

The following general procedure was employed for the synthesis of the title compounds of Examples 54 and 55.

The appropriate 7-amino-2-(2-propoxyphenyl)-6-nitro-4 (3H)-quinazoline sulfonamide (see Preparations 4M and 4N) was suspended in a mixture of 96% formic acid and distilled water (6:1 v/v) with 10% by weight of 10% palladium on carbon. The reaction mixture was heated to reflux for 30–45 minutes when HPLC analysis indicated starting material had been consumed. The cooled reaction mixture was filtered through celite then concentrated under reduced pressure. The resulting solid was dried azeotropically with methanol three times then purified by preparative HPLC to furnish the product as the corresponding trifluoroacetate salt.

EXAMPLE 54

4-[[3-(7,8-Dihydro-8-oxo-1H-imidazo[4,5-g]quinazolin-6-yl)-4-propoxyphenyl]sulfonyl]-1-piperazineacetic acid ethyl ester

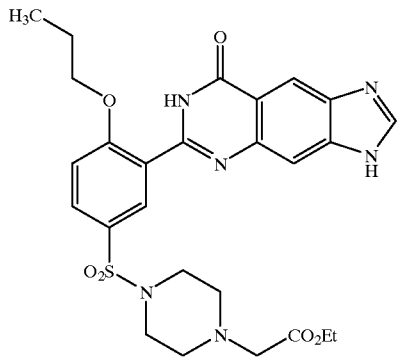

Yield: 77%, mp 188–192° C. (TFA salt); LRMS [MH+] 555; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.46 minutes.

EXAMPLE 55

4-[[3-(7,8-Dihydro-8-oxo-1H-imidazo[4,5-g]quinazolin-6-yl)-4-propoxyphenyl]sulfonyl]-1-ethyl-2-piperazinecarboxylic acid ethyl ester

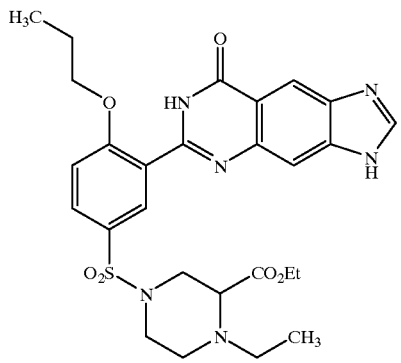

Yield: 77%; mp 158–163° C. (TFA salt): LRMS [MH+] 569; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 2.60 minutes.

The title compounds of Examples 56 and 57 were prepared using the general procedure outlined for the preparation of the compounds of Examples 16 to 18.

EXAMPLE 56

3-[[(7,8-Dihydro-8-oxo-1H-imidazo[4,5g]quinazolin-6-yl)-4-propoxyphenyl]carbonyl]-4-ethylpiperazine

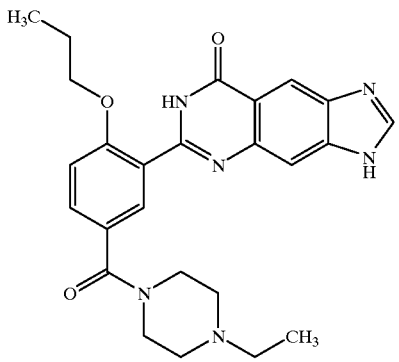

Yield: 40%; mp 98–100° C. (trifluoroacetate salt); LRMS [MH+] 461; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 1.90 minutes.

EXAMPLE 57

(S)-[[3-(7,8-Dihydro-8-oxo-1H-imidazo[4,5g]quinazolin-6-yl)-4-propoxyphenyl]carbonyl]-3-dimethylaminopyrrolidine

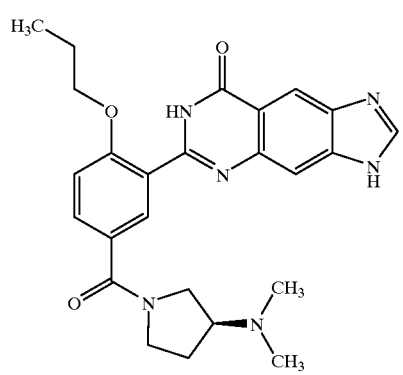

Yield: 35%; mp 115–117° C. (trifluoroacetate salt); LRMS [MH+] 461; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 1.90 minutes.

EXAMPLES 58 to 79

The compounds in Table 1 were prepared using the general procedure outlined above for the synthesis of Examples 49 to 52. HPLC method for retention times: YMC S5 ODS 4.6×50 mm column, 4 minute gradient 0% B to 100% B, 4 ml/min flow, solvent A: 10% MeOH-90% $H_2O$-0.2% $H_3PO_4$, solvent B 90% MeOH-10% $H_2O$-0.2% $H_3PO_4$.

TABLE 1

| Ex. No. | Compound Name | Structure | % purity | HPLC retention time (minutes) | Other data (mp ° C.) |
|---|---|---|---|---|---|
| 58 | 1-[[3-[7,8-Dihydro-8-oxo-1-(phenylmethyl)-1H-imidazo[4,5-g]quinazolin-6-yl]-4-propoxyphenyl]sulfonyl]-hexahydro-4-methyl-1H-1,4-diazepine | 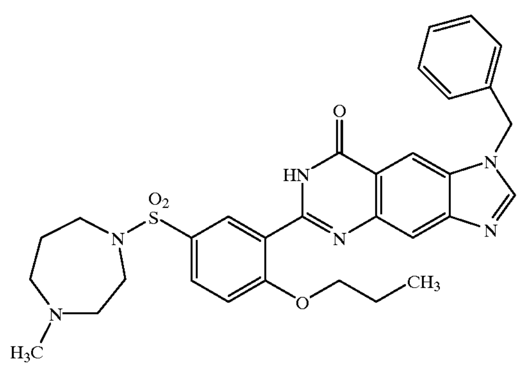 | 98 | 3.10 | LC-MS m + H 587 |

TABLE 1-continued

| Ex. No. | Compound Name | Structure | % purity | HPLC retention time (minutes) | Other data (mp ° C.) |
|---|---|---|---|---|---|
| 59 | 1-[[3-[7,8-Dihydro-8-oxo-1-(phenylmethyl)-1H-imidazo[4,5-g]quinazolin-6-yl]-4-propoxyphenyl]sulfonyl]-4-dimethylaminopiperazine | 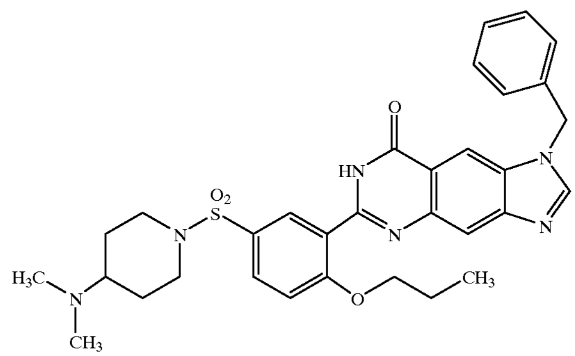 | 90 | 3.10 | LC-MS m +H 601 |
| 60 | 1-[[3-[7,8-Dihydro-8-oxo-1-(phenylmethyl)-1H-imidazo[4,5-g]quinazolin-6-yl]-4-propoxyphenyl]sulfonyl]-4-isopropylpiperazine | 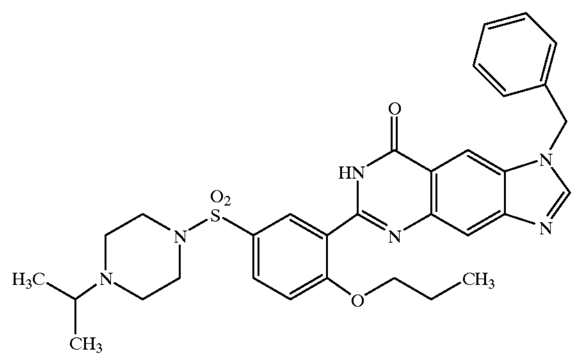 | 98 | 3.10 | LC-MS m + H 601 (mp 120–121) |
| 61 | 1-[[3-[7,8-Dihydro-8-oxo-1-(phenylmethyl)-1H-imidazo[4,5-g]quinazolin-6-yl]-4-propoxyphenyl]sulfonyl]-4-phenylpiperazine | 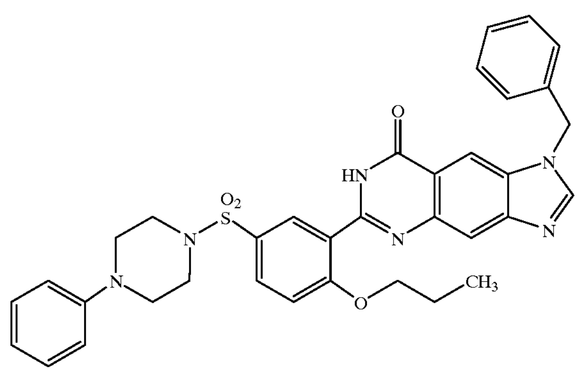 | 90 | 3.82 | LC-MS m + H 635 |

TABLE 1-continued

| Ex. No. | Compound Name | Structure | % purity | HPLC retention time (minutes) | Other data (mp ° C.) |
|---|---|---|---|---|---|
| 62 | 4-[[3-[7,8-Dihydro-8-oxo-1-(phenylmethyl)-1H-imidazo[4,5-g]quinazolin-6-yl]-4-propoxyphenyl]sulfonyl]-N-(1-methylethyl)-1-piperazineacetamide | 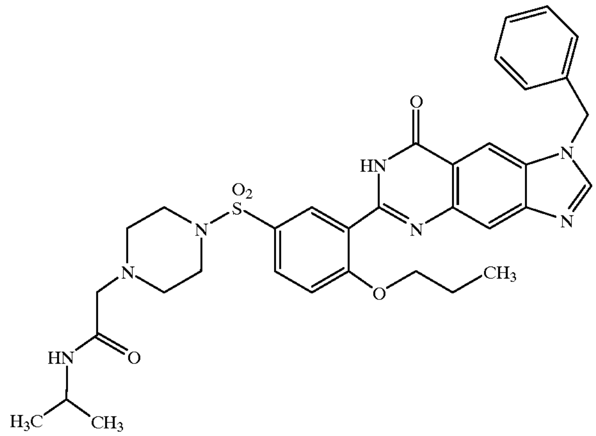 | 90 | 3.57 | LC-MS m + H 658 |
| 63 | 1-[[3-[7,8-Dihydro-8-oxo-1-(phenylmethyl)-1H-imidazo[4,5-g]quinazolin-6-yl]-4-propoxyphenyl]sulfonyl]-1-amino-4-methylpiperazine | 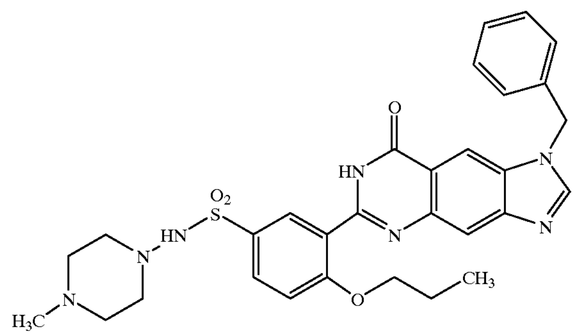 | 95 | 3.44 | LC-MS m + H 588 |
| 64 | 1-[[3-[7,8-Dihydro-8-oxo-1-(phenylmethyl)-1H-imidazo[4,5-g]quinazolin-6-yl]-4-propoxyphenyl]sulfonyl]-4-(2-pyridyl)piperazine | 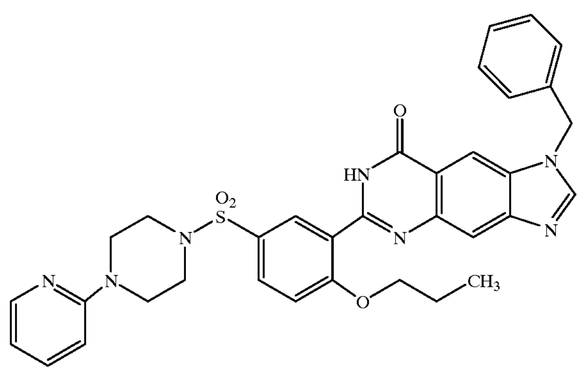 | 90 | 3.55 | LC-MS m + H 636 |
| 65 | 1-[[3-[7,8-Dihydro-8-oxo-1-(phenylmethyl)-1H-imidazo[4,5-g]quinazolin-6-yl]-4-propoxyphenyl]sulfonyl]-[2-(2-aminomethyl)-ethylpyridine] | 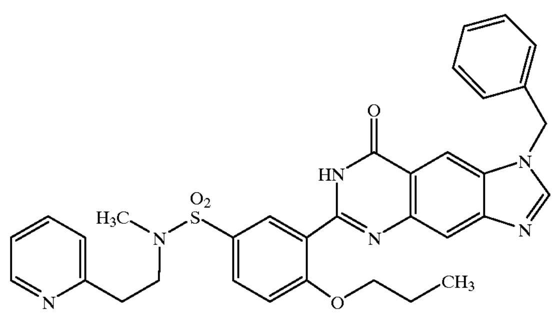 | 90 | 3.55 | LC-MS m + H 609 |

TABLE 1-continued

| Ex. No. | Compound Name | Structure | % purity | HPLC retention time (minutes) | Other data (mp ° C.) |
|---|---|---|---|---|---|
| 66 | 1-[[3-[7,8-Dihydro-8-oxo-1-(phenylmethyl)-1H-imidazo(4,5-g]quinazolin-6-yl]-4-propoxyphenyl]sulfonyl]-(2-aminoethyl)-pyridine | 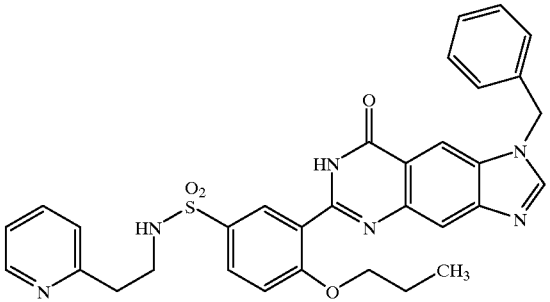 | 85 | 3.47 | LC-MS m + H 595 |
| 67 | 1-[[3-[7,8-Dihydro-8-oxo-1-(phenylmethyl)-1H-imidazo[4,5-g]quinazolin-6-yl]-4-propoxyphenylsulfonyl]-3-(aminomethyl)-pyridine | 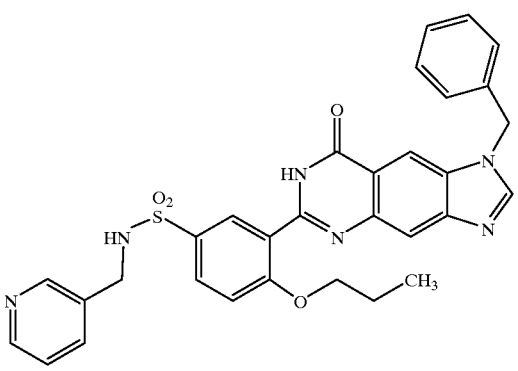 | 89 | 3.47 | LC-MS m + H 581 |
| 68 | 1-[[3-[7,8-Dihydro-8-oxo-1-(phenylmethyl)-1H-imidazo[4,5-g]quinazolin-6-yl]-4-propoxyphenyl]sulfonyl]-[1-(2-aminoethyl)]-piperidine | 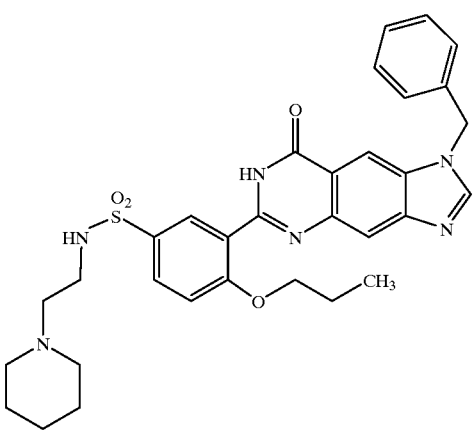 | 90 | 3.52 | LC-MS m + H 601 |

TABLE 1-continued

| Ex. No. | Compound Name | Structure | % purity | HPLC retention time (minutes) | Other data (mp ° C.) |
|---|---|---|---|---|---|
| 69 | 1-[[3-[7,8-Dihydro-8-oxo-1-(phenylmethyl)-1H-imidazo[4,5-g]quinazolin-6-yl]-4-propoxyphenyl]sulfonyl]-3-(N,N-dimethylamino)propyl-amine | 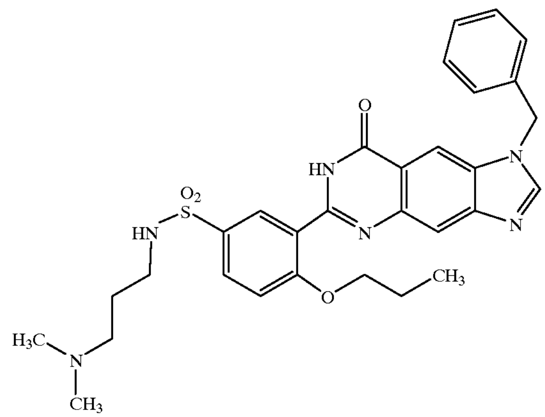 | 86 | 3.47 | LC-MS m + H 575 |
| 70 | 1-[[3-[7,8-Dihydro-8-oxo-1-(phenylmethyl)-1H-imidazo[4,5-g]quinazolin-6-yl]-4-propoxyphenyl]sulfonyl]-[4-(2-aminoethyl)]-pyridine | 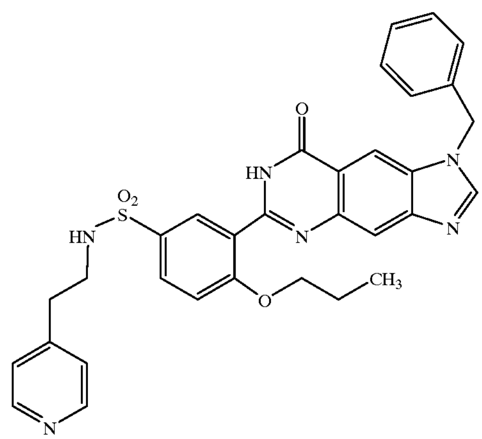 | 84 | 3.41 | LC-MS m + H 595 |
| 71 | 1-[[3-[7,8-Dihydro-8-oxo-1-(phenylmethyl)-1H-imidazo[4,5-g]quinazolin-6-yl]-4-propoxyphenyl]sulfonyl]-4-(2-fluoro)-phenylpiperazine | 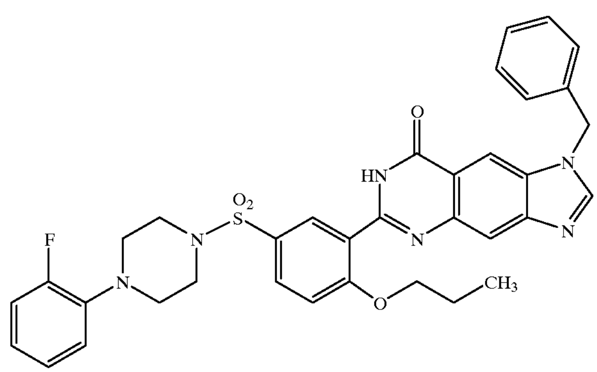 | 90 | 4.37 | LC-MS m + H 653 |

TABLE 1-continued

| Ex. No. | Compound Name | Structure | % purity | HPLC retention time (minutes) | Other data (mp ° C.) |
|---|---|---|---|---|---|
| 72 | 1-[[3-[7,8-Dihydro-8-oxo-1-(phenylmethyl)-1H-imidazo[4,5-g]quinazolin-6-yl]-4-propoxyphenyl]sulfonyl]-4-(2-cyano)-phenylpiperazine | 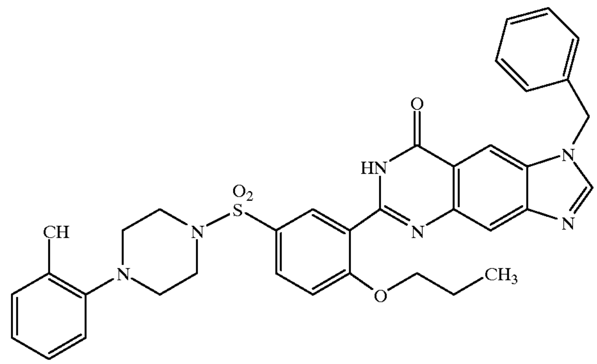 | 100 | 3.77 | LC-MS m + H 660 |
| 73 | 1-[[3-[7,8-Dihydro-8-oxo-1-(phenylmethyl)-1H-imidazo[4,5-g]quinazolin-6-yl]-4-propoxyphenyl]sulfonyl]-4-cyclohexylpiperazine | 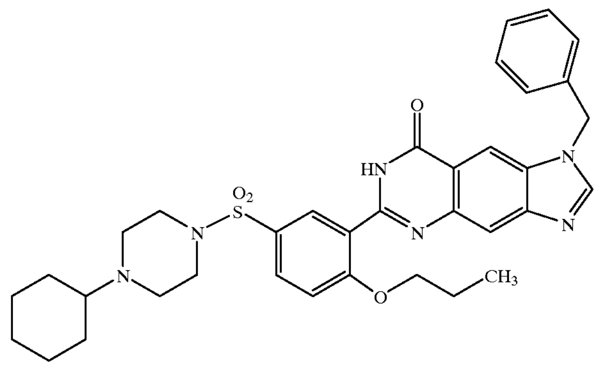 | 88 | 3.60 | LC-MS m + H 641 |
| 74 | 1-[[3-[7,8-Dihydro-8-oxo-1-(phenylmethyl)-1H-imidazo[4,5-g]quinazolin-6-yl]-4-propoxyphenyl]sulfonyl]-4-(2-methoxyethyl)piperazine | 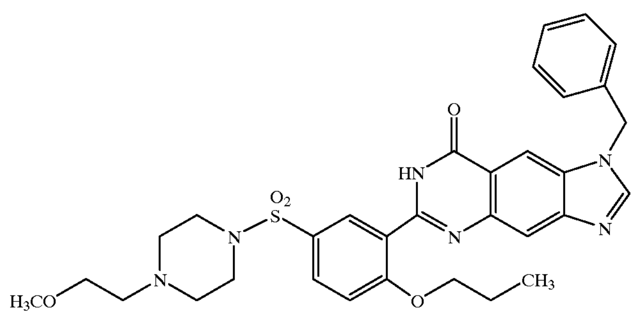 | 92 | 3.52 | LC-MS m + H 617 |
| 75 | 1-[[3-[7,8-Dihydro-8-oxo-1-(phenylmethyl)-1H-imidazo[4,5-g]quinazolin-6-yl]-4-propoxyphenyl]sulfonyl]-[3-(2-aminoethyl)]-pyridine | 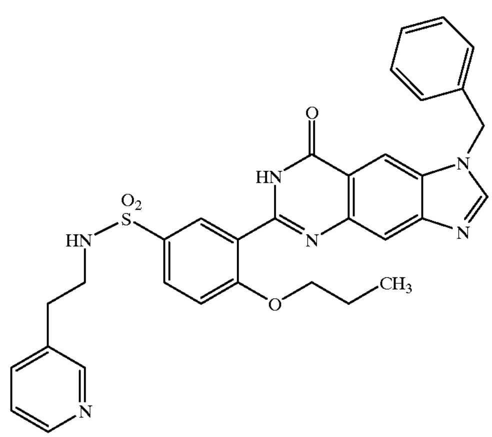 | 92 | 3.49 | LC-MS m + H 595 |

TABLE 1-continued

| Ex. No. | Compound Name | Structure | % purity | HPLC retention time (minutes) | Other data (mp ° C.) |
|---|---|---|---|---|---|
| 76 | 1-[[3-[7,8-Dihydro-8-oxo-1-(phenylmethyl)-1H-imidazo[4,5-g]quinazolin-6-yl]-4-propoxyphenyl]sulfonyl]-4-hydroxy piperidine | 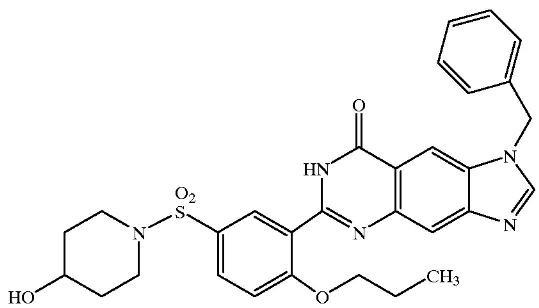 | 95 | 3.42 | LC-MS m + H 574 |
| 77 | 1-[[3-[7,8-Dihydro-8-oxo-1-(phenylmethyl)-1H-imidazo[4,5-g]quinazolin-6-yl]-4-propoxyphenyl]sulfonyl]-4-(N-methyl)-1-methylpiperidine | 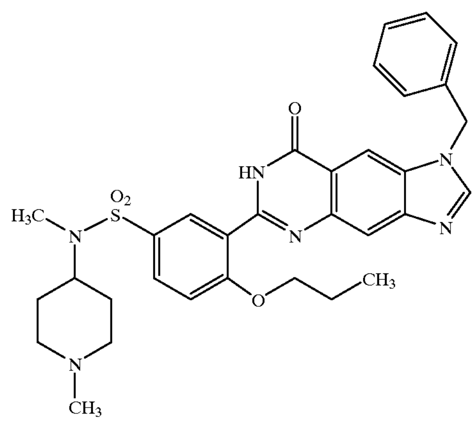 | 95 | 3.13 | LC-MS m + H 601 |
| 78 | 1-[[3-[7,8-Dihydro-8-oxo-1-(phenylmethyl)-1H-imidazo[4,5-g]quinazolin-6-yl]-4-propoxyphenyl]sulfonamide | 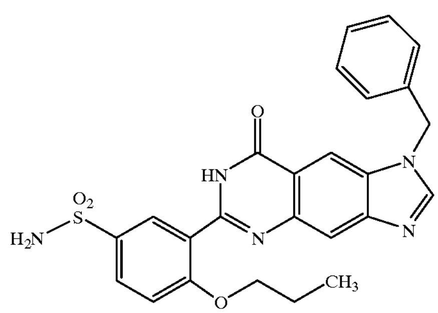 | 90 | 3.24 | LC-MS m + H 490 |
| 79 | 1-[[3-[1-[(4-Fluorophenyl)methyl]-7,8-dihydro-8-oxo-1H-imidazo[4,5-g]quinazolin-6-yl]-4-propoxyphenyl]sulfonamide | 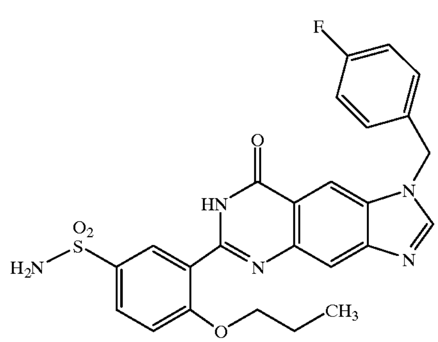 | 90 | 3.29 | LC-MS m + H 508 |

EXAMPLES 80 to 93

The compounds of Table 2 below were prepared using the carboxylic acid title compound of Example 112 and the appropriate amine. Coupling was carried out using the following general procedure: the carboxylic acid title compound of Example 112 (1.0 eq) was dissolved in pyridine containing 1.2 equivalents each of EDAC-HCl, HOBt, the appropriate amine and 0.2 equivalents of dimethylaminopyridine. The reaction was stirred at room temperature for 2–5 hours. Most of the pyridine was removed under reduced pressure and the residue was poured into water. In most cases a solid precipitated which was collected by filtration, washed with water and dried. If a solid did not precipitate, the aqueous mixture was extracted five times with ethyl acetate. The collected organic layers were washed twice with brine then dried and concentrated. If further purification was necessary (less than 85% pure by HPLC), it was carried out using preparative HPLC. Analytical HPLC method: YMC S5 ODS 4.6×50 mm column, 4 minute gradient 0% B to 100% B, 4 ml/min flow, solvent A: 10% MeOH-90% $H_2O$-0.2% $H_3PO_4$, solvent B 90% MeOH-10% $H_2O$-0.2% $H_3PO_4$.

TABLE 2

| Ex. No. | Compound Name | Structure | % purity | HPLC retention time (minutes) | Other data |
|---|---|---|---|---|---|
| 80 | (S)-1-[[3-[1-[(4-Fluorophenyl)methyl]-7,8-dihydro-8-oxo-1H-imidazo[4,5-g]quinazolin-6-yl]-4-propoxyphenyl)carbonyl]-3-(dimethylamino)pyrrolidine | 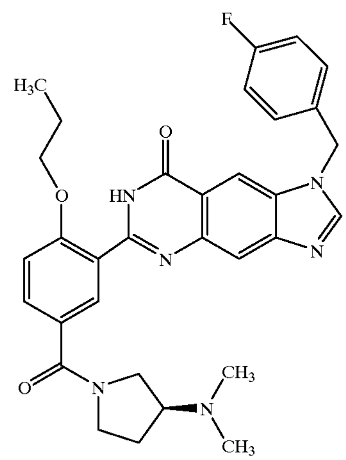 | 89 | 2.99 | LC-MS m + H 569 |
| 81 | 1-[[3-[1-[(4-Fluorophenyl)methyl)-7,8-dihydro-8-oxo-1H-imidazo[4,5-g]quinazolin-6-yl]-4-propoxyphenyl]carbonyl)-3-amino-1-ethylpiperazine | 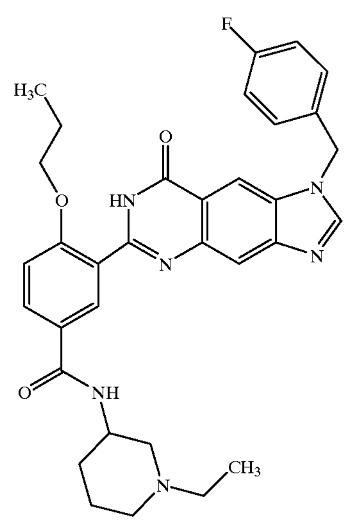 | 99 | 3.22 | LC-MS m + H 583 |

TABLE 2-continued

| Ex. No. | Compound Name | Structure | % purity | HPLC retention time (minutes) | Other data |
|---|---|---|---|---|---|
| 82 | 1-[[3-[1-[(4-Fluorophenyl)methyl]-7,8-dihydro-8-oxo-1H-imidazo[4,5-g]quinazolin-6-yl]-4-propoxyphenyl]carbonyl]-1-amino-4-methylpiperazine | 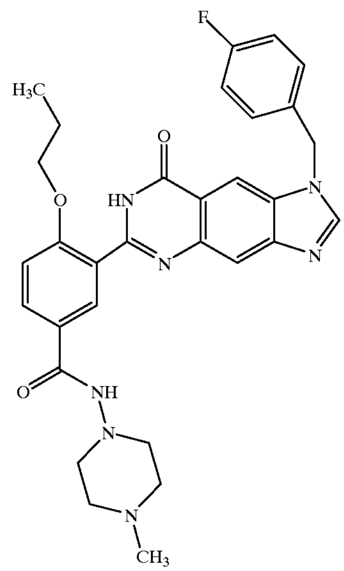 | 87 | 3.52 | LC-MS m + H 570 |
| 83 | 1-[[3-[1-[(4-Fluorophenyl)methyl]-7,8-dihydro-8-oxo-1H-imidazo[4,5-g]quinazolin-6-yl]-4-propoxyphenyl]carbonyl]-[2-(2-amino-ethyl)]-pyridine | 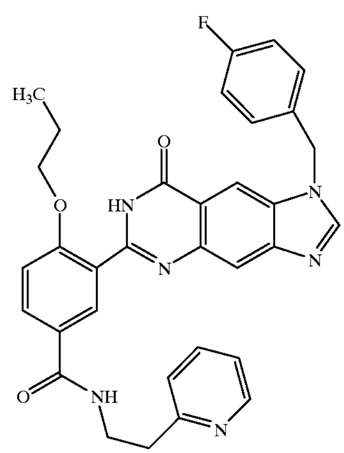 | 90 | 3.57 | LC-MS m + 577 |
| 84 | 1-[[3-[1-[(4-Fluorophenyl)methyl]-7,8-dihydro-8-oxo-1H-imidazo[4,5-g]quinazolin-6-yl]-4-propoxyphenyl]carboxamide | 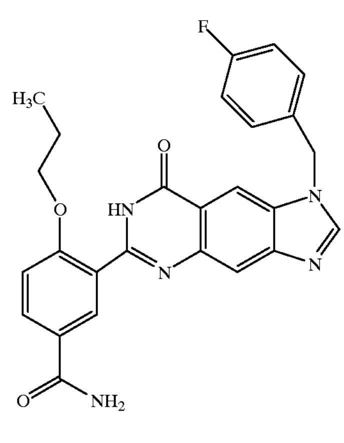 | 97 | 3.60 | LC-MS m + 472 |

TABLE 2-continued

| Ex. No. | Compound Name | Structure | % purity | HPLC retention time (minutes) | Other data |
|---|---|---|---|---|---|
| 85 | 1-[[3-[1-[(4-Fluorophenyl)methyl]-7,8-dihydro-8-oxo-1H-imidazo[4,5-g]quinazolin-6-yl]-4-propoxyphenyl]-N,N-dimethyl-carboxamide | 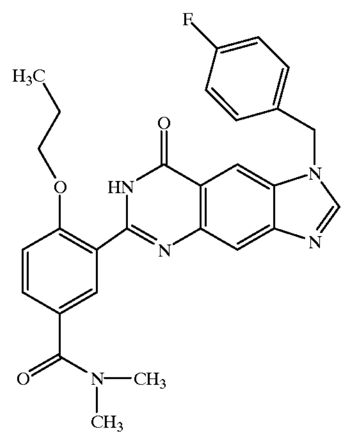 | 91 | 3.71 | LC-MS m + H 500 |
| 86 | 1-[[3-[1-[(4-Fluorophenyl)methyl]-7,8-dihydro-8-oxo-1H-imidazo[4,5-g]quinazolin-6-yl]-4-propoxyphenyl]carbonyl]-2,6-dimethyl piperazine | 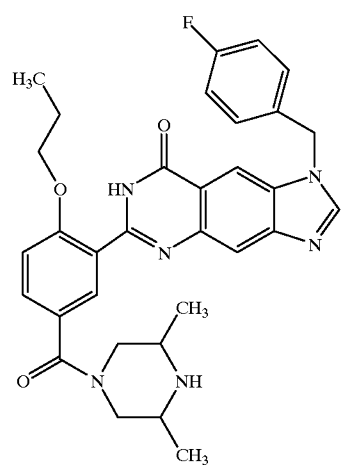 | 90 | 3.57 | LC-MS m + H 569 |
| 87 | 1-[[3-[1-[(4-Fluorophenyl)methyl]-7,8-dihydro-8-oxo-1H-imidazo [4,5-g]quinazolin-6-yl]-4-propoxyphenyl]carbonyl]-N-methyl-[2-(2-aminoethyl)-pyridine | 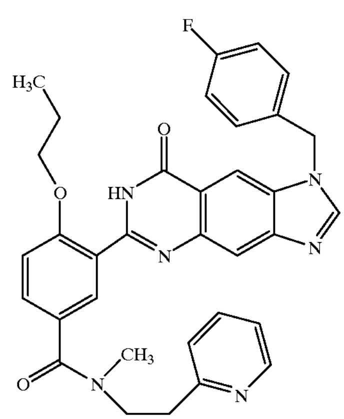 | 95 | 3.52 | LC-MS m + H 591 |

TABLE 2-continued

| Ex. No. | Compound Name | Structure | % purity | HPLC retention time (minutes) | Other data |
|---|---|---|---|---|---|
| 88 | 1-[[3-[1-[(4-Fluorophenyl)methyl]-7,8-dihydro-8-oxo-1H-imidazo[4,5-g]quinazolin-6-yl]-4-propoxyphenyl]carbonyl)-4-aminomethyl-1-N-methyl piperidine | 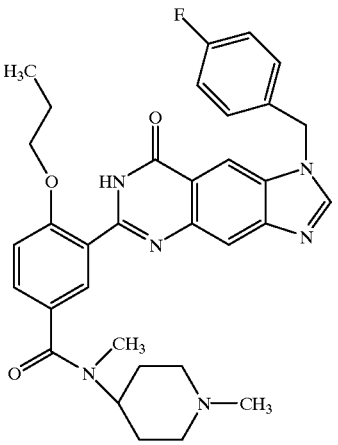 | 100 | 3.52 | LC-MS m + H 583 |
| 89 | 1-[[3-[1-[(4-Fluorophenyl)methyl]-7,8-dihydro-8-oxo-1H-imidazo[4,5-g]quinazolin-6-yl]-4-propoxyphenyl]carbonyl]-2-isopropylamino-ethanol | 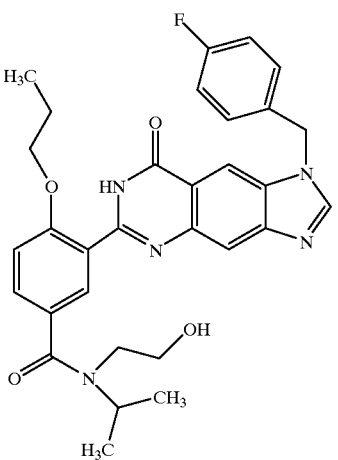 | 83 | 3.65 | LC-MS m + H 558 |
| 90 | (R)-3-[[[3-[1-[(4-Fluorophenyl)methyl]-7,8-dihydro-8-oxo-1H-imidazo[4,5-g]quinazolin-6-yl]-4-propoxyphenyl]carbonyl]amino]-1-pyrrolidineacetic acid ethyl ester | 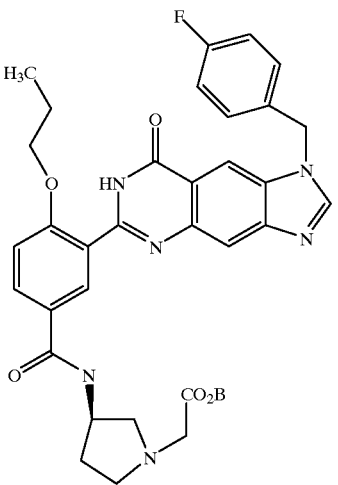 | 91 | 3.65 | LC-MS m + H 627 |

TABLE 2-continued

| Ex. No. | Compound Name | Structure | % purity | HPLC retention time (minutes) | Other data |
|---|---|---|---|---|---|
| 91 | 1-[[3-[1-[(4-Fluorophenyl)methyl]-7,8-dihydro-8-oxo-1H-imidazo[4,5-g]quinazolin-6-yl]-4-propoxyphenyl]carbonyl)-4-piperidine carboxylic acid ethyl ester | 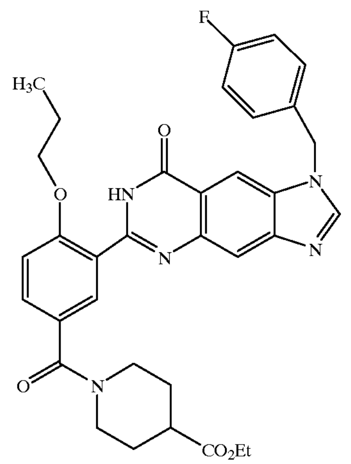 | 95 | 3.80 | LC-MS m + H 612 |
| 92 | 1-Ethyl-4-[[3-[1-[(4-fluorophenyl)methyl]-7,8-dihydro-8-oxo-1H-imidazo[4,5-g]quinazolin-6-yl]-4-propoxyphenyl]carbonyl]piperazine | 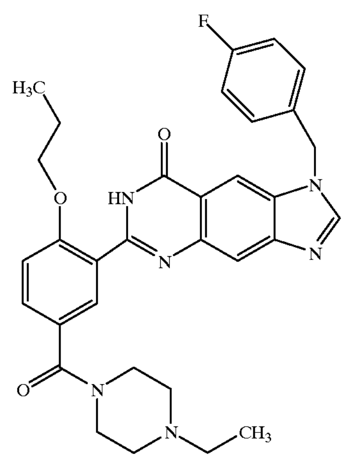 | 95 | 3.00 | LC-MS m + H 569 |
| 93 | 1-[[3-[1-[(4-Fluorophenyl)methyl]-7,8-dihydro-8-oxo-1H-imidazo[4,5-g]quinazolin-6-yl]-4-ethoxyphenyl]carboxamide | 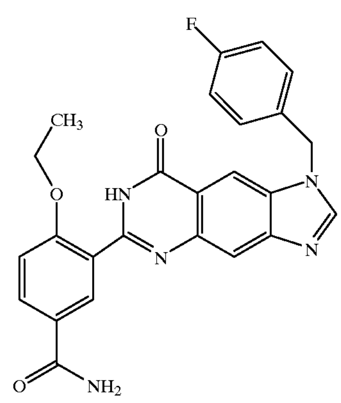 | 91 | 3.20 | LC-MS m + H 458 |

EXAMPLES 94 to 98

The compounds of Table 3 were prepared using the general coupling and cyclization procedures described above for the preparation of the compounds of Examples 40 to 48. HPLC method: YMC S5 ODS 4.6×50 mm column, 4 minute gradient 0% B to 100% B, 4 ml/min flow, solvent A: 10% MeOH-90% $H_2O$-0.2% $H_3PO_4$, solvent B 90% MeOH-10% $H_2O$-0.2% $H_3PO_4$.

TABLE 3

| Ex. No. | Compound Name | Structure | % purity | HPLC retention time (minutes) | Other data (mp ° C.) |
|---|---|---|---|---|---|
| 94 | (R)-1-[[3-[1-[(4-Methoxyphenyl)methyl]-7,8-dihydro-8-oxo-1H-imidazo[4,5-g]quinazolin-6-yl]-4-propoxyphenyl]sulfonyl]-3-(dimethylamino)pyrrolidine | 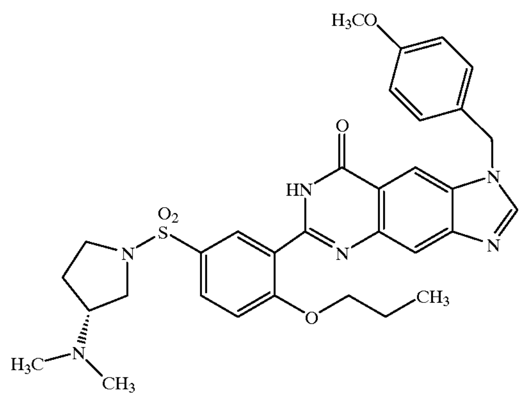 | 97 | 3.10 | LC-MS m + H 617 (mp 207–209) |
| 95 | (R)-1-[[3-[1-[(3-Cyanophenyl)methyl]-7,8-dihydro-8-oxo-1H-imidazo[4,5-g]quinazolin-6-yl]-4-propoxyphenyl]sulfonyl]-3-(dimethylamino)pyrrolidine | 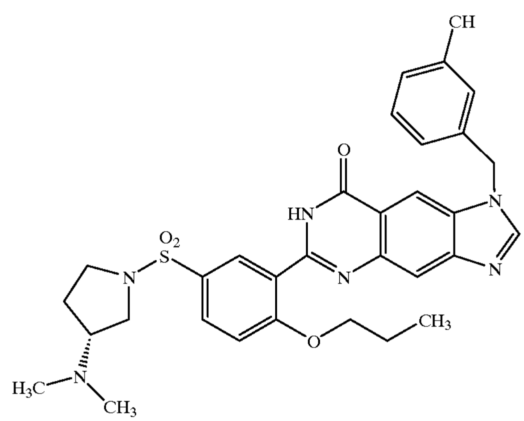 | 98 | 2.90 | LC-MS m + H 612 (mp 218–220) |
| 96 | (R)-1-[[3-[1-[(4-Cyanophenyl)methyl]-7,8-dihydro-8-oxo-1H-imidazo[4,5-g]quinazolin-6-yl]-4-propoxyphenyl]sulfonyl]-3-(dimethylamino)pyrrolidine | 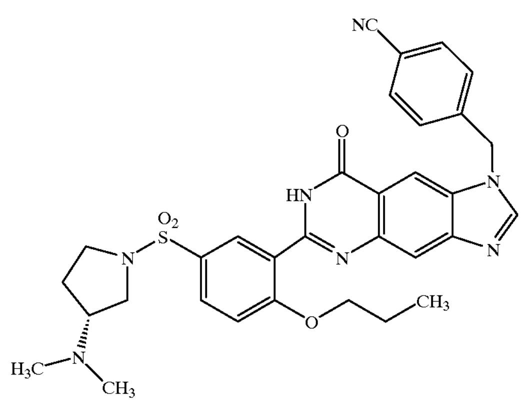 | 97 | 2.90 | LC-MS m + H 612 (mp 217–220) |

TABLE 3-continued

| Ex. No. | Compound Name | Structure | % purity | HPLC retention time (minutes) | Other data (mp ° C.) |
|---|---|---|---|---|---|
| 97 | (R)-1-[[3-[1-[(4-Chlorophenyl)methyl]-7,8-dihydro-8-oxo-1H-imidazo[4,5-g]quinazolin-6-yl]-4-propoxyphenyl]sulfonyl]-3-(dimethylamino)pyrrolidine | 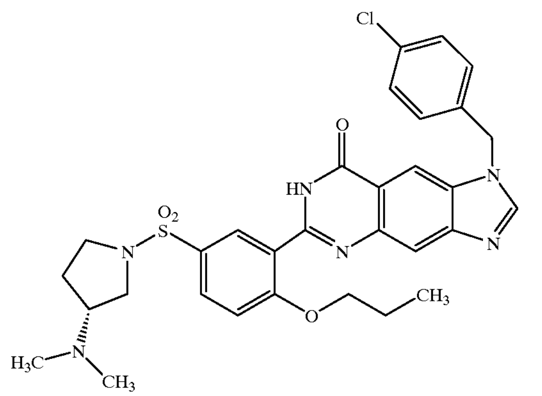 | 98 | 3.30 | LC-MS m + H 622 (mp 220–222) |
| 98 | [3-[1-[(4-Methoxy-3-chlorophenyl)methyl]-7,8-dihydro-8-oxo-1H-imidazo[4,5-g]quinazolin-6-yl]-4-propoxyphenyl]sulfonyl]-4-ethyl piperazine | 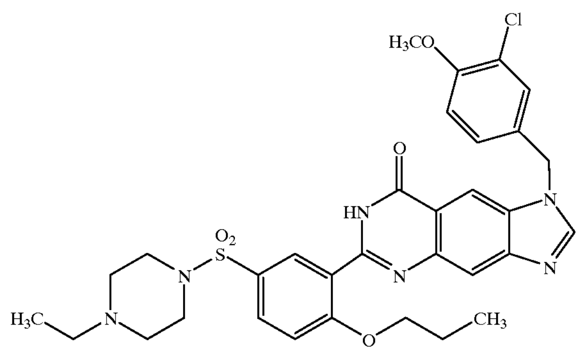 | 98 | 3.20 | LC-MS m + H 652 (mp 125–126) |

EXAMPLE 99

6-[5-(Azidomethyl)-2-propoxyphenyl]-1-[(2-methoxyphenyl)methyl]-1H-imidazo[4,5-g]quinazoline-8(7H)-one

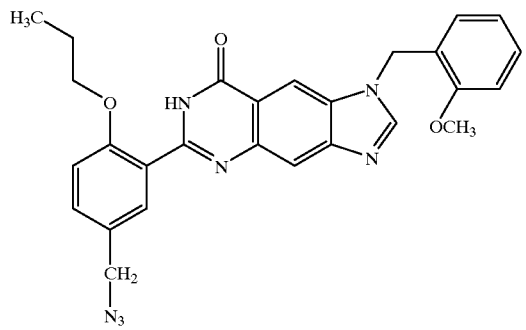

EXAMPLE 100

6-[5-(Aminomethyl)-2-propoxyphenyl]-1-[(2-methoxyphenyl)methyl]-1H-imidazo[4,5-g]quinazoline-8(7H)-one

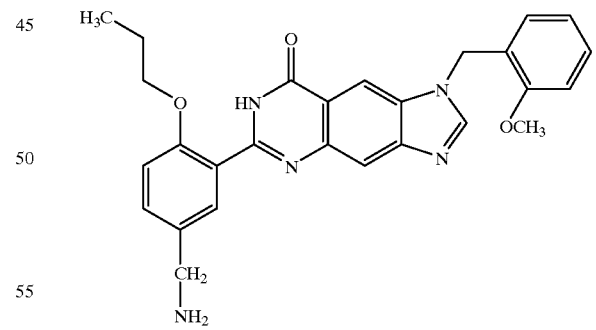

The carboxylic acid of Preparation 14 was coupled with the aniline of Preparation 9E using Method 2 as described in Examples 40 to 48. The amide obtained was cyclized also as described in Examples 40 to 48 to provide the title quinazoline of this Example. Yield 79%; LRMS (M+H) 498; HPLC retention time: 3.93 minutes. YMC S5 ODS 4.6×50 mm column, 4 minute gradient 0% B to 100% B, 4 ml/min flow, solvent A: 10% MeOH-90% $H_2O$-0.2% $H_3PO_4$, solvent B 90% MeOH-10% $H_2O$-0.2% $H_3PO_4$.

The azide moiety of the title compound of Example 99 was reduced to the primary amine of the title compound of this Example as follows: 3.9 gm (7.87 mmol) azide was dissolved in 45 mL ethanol containing 0.40 gm of 10% Pd-C. The reaction mixture was stirred at room temperature overnight under one atmosphere of hydrogen gas. Additional catalyst was added (0.20 gm) and the reaction was stirred for another 24 hours. The catalyst was removed by filtration and the filtrate concentrated to dryness under reduced pressure to give 1.28 gm (35% yield) of the product as a yellow solid. LCMS [M+H] 470; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.04 minutes.

EXAMPLES 101 to 106

The title amine compound of Example 100 was coupled to the appropriate carboxylic acids using Method 2 as described in Examples 40 to 48 to provide the compounds of Examples 103 to 106. The compound of Example 101 was prepared by treating the aforementioned amine compound with acetic anhydride in pyridine. The compound of Example 102 was prepared by refluxing the aforementioned amine compound in formic acid overnight. The compounds of Examples 101 to 106 are described in Table 4 below. HPLC methods for retention times: YMC S5 ODS 4.6×50 mm column, 4 minute gradient 0% B to 100% B, 4 ml/min flow, solvent A: 10% MeOH-90% $H_2O$-0.2% $H_3PO_4$, solvent B 90% MeOH-10% $H_2O$-0.2% $H_3PO_4$.

TABLE 4

| Ex. No. | Compound Name | Structure | % purity | HPLC retention time (minutes) | Other data (mp °C.) |
|---|---|---|---|---|---|
| 101 | N-[[3-[7,8-Dihydro-1-[(2-methoxyphenyl)methyl]-8-oxo-1H-imidazo[4,5-g]quinazolin-6-yl]-4-propoxyphenyl]methyl]acetamide | 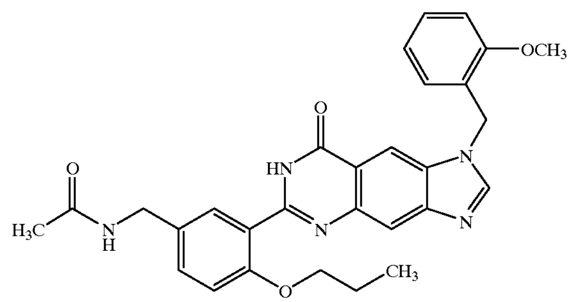 | 95 | 3.40 | m + H 512 (168–170) |
| 102 | N-[[3-[7,8-Dihydro-1-[(2-methoxyphenyl)methyl]-8-oxo-1H-imidazo [4,5-g]quinazolin-6-yl]-4-propoxyphenyl]methyl]formamide | 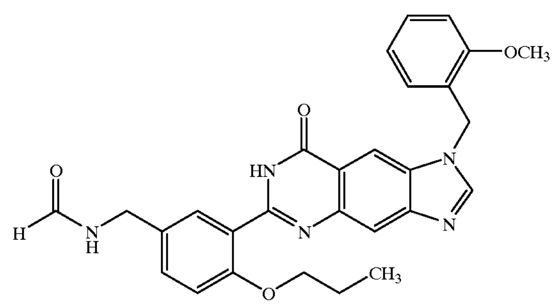 | 95 | 3.40 | m + H 498 (158–159) |
| 103 | N-[[3-[7,8-Dihydro-1-[(2-methoxyphenyl)methyl]-8-oxo-1H-imidazo[4,5-g]quinazolin-6-yl]-4-propoxyphenyl]methyl]-N,N-dimethyl-D-alaninamide | 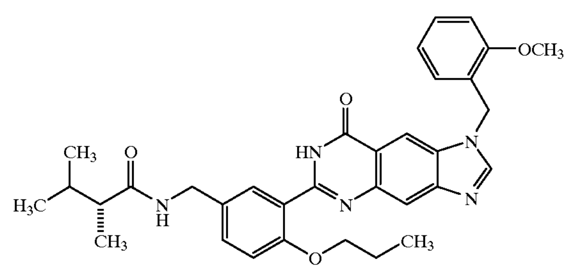 | 95 | 3.40 | m + H 569 (196–197) |
| 104 | N-[[3-[7,8-Dihydro-1-[(2-methoxyphenyl)methyl]-8-oxo-1H-imidazo[4, 5-g]quinazolin-6-yl]-4-propoxyphenyl]methyl]-N,N-dimethylglycinamide | 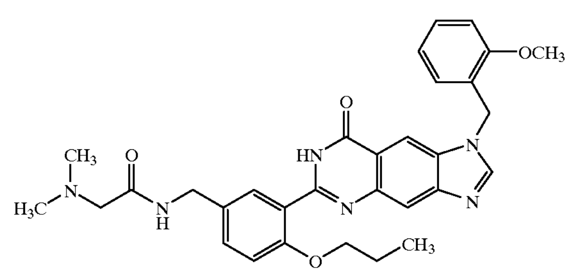 | 98 | 3.10 | m + H 555 (201–202) |

TABLE 4-continued

| Ex. No. | Compound Name | Structure | % purity | HPLC retention time (minutes) | Other data (mp ° C.) |
|---|---|---|---|---|---|
| 105 | N-[[3-[7,8-Dihydro-1-[(2-methoxyphenyl)methyl]-8-oxo-1H-imidazo[4,5-g]quinazolin-6-yl]-4-propoxyphenyl]methyl]-1-methyl-3-piperidinamide | 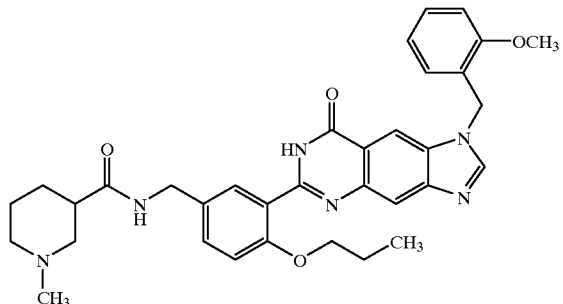 | 94 | 3.20 | m + H 595 (150–153) |
| 106 | N-[[3-[7,8-Dihydro-1-[(2-methoxyphenyl)methyl]-8-oxo-1H-imidazo[4,5-g]quinazolin-6-yl]-4-propoxyphenyl]methyl]-1-methyl-L-prolinamide | 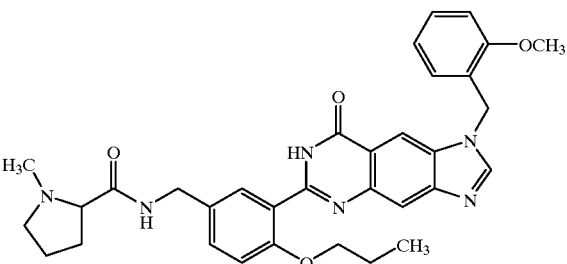 | 90 | 3.20 | m + H 581 (192–194) |

EXAMPLE 107

6-(5-(Aminomethyl)-2-propoxyphenyl)-1-[(4-fluorophenyl)methyl]-1H-imidazo[4,5-g]quinazolin-8(7H)-one

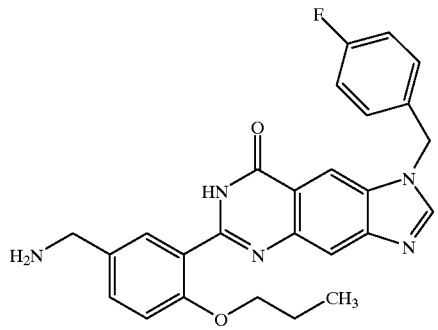

1-(4-Fluorophenylmethyl)-6-(4-cyano-2-propoxyphenyl)-1H-imidazo[4,5-g]quinazolin-8(7H)-one (Example 111, 0.050 gm, 0.11 mmol) was dissolved in 1.5 mL dry THF at room temperature. Lithium aluminum hydride (1.0 M in THF, 0.39 mL, 0.39 mmol) was added. The solution was stirred at room temperature overnight. Excess hydride was quenched by addition of $Na_2SO_4$—$10H_2O$. The suspension was stirred for 15 minutes then filtered. The filtrate was evaporated under reduced pressure and the residual solid was triturated with a mixture of methylene chloride and ether. The undissolved solid was collected by filtration to provide 10 mg (0.02 mmol) of the desired product. The hydrochloride salt had a melting point of 232–235° C. LCMS [M+H] 458; HPLC (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.00 minutes.

EXAMPLE 108

1-[[3-(7,8-Dihydro-8-oxo-1H-imidazo[4,5-g]quinazolin-6-yl)-4-propoxyphenyl]sulfonyl]-(4-methyl piperazine)-3-piperidinecarboxamide

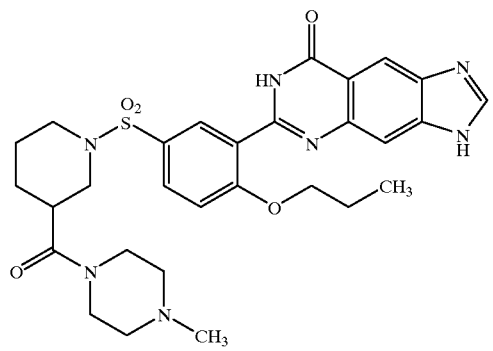

The carboxylic acid title compound of Example 38 (0.050 gm) was dissolved in 2 mL DMF containing 0.011 gm N-methyl piperazine, 0.036 gm DMAP, 0.013 gm HOBt and 0.023 gm EDAC. The reaction was stirred at room temperature overnight. Ethyl acetate (50 mL) was added and washed with water and brine. The organic layer was concentrated under reduced pressure and the residue purified by preparative HPLC to furnish 0.025 gm of the desired product as the TFA salt, mp (TFA salt) 100° C. (with decomp). LCMS [M+H] 594; HPLC (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 2.42 minutes.

EXAMPLE 109

1-[[3-(7,8-Dihydro-8-oxo-1H-imidazol[4,5-g]quinazolin-6-yl)-4-ethoxyphenyl]sulfonyl]-4-methylpiperazine

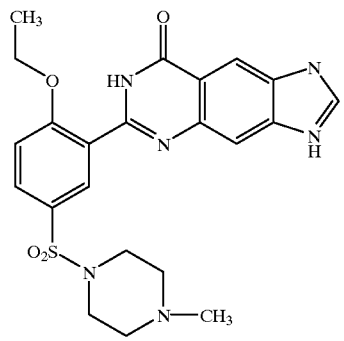

Using appropriate intermediates prepared as per Preparations 2, 3, 4 and 5, the title compound was prepared similarly to Example 2 to afford the title compound as a tan solid: mp 178–181° C.; LRMS (m/z) 469 [MH+].

EXAMPLE 110

1-(4-Fluorophenylmethyl)-6-(4-bromo-2-propoxyphenyl)-1H-imidazo[4,5-g]quinazolin-8(7H)-one

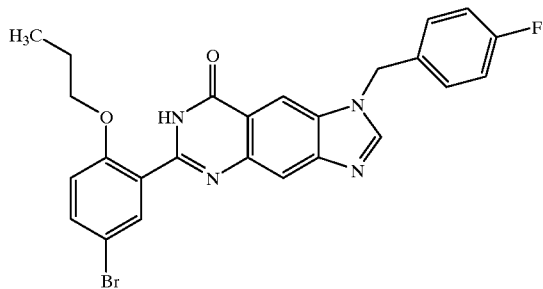

The title compound of Preparation 13 was coupled with the compound from Preparation 9B by the procedure in Examples 40 to 48, Method 2, to afford 4.57 gm (8.7 mmol, 87% yield) of a slightly pink solid. HPLC: (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.70 minutes (~80% pure).

This material was cyclized as described for the preparation of the compounds of Examples 40 to 48 to furnish the title compound of this Example as a beige solid in 82% yield, mp 295–297° C., LCMS [M+H] 508; HPLC: (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 4.19 minutes (≧94% pure).

EXAMPLE 111

1-(4-Fluorophenylmethyl)-6-(4-cyano-2-propoxyphenyl)-1H-imidazo[4,5-g]quinazolin-8(7H)-one

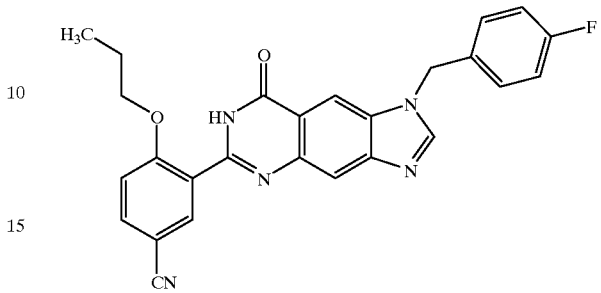

1-(4-Fluorophenylmethyl)-6-(4-bromo-2-propoxyphenyl)-1H-imidazo[4,5-g]quinazolin-8(7H)-one (507 mg, 1 mmol) was dissolved in 6 mL N-methyl-2-pyrrolidinone containing copper (I) cyanide (178 mg, 2 mmol). The reaction was heated to reflux overnight, then cooled to room temperature and poured into 100 mL of 2N aqueous ammonia solution. The solid that precipitated was collected by filtration and washed first with 2N aqueous ammonia, then water and dried in a vacuum oven at 45° C. overnight to afford the title compound as a yellow solid (464 mg, 0.91 mmol, 91% yield). HPLC: (YMC S5 ODS 4.6×50 mm column, 4 minute gradient-0% B to 100% B, 4 mL/min flow, solvent A: 10% MeOH-90% H$_2$O-0.2% H$_3$PO$_4$, solvent B: 90% MeOH-10% H$_2$O-0.2% H$_3$PO$_4$) retention time 3.65 minutes.

EXAMPLE 112

3-[1-[(4-Fluorophenyl)methyl]-7,8-dihydro-8-oxo-1H-imidazo[4,5-g]-quinazolin-6-yl]-4-propoxybenzoic acid

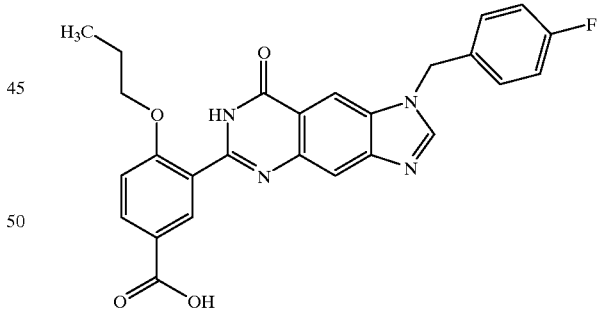

The title compound of Example 111 was added to 10 mL of absolute ethanol containing 10 mL of 10% (w/v) NaOH. The reaction mixture was heated to reflux for 5 hours, then cooled to room temperature. Undissolved solids were removed by filtration and ethanol was removed under reduced pressure. Water (100 mL) was added and the solution was acidified with 10% HCl to pH 2–3. The resulting precipitate was collected by filtration and washed with distilled water, then dried under vacuum at 45° C. overnight to provide the carboxylic acid title compound of this Example in 75% yield as a sand colored solid, mp 295° C.; LCMS [M+H] 473; HPLC: (YMC S5 ODS 4.6×50 mm column, 4 minute gradient-0% B to 100% B, 4 mL/min flow, solvent A: 10% MeOH-90% $H_2O$-0.2% $H_3PO_4$, solvent B: 90% MeOH-10% $H_2O$-0.2% $H_3PO_4$) retention time 3.63 minutes.

What is claimed is:

1. A compound of the following formula I or a salt thereof:

(I)

[Chemical structure of formula I showing a bicyclic system with substituents $R_1$-O, HN, $R_2$, $R_3$, $R_4$, and X, Y, Z positions]

where:
- X, Y and Z are defined such that
  - when X is —N($R_9$)— and Y is —CH=, Z is —N=;
  - when X is —N($R_9$)— and Y is —N=, Z is —N= or —C($R_9$)=;
  - when Z is —N($R_9$)— and Y is —CH=, X is —N=;
  - when Z is —N($R_9$)— and Y is —N=, X is —N= or —C($R_9$)=;
- the dotted lines denote optional double bonds;
- $R_1$ is alkyl, alkenyl, alkynyl, cycloalkyl, cycloalkenyl, aryl, alkoxyalkyl, or haloalkyl;
- $R_2$ is hydrogen, halo, cyano, nitro, —(CH$_2$)$_n$—N$_3$, —(CH$_2$)$_n$—SO$_2$NR$_5$R$_6$, —(CH$_2$)$_n$—CO$_2$R$_7$, —(CH$_2$)$_n$—(C=O)NR$_5$R$_6$, —(CH$_2$)$_n$—NR$_5$R$_6$, —(CH$_2$)$_n$—NH (C=O)R$_8$, or —(CH$_2$)$_n$—NHSO$_2$R$_8$;
- $R_3$ and $R_4$ are each independently hydrogen, alkyl, alkenyl, alkynyl, cycloalkyl, cycloalkylalkyl, cycloalkenyl, cycloalkenylalkyl, halo, aryl, arylalkyl, heterocyclo, heterocycloalkyl, —OR$_{12}$ or —NHR$_{12}$;
- $R_5$, $R_6$, $R_7$ and $R_8$ are each independently hydrogen, heterocyclo or alkyl wherein said alkyl is unsubstituted or substituted with a single substituent selected from —CO$_2$R$_{10}$, hydroxy, amino, mono- or dialkylamino, and heterocyclo; or
- $R_5$ and $R_6$ may, together with the nitrogen to which they are bonded, form a five to seven membered unsubstituted heterocyclic ring or said heterocyclic ring having one or two substituents selected from alkyl, aryl, arylalkyl, heterocyclo, cycloalkyl, hydroxyalkyl, —(CH$_2$)$_n$—CO$_2$R$_{10}$, —N (R$_{10}$)R$_{11}$, —(CH$_2$)$_n$—(CO) NR$_{13}$R$_{14}$, —COR$_{10}$, and —(CH$_2$)$_n$—OR$_{11}$;
- each $R_9$ is independently hydrogen, alkyl, alkenyl, alkynyl, cycloalkyl, cycloalkylalkyl, cycloalkenyl, cycloalkenylalkyl, heterocyclo, heterocycloalkyl, aryl or arylalkyl;
- $R_{10}$, $R_{11}$ and $R_{12}$ are each independently hydrogen, alkyl, alkenyl, alkynyl, cycloalkyl, cycloalkylalkyl, cycloalkenyl, cycloalkenylalkyl, halo, aryl or arylalkyl;
- $R_{13}$ and $R_{14}$ are each independently hydrogen, hydroxy, alkyl, alkoxy, alkoxyalkyl, hydroxyalkyl, alkylaminoalkyl, dialkylaminoalkyl, arylalkyl, heterocycloalkyl, or heterocyclo, or $R_{13}$ and $R_{14}$ may, together with the nitrogen to which they are bonded, form a five to seven membered heterocyclic ring; and n is 0, 1, 2, 3 or 4;
wherein cycloalkyl or cycloalkenyl alone or as part of another group may optionally be substituted by one, two, or three halo atoms, and wherein aryl alone or as part of another group may optionally be substituted by one, two, or three groups selected from halo, cyano, nitro, alkyl, amino, alkylamino, dialkylamino, and alkoxy.

2. A compound of claim 1, wherein:

X is —N($R_9$)— or —N=;

Z is —N= when X is —N($R_9$)—, or is —N($R_9$)— when X is —N=;

Y is —CH= or —N=;

- $R_1$ is $C_1$ to $C_6$ alkyl, $C_2$ to $C_6$ alkenyl, $C_2$ to $C_6$ alkynyl, —(CH$_2$)$_k$O(CH$_2$)$_m$CH$_3$, or $C_1$ to $C_6$ perfluoroalkyl;
- $R_2$ is hydrogen, fluoro, chloro, bromo, iodo, cyano, nitro, —(CH$_2$)$_n$—N$_3$, —(CH$_2$)$_n$—SO$_2$NR$_5$R$_6$, —(CH$_2$)$_n$—CO$_2$R$_7$, —(CH$_2$)$_n$—(C=O)NR$_5$R$_6$, —(CH$_2$)$_n$—NR$_5$R$_6$, —(CH$_2$)$_n$—NH(C=O)R$_8$ or —(CH$_2$)$_n$—NHSO$_2$R$_8$;
- $R_3$ and $R_4$ are each independently hydrogen, $C_1$ to $C_6$ alkyl, $C_2$ to $C_6$ alkenyl, $C_2$ to $C_6$ alkynyl, —CH$_2$-phenyl, —CH$_2$-(substituted phenyl), —CH$_2$—CH$_2$-phenyl, —CH$_2$—CH$_2$-(substituted phenyl), —OR$_{12}$ or —NHR$_{12}$;

k is 2 or 3;

m is 0, 1 or 2;

n is 0, 1, 2, 3 or 4;

- $R_5$ and $R_6$ are each independently hydrogen, heterocyclo or alkyl wherein said alkyl is unsubstituted or substituted with a single substituent selected from —CO$_2$R$_{10}$, hydroxy, dialkylamino, and heterocyclo or $R_5$ and $R_6$ together with the nitrogen to which they are bonded, from a five to seven membered unsubstituted heterocyclic ring or said heterocyclic ring having one or two substituents selected from alkyl, phenyl-alkyl, (substituted phenyl)-alkyl, hydroxyalkyl, —CO$_2$R$_{10}$, —N(R$_{10}$)(R$_{11}$), —(CO)NR$_{13}$R$_{14}$, —COR$_{10}$, and —OR$_{11}$;
- $R_7$ and $R_8$ are each independently hydrogen or $C_1$ to $C_5$ alkyl, wherein said alkyl is unsubstituted or substituted with a single substituent selected from —CO$_2$R$_{10}$, hydroxy, pyridyl, imidazolyl, morpholinyl, and oxadiazolyl;
- $R_9$ is hydrogen, $C_1$ to $C_8$ alkyl, $C_2$ to $C_6$ alkenyl, $C_2$ to $C_6$ alkynyl, —CH$_2$-phenyl, —CH$_2$-(substituted phenyl), —CH$_2$—CH$_2$-phenyl, or —CH$_2$—CH$_2$-(substituted phenyl); and
- $R_{10}$, $R_{11}$, and $R_{12}$ are each independently hydrogen or $C_1$ to $C_6$ alkyl wherein substituted phenyl is a phenyl ring having one, two or three substituents selected from alkyl, halo, cyano, nitro, amino, alkylamino, dialkylamino, and alkoxy.

3. A compound of claim 1 wherein:

Z is —N($R_9$)—;

X is —N=;

Y is —CH=;

$R_1$ is $C_2$ to $C_4$ alkyl;

$R_2$ is hydrogen, halo, cyano, nitro, —(CH$_2$)$_n$—SO$_2$NR$_5$R$_6$, —(CH$_2$)$_n$—CO$_2$R$_7$, —(CH$_2$)$_n$—(C=O)NR$_5$R$_6$, —(CH$_2$)$_n$—NR$_5$R$_6$, —(CH$_2$)$_n$—NH(C=O)R$_8$, or —(CH$_2$)$_n$—NHSO$_2$R$_8$;

R₅ and R₆ are each independently hydrogen, heterocyclo or alkyl, wherein said alkyl is unsubstituted or substituted with a single substituent selected from —CO₂R₁₀, hydroxy, dialkylamino, or heterocyclo or R₅ and R₆ together with the nitrogen to which they are bonded, form a five to seven membered unsubstituted heterocyclic ring or said heterocyclic ring having one or two substituents selected from alkyl, phenyl-alkyl, (substituted phenyl)-alkyl, hydroxyalkyl, —CO₂R₁₀, —N(R₁₀)R₁₁, —(CO)NR₁₃R₁₄, —COR₁₀, and —OR₁₁; and R₉ is hydrogen, C₁ to C₈ alkyl, —CH₂-phenyl, —CH₂-(substituted phenyl), —CH₂—CH₂-phenyl, or —CH₂—CH₂-(substituted phenyl)
wherein substituted phenyl is a phenyl ring having one, two or three substituents selected from alkyl, halo, cyano, nitro, amino, alkylamino, dialkylamino, and alkoxy.

4. A compound of claim 1, wherein X is —N═.

5. A compound of claim 1, wherein R₁ is C₂ to C₄ alkyl.

6. A compound of claim 1, wherein R₂ is —SO₂NR₅R₆, —(C═O)NR₅R₆, —NH(C═O)R₈, or —NHSO₂R₈.

7. A compound of claim 1, wherein R₃ and R₄ are each independently hydrogen, C₁ to C₃ alkyl, —OR₁₂ or —NHR₁₂.

8. A compound of claim 1, selected from the group consisting of:

6-(5-Bromo-2-propoxyphenyl)-1H-imidazo[4,5-g]quinazolin-8(7H)-one;

1-[[3-(7,8-Dihydro-8-oxo-1H-imidazo[4,5-g]quinazolin-6-yl)-4-propoxyphenyl]sulfonyl]-4-methylpiperazine;

1-[[3-(7,8-Dihydro-8-oxo-1H-imidazo[4,5-g]quinazolin-6-yl)-4-propoxyphenyl]sulfonyl]-4-piperidinecarboxylic acid ethyl ester;

1-[[3-(7,8-Dihydro-8-oxo-1H-imidazo[4,5-g]quinazolin-6-yl)-4-propoxyphenyl]sulfonyl]-3-piperidinecarboxylic acid ethyl ester;

3-(7,8-Dihydro-8-oxo-1H-imidazo[4,5-g]quinazolin-6-yl)-N-(2-1H-imidazol-4-ylethyl)-4-propoxybenzenesulfonamide;

3-(7,8-Dihydro-8-oxo-1H-imidazo[4,5-g]quinazolin-6-yl)-N-(1H-indazol-5-yl)-4-propoxybenzenesulfonamide;

4-Benzyl-1-[[3-(7,8-dihydro-8-oxo-1H-imidazo [4,5-g]quinazolin-6-yl)-4-propoxyphenyl]sulfonyl]piperazine;

3-(7,8-Dihydro-8-oxo-1H-imidazo[4,5-g]quinazolin-6-yl)-N-(2-dimethylaminoethyl)-4-propoxybenzenesulfonamide;

6-(2-Ethoxyphenyl)-1H-imidazo[4,5-g]quinazolin-8(7H)-one;

6-(2-Propoxyphenyl)-1H-imidazo[4,5-g]quinazolin-8(7H)-one;

1-[[4-Butoxy-3-(7,8-Dihydro-8-oxo-1H-imidazo[4,5-g]quinazolin-6-yl)phenyl]sulfonyl]-4-methylpiperazine;

3-(7,8-Dihydro-8-oxo-1H-imidazo[4,5-g]quinazolin-6-yl)-N-(4-pyridylmethyl)-4-propoxybenzenesulfonamide;

4-Acetyl-1-[[3-(7,8-Dihydro-8-oxo-1H-imidazo[4,5-g]quinazolin-6-yl)-4-propoxyphenyl]sulfonyl]piperazine;

1-[[3-(7,8-Dihydro-8-oxo-1H-imidazo[4,5-g]quinazolin-6-yl)-4-propoxyphenyl]sulfonyl]-4-ethylpiperazine;

1-[[3-(7,8-Dihydro-8-oxo-1H-imidazo[4,5-g]quinazolin-6-yl)-4-propoxyphenyl]sulfonyl]piperazine;

1-[3-(7,8-Dihydro-8-oxo-1H-imidazo[4,5g]quinazolin-6-yl)-4-propoxy]-4-methylpiperazine]-benzamide;

1-[3-(7,8-Dihydro-8-oxo-1H-imidazo[4,5g]quinazolin-6-yl)-4-propoxy]-3-piperidinecarboxylic acid ethyl ester]-benzamide;

1-[3-(7,8-Dihydro-8-oxo-1H-imidazo[4,5g]quinazolin-6-yl)-4-propoxy]-4-piperidinecarboxylic acid ethyl ester]-benzamide;

6-(2-Propoxyphenyl)-3-propyl-1H-imidazo[4,5-g]quinazolin-8(7H)-one;

6-(2-Propoxyphenyl)-1-propyl-1H-imidazo[4,5-g]quinazolin-8(7H)-one;

3-Ethyl-6-(2-propoxyphenyl)-1H-imidazo[4,5-g]quinazolin-8(7H)-one;

1-Ethyl-6-(2-propoxyphenyl)-1H-imidazo[4,5-g]quinazolin-8(7H)-one;

3-Cyclohexylmethyl-6-(2-propoxyphenyl)-1H-imidazo[4,5-g]quinazolin-8(7H)-one;

1-Cyclohexylmethyl-6-(2-propoxyphenyl)-1H-imidazo[4,5-g]quinazolin-8(7H)-one;

1-(2-Cyclohexylpropyl)-6-(2-propoxyphenyl)-1H-imidazo[4,5-g]quinazolin-8(7H)-one;

1-(Phenylmethyl)-6-(2-propoxyphenyl)-1H-imidazo[4,5-g]quinazolin-8(7H)-one;

3-(Phenylmethyl)-6-(2-propoxyphenyl)-1H-imidazo[4,5-g]quinazolin-8(7H)-one;

1-(4-Chlorophenylmethyl)-6-(2-propoxyphenyl)-1H-imidazo[4,5-g]quinazolin-8(7H)-one;

3-(4-Chlorophenylmethyl)-6-(2-propoxyphenyl)-1H-imidazo[4,5-g]quinazolin-8(7H)-one;

1-(4-Nitrophenylmethyl)-6-(2-propoxyphenyl)-1H-imidazo[4,5-g]quinazolin-8(7H)-one;

3-(4-Nitrophenylmethyl)-6-(2-propoxyphenyl)-1H-imidazo[4,5-g]quinazolin-8(7H)-one;

1-(4-Methoxyphenylmethyl)-6-(2-propoxyphenyl)-1H-imidazo[4,5-g]quinazolin-8(7H)-one;

3-(4-Methoxyphenylmethyl)-6-(2-propoxyphenyl)-1H-imidazo[4,5-g]quinazolin-8(7H)-one;

1-(Phenethyl)-6-(2-propoxyphenyl)-1H-imidazo[4,5-g]quinazolin-8(7H)-one;

3-(Phenethyl)-6-(2-propoxyphenyl)-1H-imidazo[4,5-g]quinazolin-8(7H)-one;

1-(Pyridylmethyl)-6-(2-propoxyphenyl)-1H-imidazo[4,5-g]quinazolin-8(7H)-one;

3-(Pyridylmethyl)-6-(2-propoxyphenyl)-1H-imidazo[4,5-g]quinazolin-8(7H)-one;

1-[[3-(7,8-Dihydro-8-oxo-1H-imidazo[4,5-g]quinazolin-6-yl)-4-propoxyphenyl]sulfonyl]-4-(2-hydroxyethyl)piperazine;

1-[[3-(7,8-Dihydro-8-oxo-1H-imidazo[4,5-g]quinazolin-6-yl)-4-propoxyphenyl]sulfonyl]-4-piperidinecarboxylic acid;

1-[[3-(7,8-Dihydro-8-oxo-1H-imidazo[4,5-g]quinazolin-6-yl)-4-propoxyphenyl]sulfonyl]-3-piperidinecarboxylic acid;

6-(2-Propoxyphenyl)-1H-1,2,3-triazolo[4,5-g]quinazolin-8(7H)-one;

1-[[3-[7,8-Dihydro-8-oxo-1-(phenylmethyl)-1H-imidazo[4,5-g]quinazolin-6-yl]-4-propoxyphenyl]sulfonyl]-4-methylpiperazine;

1-[[3-[1-[(4-Fluorophenyl)methyl]-7,8-dihydro-8-oxo-1H-imidazo[4,5-g]quinazolin-6-yl]-4-propoxyphenyl]sulfonyl]-4-methylpiperazine;

1-[[3-[1-[(4-fluorophenyl)methyl]-7,8-dihydro-8-oxo-1H-imidazo[4,5-g]quinazolin-6-yl]-4-propoxyphenyl] sulfonyl]-4-ethylpiperazine;

1-[[3-[1-[(3-fluorophenyl)methyl]-7,8-dihydro-8-oxo-1H-imidazo[4,5-g]quinazolin-6-yl]-4-propoxyphenyl] sulfonyl]-4-ethylpiperazine;

1-[[3-[7,8-Dihydro-1-[(3-methoxyphenyl)methyl]-8-oxo-1H-imidazo[4,5-g]quinazolin-6-yl]-4-propoxyphenyl] sulfonyl]-4-ethylpiperazine;

1-[[3-[7,8-Dihydro-1-[(2-methoxyphenyl)methyl]-8-oxo-1H-imidazo[4,5- g]quinazolin-6-yl]-4-propoxyphenyl] sulfonyl]-4-ethylpiperazine;

1-[[3-[1-[(3-Chlorophenyl)methyl]-7,8-dihydro-8-oxo-1H-imidazo[4,5-g]quinazolin-6-yl]-4-propoxyphenyl] sulfonyl]-4-methylpiperazine;

1-[[3-[1-[(2-Chlorophenyl)methyl]-7,8-dihydro-8-oxo-1H-imidazo[4,5-g]quinazolin-6-yl]-4-propoxyphenyl] sulfonyl]-4-ethylpiperazine;

(R)-1-[[3-[1-[(4-Fluorophenyl)methyl]-7,8-dihydro-8-oxo-1H-imidazo[4,5-g]quinazolin-6-yl]-4-propoxyphenyl]sulfonyl]-3-(dimethylamino) pyrrolidine;

1-[[3-[7,8-Dihydro-8-oxo-1-(phenylmethyl)-1H-imidazo[4,5-g]quinazolin-6-yl]-4-propoxyphenyl]sulfonyl]-4-ethylpiperazine;

1-[[3-[7,8-Dihydro-8-oxo-1-(phenylmethyl)-1H-imidazo[4,5-g]quinazolin-6-yl]-4-propoxyphenyl]sulfonyl]-4-propylpiperazine;

(R)-1-[[3-[7,8-Dihydro-8-oxo-1-(phenylmethyl)-1H-imidazo[4,5-g]quinazolin-6-yl]-4-propoxyphenyl]sulfonyl]-3-(dimethylamino)pyrrolidine;

(S)-1-[[3-[7,8-Dihydro-8-oxo-1-(phenylmethyl)-1H-imidazo[4,5-g]quinazolin-6-yl]-4-propoxyphenyl]sulfonyl]-3-(dimethylamino)pyrrolidine;

3-(7,8-Dihydro-8-oxo-1H-imidazo[4,5g]quinazolin-6-yl)-4-propoxy benzoic acid;

4-[[3-(7,8-Dihydro-8-oxo-1H-imidazo[4,5-g]quinazolin-6-yl)-4-propoxyphenyl]sulfonyl]-1-piperazineacetic acid ethyl ester;

4-[[3-(7,8-Dihydro-8-oxo-1H-imidazo[4,5-g]quinazolin-6-yl)-4-propoxyphenyl]sulfonyl]-1-ethyl-2-piperazinecarboxylic acid ethyl ester;

3-[[(7,8-Dihydro-8-oxo-1H-imidazo[4,5g]quinazolin-6-yl)-4-propoxyphenyl]carbonyl]-4-ethylpiperazine;

(S)-[[3-(7,8-Dihydro-8-oxo-1H-imidazo[4,5g]quinazolin-6-yl)-4-propoxyphenyl]carbonyl]-3-dimethylaminopyrrolidine;

1-[[3-[7,8-Dihydro-8-oxo-1-(phenylmethyl)-1H-imidazo[4,5-g]quinazolin-6-yl]-4-propoxyphenyl]sulfonyl]-hexahydro-4-methyl-1H-1,4-diazepine;

1-[[3-[7,8-Dihydro-8-oxo-1-(phenylmethyl)-1H-imidazo[4,5-g]quinazolin-6-yl]-4-propoxyphenyl]sulfonyl]-4-dimethyl aminopiperazine;

1-[[3-[7,8-Dihydro-8-oxo-1-(phenylmethyl)-1H-imidazo[4,5-g]quinazolin-6-yl]-4-propoxyphenyl]sulfonyl]-4-isopropylpiperazine;

1-[[3-[7,8-Dihydro-8-oxo-1-(phenylmethyl)-1H-imidazo[4,5-g]quinazolin-6-yl]-4-propoxyphenyl]sulfonyl]-4-phenylpiperazine;

4-[[3-[7,8-Dihydro-8-oxo-1-(phenylmethyl)-1H-imidazo[4,5-g]quinazolin-6-yl]-4-propoxyphenyl]sulfonyl]-N-(1-methylethyl)-1-piperazineacetamide;

1-[[3-[7,8-Dihydro-8-oxo-1-(phenylmethyl)-1H-imidazo[4,5-g]quinazolin-6-yl]-4-propoxyphenyl]sulfonyl]-1-amino-4-methylpiperazine;

1-[[3-[7,8-Dihydro-8-oxo-1-(phenylmethyl)-1H-imidazo[4,5-g]quinazolin-6-yl]-4-propoxyphenyl]sulfonyl]-4-(2-pyridyl)piperazine;

1-[[3-[7,8-Dihydro-8-oxo-1-(phenylmethyl)-1H-imidazo[4,5-g]quinazolin-6-yl]-4-propoxyphenyl]sulfonyl]-[2-(2-aminomethyl)-ethylpyridine];

1-[[3-[7,8-Dihydro-8-oxo-1-(phenylmethyl)-1H-imidazo[4,5-g]quinazolin-6-yl]-4-propoxyphenyl]sulfonyl]-(2-aminoethyl)-pyridine;

1-[[3-[7,8-Dihydro-8-oxo-1-(phenylmethyl)-1H-imidazo[4,5-g]quinazolin-6-yl]-4-propoxyphenyl]sulfonyl]-3-(aminomethyl)-pyridine;

1-[[3-[7,8-Dihydro-8-oxo-1-(phenylmethyl)-1H-imidazo[4,5-g]quinazolin-6-yl]-4-propoxyphenyl]sulfonyl]-[1-(2-aminoethyl)]-piperidine;

1-[[3-[7,8-Dihydro-8-oxo-1-(phenylmethyl)-1H-imidazo[4,5-g]quinazolin-6-yl]-4-propoxyphenyl]sulfonyl]-3-(N,N-dimethylamino)propyl-amine;

1-[[3-[7,8-Dihydro-8-oxo-1-(phenylmethyl)-1H-imidazo[4,5-g]quinazolin-6-yl]-4-propoxyphenyl]sulfonyl]-[4-(2-aminoethyl)]-pyridine;

1-[[3-[7,8-Dihydro-8-oxo-1-(phenylmethyl)-1H-imidazo[4,5-g]quinazolin-6-yl]-4-propoxyphenyl]sulfonyl]-4-(2-fluoro)-phenylpiperazine;

1-[[3-[7,8-Dihydro-8-oxo-1-(phenylmethyl)-1H-imidazo[4,5-g]quinazolin-6-yl]-4-propoxyphenyl]sulfonyl]-4-(2-cyano)-phenylpiperazine;

1-[[3-[7,8-Dihydro-8-oxo-1-(phenylmethyl)-1H-imidazo[4,5-g]quinazolin-6-yl]-4-propoxyphenyl]sulfonyl]-4-cyclohexylpiperazine;

1-[[3-[7,8-Dihydro-8-oxo-1-(phenylmethyl)-1H-imidazo[4,5-g]quinazolin-6-yl]-4-propoxyphenyl]sulfonyl]-4-(2-methoxyethyl) piperazine;

1-[[3-[7,8-Dihydro-8-oxo-1-(phenylmethyl)-1H-imidazo[4,5-g]quinazolin-6-yl]-4-propoxyphenyl]sulfonyl]-[3-(2-aminoethyl)]-pyridine;

1-[[3-[7,8-Dihydro-8-oxo-1-(phenylmethyl)-1H-imidazo[4,5-g]quinazolin-6-yl]-4-propoxyphenyl]sulfonyl]-4-hydroxy piperidine;

1-[[3-[7,8-Dihydro-8-oxo-1-(phenylmethyl)-1H-imidazo[4,5-g]quinazolin-6-yl]-4-propoxyphenyl]sulfonyl]-4-(N-methyl)-1-methylpiperidine;

1-[[3-[7,8-Dihydro-8-oxo-1-(phenylmethyl)-1H-imidazo[4,5-g]quinazolin-6-yl]-4-propoxyphenyl] sulfonamide;

1-[[3-[1-[(4-Fluorophenyl)methyl]-7,8-dihydro-8-oxo-1H-imidazo[4,5-g]quinazolin-6-yl]-4-propoxyphenyl] sulfonamide;

(S)-1-[[3-[1-[(4-Fluorophenyl)methyl]-7,8-dihydro-8-oxo-1H-imidazo[4,5-g]quinazolin-6-yl]-4-propoxyphenyl]carbonyl]-3-(dimethylamino) pyrrolidine;

1-[[3-[1-[(4-Fluorophenyl)methyl]-7,8-dihydro-8-oxo-1H-imidazo[4,5-g]quinazolin-6-yl]-4-propoxyphenyl] carbonyl]-3-amino-1-ethylpiperazine;

1-[[3-[1-[(4-Fluorophenyl)methyl]-7,8-dihydro-8-oxo-1H-imidazo[4,5-g]quinazolin-6-yl]-4-propoxyphenyl] carbonyl]-1-amino-4-methylpiperazine;

1-[[3-[1-[(4-Fluorophenyl)methyl]-7,8-dihydro-8-oxo-1H-imidazo[4,5-g]quinazolin-6-yl]-4-propoxyphenyl] carbonyl]-[2-(2-amino-ethyl)]-pyridine;

1-[[3-[1-[(4-Fluorophenyl)methyl]-7,8-dihydro-8-oxo-1H-imidazo[4,5-g]quinazolin-6-yl]-4-propoxyphenyl] carboxamide;

1-[[3-[1-[(4-Fluorophenyl)methyl]-7,8-dihydro-8-oxo-1H-imidazo[4,5-g]quinazolin-6-yl]-4-propoxyphenyl]-N,N-dimethyl-carboxamide;

1-[[3-[1-[(4-Fluorophenyl)methyl]-7,8-dihydro-8-oxo-1H-imidazo[4,5-g]quinazolin-6-yl]-4-propoxyphenyl] carbonyl]-2,6-dimethyl piperazine;

1-[[3-[1-[(4-Fluorophenyl)methyl]-7,8-dihydro-8-oxo-1H-imidazo[4,5-g]quinazolin-6-yl]-4-propoxyphenyl] carbonyl]-N-methyl-[2-(2-aminoethyl)-pyridine;

1-[[3-[1-[(4-Fluorophenyl)methyl]-7,8-dihydro-8-oxo-1H-imidazo[4,5-g]quinazolin-6-yl]-4-propoxyphenyl] carbonyl]-4-aminomethyl-1-N-methyl piperidine;

1-[[3-[1-[(4-Fluorophenyl)methyl]-7,8-dihydro-8-oxo-1H-imidazo[4,5-g]quinazolin-6-yl]-4-propoxyphenyl] carbonyl]-2-isopropylamino-ethanol;

(R)-3-[[[3-[1-[(4-Fluorophenyl)methyl]-7,8-dihydro-8-oxo-1H-imidazo[4,5-g]quinazolin-6-yl]-4-propoxyphenyl]carbonyl]amino]-1-pyrrolidineacetic acid ethyl ester;

1-[[3-[1-[(4-Fluorophenyl)methyl]-7,8-dihydro-8-oxo-1H-imidazo[4,5-g]quinazolin-6-yl]-4-propoxyphenyl] carbonyl]-4-piperidine carboxylic acid ethyl ester;

1-Ethyl-4-[[3-[1-[(4-fluorophenyl)methyl]-7,8-dihydro-8-oxo-1H-imidazo[4,5-g]quinazolin-6-yl]-4-propoxyphenyl]carbonyl]piperazine;

1-[[3-[1-[(4-Fluorophenyl)methyl]-7,8-dihydro-8-oxo-1H-imidazo[4,5-g]quinazolin-6-yl]-4-ethoxyphenyl] carboxamide;

(R)-1-[[3-[1-[(4-Methoxyphenyl)methyl]-7,8-dihydro-8-oxo-1H-imidazo[4,5-g]quinazolin-6-yl]-4-propoxyphenyl]sulfonyl]-3-(dimethylamino) pyrrolidine;

(R)-1-[[3-[1-[(3-Cyanophenyl)methyl]-7,8-dihydro-8-oxo-1H-imidazo[4,5-g]quinazolin-6-yl]-4-propoxyphenyl]sulfonyl]-3-(dimethylamino) pyrrolidine;

(R)-1-[[3-[1-[(4-Cyanophenyl)methyl]-7,8-dihydro-8-oxo-1H-imidazo[4,5-g]quinazolin-6-yl]-4-propoxyphenyl]sulfonyl]-3-(dimethylamino) pyrrolidine;

(R)-1-[[3-[1-[(4-Chlorophenyl)methyl]-7,8-dihydro-8-oxo-1H-imidazo[4,5-g]quinazolin-6-yl]-4-propoxyphenyl]sulfonyl]-3-(dimethylamino) pyrrolidine;

[3-[1-[(4-Methoxy-3-chlorophenyl)methyl]-7,8-dihydro-8-oxo-1H-imidazo[4,5-g]quinazolin-6-yl]-4-propoxyphenyl]sulfonyl]-4-ethyl piperazine;

6-[5-(Azidomethyl)-2-propoxyphenyl]-1-[(2-methoxyphenyl)methyl]-1H-imidazo[4,5-g] quinazoline-8(7H)-one;

6-[5-(Aminomethyl)-2-propoxyphenyl]-1-[(2-methoxyphenyl)methyl]-1H-imidazo[4,5-g] quinazoline-8(7H)-one;

N-[[3-[7,8-Dihydro-1-[(2-methoxyphenyl)methyl]-8-oxo-1H-imidazo[4,5-g]quinazolin-6-yl]-4-propoxyphenyl]methyl]acetamide;

N-[[3-[7,8-Dihydro-1-[(2-methoxyphenyl)methyl]-8-oxo-1H-imidazo[4,5-g]quinazolin-6-yl]-4-propoxyphenyl]methyl]formamide;

N-[[3-[7,8-Dihydro-1-[(2-methoxyphenyl)methyl]-8-oxo-1H-imidazo[4,5-g]quinazolin-6-yl]-4-propoxyphenyl]methyl]-N,N-dimethyl-D-alaninamide;

N-[[3-[7,8-Dihydro-1-[(2-methoxyphenyl)methyl]-8-oxo-1H-imidazo[4,5-g]quinazolin-6-yl]-4-propoxyphenyl]methyl]-N,N-dimethylglycinamide;

N-[[3-[7,8-Dihydro-1-[(2-methoxyphenyl)methyl]-8-oxo-1H-imidazo[4,5-g]quinazolin-6-yl]-4-propoxyphenyl]methyl]-1-methyl-3-piperidinamide;

N-[[3-[7,8-Dihydro-1-[(2-methoxyphenyl)methyl]-8-oxo-1H-imidazo[4,5-g]quinazolin-6-yl]-4-propoxyphenyl]methyl]-1-methyl-L-prolinamide;

6-[5-(Aminomethyl)-2-propoxyphenyl]-1-[(4-fluorophenyl)methyl]-1H-imidazo[4,5-g]quinazolin-8 (7H)-one;

1-[[3-(7,8-Dihydro-8-oxo-1H-imidazo[4,5-g]quinazolin-6-yl)-4-propoxyphenyl]sulfonyl]-(4-methyl piperazine)-3-piperidinecarboxamide;

1-[[3-(7,8-Dihydro-8-oxo-1H-imidazol[4,5-g]quinazolin-6-yl)-4-ethoxyphenyl]sulfonyl]4-methylpiperazine;

1-(4-Fluorophenylmethyl)-6-(4-bromo-2-propoxyphenyl)-1H-imidazo[4,5-g]quinazolin-8(7H)-one;

1-(4-Fluorophenylmethyl)-6-(4-cyano-2-propoxyphenyl)-1H-imidazo[4,5-g]quinazolin-8(7H)-one; and 3-[1-[(4-Fluorophenyl)methyl]-7,8-dihydro-8-oxo-1H-imidazo[4,5-g]-quinazolin-6-yl]-4-propoxybenzoic acid.

9. A method for the treatment of a cGMP-associated condition, comprising the step of administering to a mammal in need thereof an amount effective therefor of one or more compounds of claim 1.

10. A method for the treatment of erectile dysfunction, comprising the step of administering to a mammal in need thereof an amount effective therefor of one or more compounds of claim 1.

11. A method for the treatment of one of following disorders: hypertension, angina, heart failure, restenosis, atherosclerosis, dyslipidemia, reduced blood vessel patency, thrombus, either venous or arterial, myocardial infarction, peripheral vascular disease, stroke, bronchitis, chronic asthma, allergic asthma, allergic rhinitis, glaucoma, diseases characterized by disorders of gut motility, and forms of cancer responsive to the inhibition of cGMP PDE, comprising the step of administering to a mammal in need thereof an amount effective therefor of one or more compounds of claim 1.

12. A pharmaceutical composition for the treatment of a cGMP-associated condition, comprising a pharmaceutically acceptable vehicle or diluent and one or more compounds of claim 1 in an amount effective therefor.

13. A compounds of claim 1, wherein:

$R_1$ is $C_2$ to $C_4$ alkyl;

$R_2$ is $SO_2NR_5R_6$ or $—(C=O)NR_5R_6$;

$R_3$ and $R_4$ are each independently hydrogen or $—NHR_{12}$;

$R_5$ and $R_6$ together with the nitrogen to which they are bonded complete a five or six membered heterocyclic ring optionally containing one additional nitrogen atom, said heterocyclic ring being unsubstituted or having a single substituent selected from $C_1$ to $C_4$ alkyl and $—N(R_{10})R_{11}$; and $R_9$ is hydrogen, $—CH_2$-phenyl, $—CH_2$-(substituted phenyl), $—CH_2—CH_2$-phenyl, or $—CH_2—CH_2$-(substituted phenyl), wherein said substituted phenyl is a phenyl ring having one, two, or three substituents selected from alkyl, halo, cyano, nitro, amino, alkylamino, dialkylamino, and alkoxy.

14. A compound of claim 1, wherein:

Z is $—N(R_9)—$; and $R_9$ is hydrogen, $—C_1$ to $C_8$ alkyl, $—CH_2$-phenyl, $—CH_2$-(substituted phenyl), $—CH_2—CH_2$-phenyl, or —CH$_2$—CH$_2$-(substituted phenyl) wherein said substituted phenyl is a phenyl ring having one, two, or three substituents selected from alkyl, halo, cyano, nitro, amino, alkylamino, dialkylamino and alkoxy.

15. A compound of claim 1, wherein:

$R_5$ and $R_6$ are each independently selected from hydrogen, heterocyclo, and $C_1$–$C_5$ alkyl, wherein said alkyl is unsubstituted or substituted with a single substituent selected from —CO$_2$R$_{10}$, hydroxy, dialkylamino, pyridyl, imidazolyl, morpholinyl, or oxadiazolyl or $R_5$ and $R_6$ together with the nitrogen to which they are bonded complete a five to seven membered heterocyclic ring optionally containing one additional nitrogen atom, said heterocyclic ring being unsubstituted or substituted with one or two substituents selected from $C_1$ to $C_4$ alkyl, phenyl-alkyl, (substituted phenyl)-alkyl, hydroxyalkyl, —CO$_2$R$_{10}$, —N(R$_{10}$)R$_{11}$, —C(O)NR$_{13}$R$_{14}$, —COR$_{10}$, and —OR$_{11}$, wherein said substituted phenyl is a phenyl ring having, one, two or three substituents selected from alkyl, halo, cyano, nitro, amino, alkylamino, dialkylamino, and alkoxy.

16. A method for the treatment of one of the following disorders: hypertension, angina, heart failure, restenosis, atherosclerosis, and dyslipidemia comprising the steps of administering to a mammal in need thereof an amount effective therefor of one or more compounds of claim 1.

17. A method for the treatment of male erectile dysfunction or impaired blood flow to the corpus cavernosum of a female, comprising the step of administering to said male or female patient an effective amount therefor of one or more compounds of claim 1.

* * * * *